(12) United States Patent
Mathai

(10) Patent No.: US 12,194,263 B2
(45) Date of Patent: *Jan. 14, 2025

(54) DEVICES AND METHODS FOR DELIVERY OF PHARMACEUTICAL COMPOSITIONS

(71) Applicant: Pocket Naloxone Corp., Bethesda, MD (US)

(72) Inventor: Ashanthi Mathai, Bethesda, MD (US)

(73) Assignee: Pocket Naloxone Corp., Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/523,321

(22) Filed: Nov. 10, 2021

(65) Prior Publication Data

US 2022/0062602 A1 Mar. 3, 2022

Related U.S. Application Data

(63) Continuation of application No. 16/831,555, filed on Mar. 26, 2020, now Pat. No. 11,191,934, which is a continuation of application No. PCT/US2020/024661, filed on Mar. 25, 2020.

(60) Provisional application No. 62/981,929, filed on Feb. 26, 2020, provisional application No. 62/823,800, filed on Mar. 26, 2019.

(51) Int. Cl.
| | | |
|---|---|---|
| *A61M 31/00* | (2006.01) |
| *A61K 9/00* | (2006.01) |
| *A61K 9/08* | (2006.01) |
| *A61K 31/485* | (2006.01) |

(52) U.S. Cl.
CPC ........... *A61M 31/00* (2013.01); *A61K 9/0043* (2013.01); *A61K 9/08* (2013.01); *A61K 31/485* (2013.01); *A61M 2205/3368* (2013.01); *A61M 2210/0618* (2013.01)

(58) Field of Classification Search
CPC .... A61M 31/00; A61M 35/00; A61M 35/003; A61M 35/006; A61M 2205/3368; A61M 2210/0618
See application file for complete search history.

(56) References Cited

U.S. PATENT DOCUMENTS

| | | | |
|---|---|---|---|
| 4,229,447 | A | 10/1980 | Porter |
| 4,464,378 | A | 10/1984 | Hussain |
| 4,476,116 | A | 10/1984 | Anik |
| 4,596,795 | A | 6/1986 | Pitha |
| 4,755,386 | A | 7/1988 | Hsiao et al. |

(Continued)

FOREIGN PATENT DOCUMENTS

| | | |
|---|---|---|
| CA | 2 795 156 A1 | 10/2011 |
| CN | 201085740 Y | 7/2008 |

(Continued)

OTHER PUBLICATIONS

International Search Report and Written Opinion for PCT Application No. PCT/US2020/024661 dated Jun. 16, 2020, 35 pages.

(Continued)

*Primary Examiner* — Jessica Arble

(57) ABSTRACT

Described herein are devices for delivering pharmaceutical compositions to individuals in need thereof. Also described herein are methods of using the devices described herein to deliver pharmaceutical compositions to individuals in need thereof.

4 Claims, 27 Drawing Sheets

(56) References Cited

U.S. PATENT DOCUMENTS

| | | |
|---|---|---|
| 4,938,763 A | 7/1990 | Dunn et al. |
| 5,011,692 A | 4/1991 | Fujioka et al. |
| 5,017,381 A | 5/1991 | Maruyama et al. |
| 5,116,817 A | 5/1992 | Anik |
| 5,229,135 A | 7/1993 | Philippon et al. |
| 5,324,519 A | 6/1994 | Dunn et al. |
| 5,562,077 A | 10/1996 | Schultz |
| 5,702,716 A | 12/1997 | Dunn et al. |
| 5,739,136 A | 4/1998 | Ellinwood et al. |
| 5,744,153 A | 4/1998 | Yewey et al. |
| 5,837,284 A | 11/1998 | Mehta et al. |
| 5,840,329 A | 11/1998 | Bai |
| 5,843,060 A | 12/1998 | Cercone |
| 5,866,154 A | 2/1999 | Bahal |
| 5,871,461 A | 2/1999 | Atanasoska et al. |
| 5,990,194 A | 11/1999 | Dunn et al. |
| 6,391,452 B1 | 5/2002 | Antonsen et al. |
| 7,115,275 B2 | 10/2006 | Carlot et al. |
| 7,597,901 B2 | 10/2009 | Carlot et al. |
| 7,655,243 B2 | 2/2010 | Deem et al. |
| 7,674,904 B2 | 3/2010 | Doshan et al. |
| 8,105,817 B2 | 1/2012 | Deem et al. |
| 8,133,502 B2 | 3/2012 | Carlot et al. |
| 8,343,992 B2 | 1/2013 | Doshan et al. |
| 8,388,600 B1 | 3/2013 | Eldredge |
| 8,506,996 B2 | 8/2013 | Cronk et al. |
| 8,636,684 B2 | 1/2014 | Deem et al. |
| 8,852,224 B2 | 10/2014 | Cronk et al. |
| 9,211,253 B2 | 12/2015 | Crystal et al. |
| 9,468,747 B2 | 10/2016 | Crystal et al. |
| 9,480,644 B2 | 11/2016 | Crystal et al. |
| 9,511,210 B2 | 12/2016 | Deem et al. |
| 9,561,177 B2 | 2/2017 | Keegan et al. |
| 9,597,327 B2 | 3/2017 | Doshan et al. |
| 9,629,965 B2 | 4/2017 | Crystal et al. |
| 9,642,848 B2 | 5/2017 | Amancha et al. |
| 9,642,868 B2 | 5/2017 | Wei |
| 9,700,707 B2 | 7/2017 | Deem et al. |
| 9,707,226 B2 | 7/2017 | Keegan et al. |
| 9,775,838 B2 | 10/2017 | Keegan et al. |
| 9,956,232 B2 | 5/2018 | Wei |
| 10,052,465 B2 | 8/2018 | Deem et al. |
| 10,085,937 B2 | 10/2018 | Keegan et al. |
| 10,238,648 B2 | 3/2019 | Stinchcomb et al. |
| 10,441,538 B2 | 10/2019 | Amancha et al. |
| 10,653,690 B1 | 5/2020 | Savmarker et al. |
| 10,874,358 B2 | 12/2020 | Insler et al. |
| 11,020,343 B2 | 6/2021 | Strang et al. |
| 11,027,072 B2 | 6/2021 | Flather et al. |
| 11,191,934 B2 | 12/2021 | Mathai et al. |
| 11,202,757 B2 | 12/2021 | Temtsin-Krayz et al. |
| 11,202,894 B1* | 12/2021 | Thau .......... A61M 35/006 |
| 11,278,709 B1 | 3/2022 | Mathai et al. |
| 11,426,513 B2 | 8/2022 | Tyson |
| 11,628,139 B2 | 4/2023 | Amancha |
| 2001/0004644 A1 | 6/2001 | Levin |
| 2004/0219107 A1 | 11/2004 | Clarot et al. |
| 2006/0275343 A1 | 12/2006 | Clarot et al. |
| 2007/0267011 A1 | 11/2007 | Deem et al. |
| 2008/0021369 A1 | 1/2008 | Deem et al. |
| 2008/0107475 A1 | 5/2008 | Wojcik et al. |
| 2010/0004628 A1 | 1/2010 | Clarot et al. |
| 2011/0027353 A1 | 2/2011 | Cronk et al. |
| 2011/0195455 A1 | 8/2011 | Benson et al. |
| 2011/0256070 A1 | 10/2011 | Martin et al. |
| 2012/0089078 A1 | 4/2012 | Deem et al. |
| 2013/0085472 A1* | 4/2013 | Shaari ............ A61M 5/3286 |
| | | 604/506 |
| 2013/0184684 A1 | 7/2013 | Yardley |
| 2013/0337031 A1 | 12/2013 | Kisak et al. |
| 2014/0114233 A1 | 4/2014 | Deem et al. |
| 2014/0155843 A1 | 10/2014 | Cronk et al. |
| 2015/0174061 A1 | 6/2015 | Wyse et al. |
| 2015/0265752 A1* | 9/2015 | Wei ................ A61K 9/0053 |
| | | 514/75 |
| 2015/0283091 A1 | 10/2015 | Vargas Rincon |
| 2015/0297617 A1 | 10/2015 | Given et al. |
| 2015/0297846 A1 | 10/2015 | Given et al. |
| 2015/0367115 A1 | 12/2015 | Deem et al. |
| 2016/0038406 A1 | 2/2016 | Hariharan |
| 2016/0058156 A1 | 3/2016 | Chiasson |
| 2016/0151257 A1* | 6/2016 | Klingman ............ A61K 8/0208 |
| | | 424/401 |
| 2016/0158464 A1 | 6/2016 | Hijlkema et al. |
| 2016/0184564 A1 | 6/2016 | Spearman et al. |
| 2016/0243188 A1 | 8/2016 | Shailubhai et al. |
| 2016/0339198 A1 | 11/2016 | Fraser et al. |
| 2016/0354363 A1 | 12/2016 | Amancha et al. |
| 2017/0020863 A1 | 1/2017 | Wright et al. |
| 2017/0042884 A1 | 2/2017 | Amancha et al. |
| 2017/0143096 A1 | 5/2017 | Zembrod |
| 2017/0165255 A1 | 6/2017 | Yum et al. |
| 2017/0189428 A1 | 7/2017 | Wei |
| 2017/0252337 A1 | 9/2017 | Amancha et al. |
| 2017/0266422 A1 | 9/2017 | Deem et al. |
| 2017/0296489 A1 | 10/2017 | Wei |
| 2017/0304192 A1 | 10/2017 | Strang et al. |
| 2017/0333688 A1 | 11/2017 | Parikh et al. |
| 2017/0348224 A1 | 12/2017 | Hariharan |
| 2018/0021771 A1 | 1/2018 | Tamir |
| 2018/0030405 A1 | 2/2018 | Subhadra |
| 2018/0133731 A1 | 5/2018 | Ritsche |
| 2018/0193332 A1* | 7/2018 | Loughlin .............. A61K 47/186 |
| 2019/0015323 A1 | 1/2019 | Keegan et al. |
| 2019/0038549 A1 | 2/2019 | Brecht |
| 2019/0070105 A1 | 3/2019 | Amancha et al. |
| 2019/0070396 A1* | 3/2019 | Johnson ................. A61K 9/006 |
| 2020/0306514 A1 | 10/2020 | Mathai et al. |
| 2020/0352934 A1 | 11/2020 | Loughlin et al. |
| 2021/0077382 A1 | 3/2021 | Crystal et al. |
| 2021/0128462 A1 | 5/2021 | Temtsin-Krayz et al. |
| 2021/0161835 A1 | 6/2021 | Presti |
| 2021/0186954 A1 | 6/2021 | Plucinski et al. |
| 2021/0228570 A1 | 7/2021 | Renger |
| 2021/0315552 A1 | 10/2021 | Kabaria et al. |
| 2021/0330903 A1 | 10/2021 | Patel |
| 2021/0338574 A1 | 11/2021 | Strang et al. |
| 2021/0401827 A1 | 12/2021 | Crystal et al. |
| 2022/0016026 A1 | 1/2022 | McCarty |
| 2022/0160618 A1 | 5/2022 | Boyer et al. |
| 2022/0241268 A1 | 8/2022 | Pergolizzi |
| 2022/0313686 A1 | 10/2022 | Barenholz et al. |
| 2022/0313687 A1 | 10/2022 | Li et al. |
| 2022/0387421 A1 | 12/2022 | Plucinski et al. |
| 2023/0001084 A1 | 1/2023 | Lee et al. |
| 2023/0095235 A1 | 3/2023 | Huang et al. |
| 2023/0149388 A1 | 5/2023 | Fukhari et al. |

FOREIGN PATENT DOCUMENTS

| | | |
|---|---|---|
| EP | 3 082 816 B1 | 3/2019 |
| WO | 1996/09047 A1 | 3/1996 |
| WO | 1999/53841 A1 | 10/1999 |
| WO | 2000/62757 A1 | 10/2000 |
| WO | 2004/024225 A1 | 3/2004 |
| WO | 2004/024226 A1 | 3/2004 |
| WO | 2006/098650 A1 | 9/2006 |
| WO | 2007/126851 A2 | 11/2007 |
| WO | 2007/137235 A2 | 11/2007 |
| WO | 2009/040595 A1 | 4/2009 |
| WO | 2009/067536 A2 | 5/2009 |
| WO | 2012/156317 A2 | 11/2012 |
| WO | 2014/076569 A2 | 5/2014 |
| WO | 2014/121342 A1 | 8/2014 |
| WO | 2016/007729 A1 | 1/2016 |
| WO | 2016/132223 A1 | 8/2016 |
| WO | 2017/218854 A1 | 12/2017 |
| WO | 2017/223566 A1 | 12/2017 |
| WO | 2018/064672 A1 | 4/2018 |
| WO | 2018/089709 A1 | 5/2018 |
| WO | 2018/093666 A1 | 5/2018 |
| WO | 2019/005759 A1 | 1/2019 |
| WO | 2019/048527 A1 | 3/2019 |

(56) References Cited

FOREIGN PATENT DOCUMENTS

| WO | 2019/074701 A1 | 4/2019 |
| WO | 2020/198327 A1 | 10/2020 |
| WO | 2021/225973 A1 | 11/2021 |

OTHER PUBLICATIONS

Jeong et al. Biodegradable block copolymers as injectable drug-delivery systems. Nature 388:860-862 (1997).
Jeong et al. Drug release from biodegradable injectable thermosensitive hydrogel of PEGPLGA-PEG triblock copolymers. Journal of Controlled Release 63:155-163 (2000).
Jeong et al. Thermosensitive sol-gel reversible hydrogels. Advanced Drug Delivery Reviews, 54:37-51 (2002).
International Search Report and Written Opinion for Application No. PCT/US2022/019918, mailed on Jun. 14, 2022, 17 pages.
Djupesland, Per Gisle "Nasal drug delivery devices: characteristics and performance in a clinical perspective—a review", Drug Delivery and Translational Research, Oct. 2012, vol. 3, No. 1, pp. 42-62.
Esposito et al., "Collection by trained pediatricians or parents of mid-turbinate nasal flocked swabs for the detection of influenza viruses in childhood", Virology Journal, Jan. 2010, vol. 7, No. 85, 4 pages.
Keller, Lea-Adriana et al., "Intranasal drug delivery: opportunities and toxicologic challenges during drug development", Drug Delivery and translational research, 2022, vol. 12, pp. 735-757.
International Preliminary Report on Patentability for PCT Application No. PCT/US2020/024661 dated Sep. 28, 2021, 31 pages.
International Preliminary Report on Patentability for PCT Application No. PCT/US2022/019918 dated Sep. 12, 2023, 8 pages.
Non-Final Office Action mailed on Jul. 21, 2020, in U.S. Appl. No. 16/831,555, 11 pages.
Final Office Action mailed on Nov. 20, 2020, in U.S. Appl. No. 16/831,555, 15 pages.
Non-Final Office Action mailed on Mar. 8, 2021, in U.S. Appl. No. 16/831,555, 9 pages.
Final Office Action mailed on Jun. 7, 2021, in U.S. Appl. No. 16/831,555, 9 pages.
Notice of Allowance mailed on Oct. 27, 2021, in U.S. Appl. No. 16/831,555, 11 pages.
Non-Final Office Action mailed on Jan. 26, 2022, in U.S. Appl. No. 17/523,321, 10 pages.
Final Office Action mailed on Apr. 4, 2022, in U.S. Appl. No. 17/523,321, 9 pages.
Non-Final Office Action mailed on Sep. 15, 2022, in U.S. Appl. No. 17/523,321, 11 pages.
Final Office Action mailed on Apr. 10, 2023, in U.S. Appl. No. 17/523,321, 12 pages.
Notice of Allowance mailed on Dec. 1, 2021, in U.S. Appl. No. 17/463,079, 9 pages.
Non-Final Office Action mailed on May 12, 2022, in U.S. Appl. No. 17/682,261, 23 pages.
Final Office Action mailed on Sep. 14, 2022, in U.S. Appl. No. 17/682,261, 25 pages.
Non-Final Office Action mailed on Apr. 7, 2023, in U.S. Appl. No. 17/682,261, 23 pages.
U.S. Appl. No. 16/831,321, filed Mar. 26, 2020, which issued as U.S. Pat. No. 11,191,934 on Dec. 7, 2021.
U.S. Appl. No. 17/523,321, filed Nov. 10, 2021, which published as US 2022/00062602 A1 on Mar. 3, 2022.
PCT International Application No. PCT/US2020/024661 filed on Mar. 25, 2020, which published as WO 2020/198327 on Oct. 1, 2020.
U.S. Appl. No. 17/463,079, filed Aug. 31, 2021, which issued as U.S. Pat. No. 11,278,709, which issued on Mar. 22, 2022.
U.S. Appl. No. 17/682,261, filed Feb. 28, 2022, which published as U.S. Application Publication No. 2022/0288366 A1 on Sep. 15, 2022, and issued as U.S. Pat. No. 12,017,026 on Jun. 5, 2024.
U.S. Appl. No. 18/660,859, filed May 10, 2024.
PCT International Application No. PCT/US2022/019918 filed on Mar. 11, 2022, which published as PCT International Publication No. WO 2022/192652 on Sep. 15, 2022.
Notice of Allowance mailed on Feb. 12, 2024, in U.S. Appl. No. 17/682,261, 9 pages.

* cited by examiner

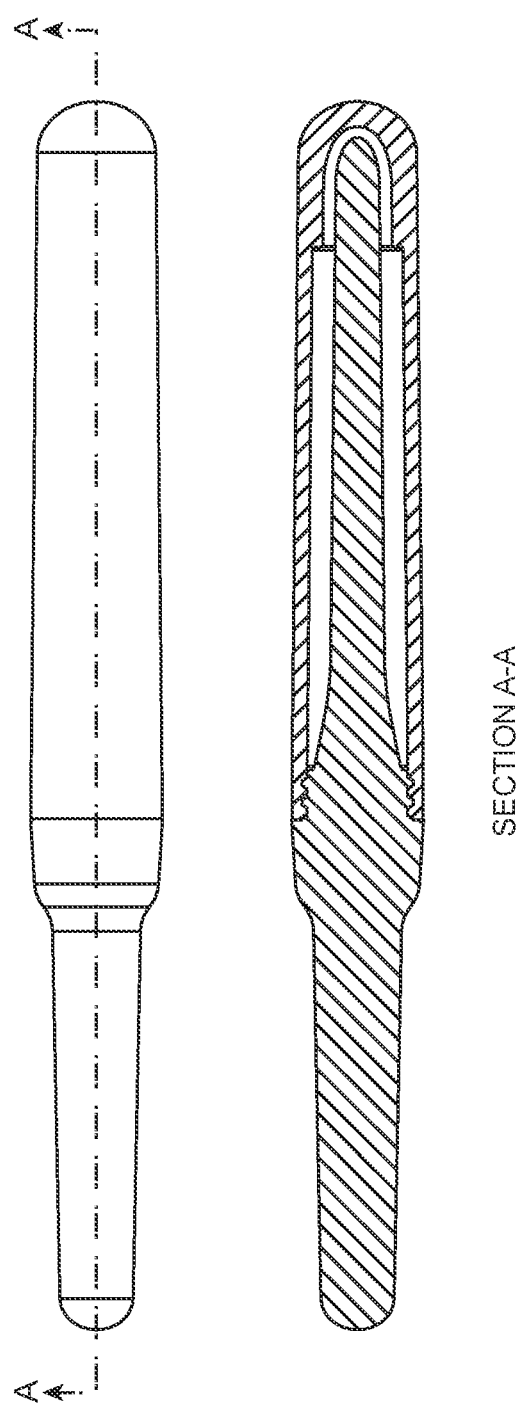
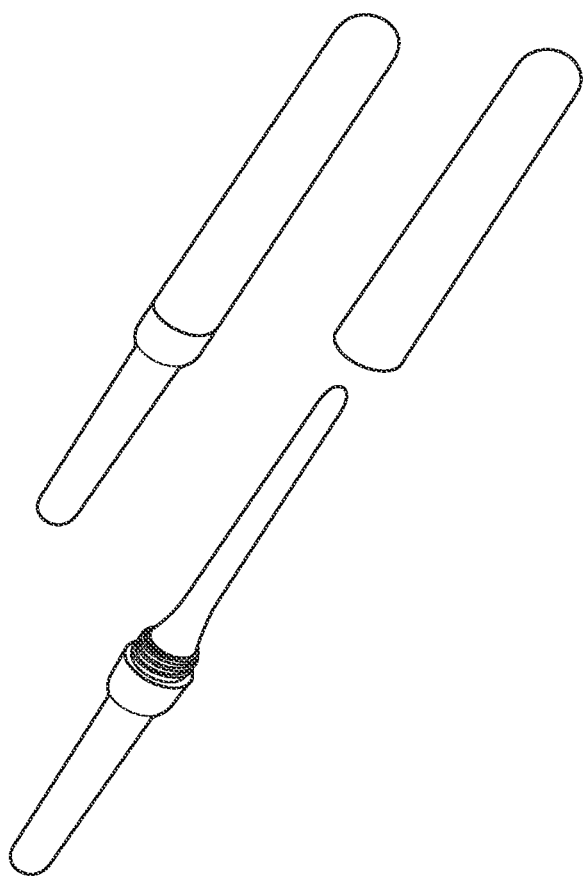
FIG. 10

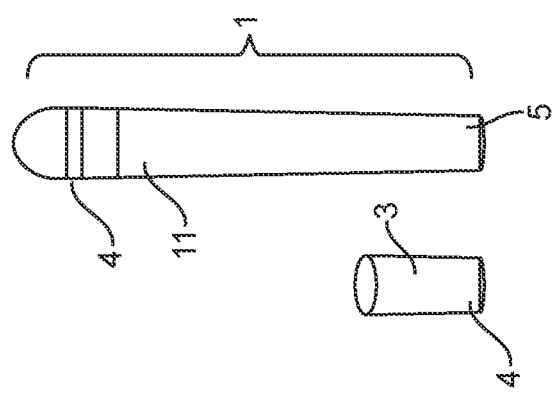
FIG. 14

Swab
+
Separate soln.

Pre-saturated
Swab applicator

VARIANT
telescoping plastic case open by sliding one end out

Pre-saturated
swab applicator

DEVICES AND METHODS FOR DELIVERY OF PHARMACEUTICAL COMPOSITIONS

CROSS-REFERENCE

This application is a continuation U.S. application Ser. No. 16/831,555, filed on Mar. 26, 2020, which is a continuation of International application No. PCT/US2020/024661, filed on Mar. 25, 2020, which claims the benefit of U.S. Provisional Application No. 62/981,929, filed on Feb. 26, 2020, and U.S. Provisional Application No. 62/823,800, filed on Mar. 26, 2019, each of which is incorporated herein by reference in its entirety.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND

Opioid abuse and overdosing are known to cause tens of thousands of deaths annually. This also represents massive social and economic costs. Among the tools used by emergency medical services (e.g. medical technicians, police officers, clinicians, etc.), the opioid antagonist naloxone (N-Allylnoroxymorphone) is accepted as a vital aid in preventing death by overdose. This compound is capable of being effectively delivered intravenously, subcutaneously, intramuscularly, and intranasally via a variety of mechanisms. It is known in the healthcare and pharmaceutical industry that intranasal spray devices can be effectively used to administer potentially life-saving treatment, even when handled by minimally trained individuals. The U.S. Surgeon General issued a Public Service Announcement in April, 2018, advising "I, Surgeon General of the United States Public Health Service, VADM Jerome Adams, am emphasizing the importance of the overdose-reversing drug naloxone. For individuals currently taking high doses of opioids as prescribed for pain, individuals misusing prescription opioids, individuals using illicit opioids such as heroin or fentanyl, health care practitioners, family and friends of people who have an opioid use disorder, and community members who come into contact with people at risk for opioid overdose, knowing how to use naloxone and keeping it within reach can save a life." To further the availability of this treatment, the United States Food and Drug Administration has called for an over-the-counter (i.e. readily available on retail shelves and online for purchase without the need to speak with a pharmacist) product suitable for applying this drug in the event of emergencies.

Presently, the most prevalent means for dispensing opioid antagonists at a point-of-care capacity involve nasal spray dispensing opioid antagonists to the nasal cavity. Such nasal spray is inadequate in addressing the opioid overdose epidemic. For example, fentanyl is a highly potent synthetic opioid that is now the leading contributor to opioid overdose deaths. To counter fentanyl, higher doses of opioid antagonists are needed. The multiple dosing is required for, for example, in situations where a nasal spray is used to treat fentanyl induced overdose. In addition, current opioid antagonist dispensing products are expensive. Such pricing precludes healthcare professionals, which often rely on grants, from purchasing sufficient quantities of opioid antagonist dispensing product to serve the public. Healthcare professionals have repeatedly pleaded for the prices of these products to be reduced. A lower pricing will also enable schools, colleges, public libraries, and many other entities to have a stock of opioid antagonist dispensing products, thus complying with the Public Health Advisory put out by the U.S. Surgeon General.

Current opioid antagonist dispensing products are kept behind the pharmacy counter. Though these products can be purchased without a prescription, speaking with a pharmacist is still required in order to purchase them. Stigma remains a significant barrier. Therefore, FDA put out an unprecedented call for a true over-the-counter (OTC) opioid antagonist dispensing product. FDA deems the need for OTC opioid antagonist dispensing product so critical that it takes the unprecedented step of developing and testing the consumer drug facts label templates and putting these templates in the public domain to encourage development of such OTC product.

SUMMARY

The present disclosure relates generally to portable emergency-deployment applicators or devices for counteracting opioid overdoses, specifically via the intranasal administration of an opioid antagonist or other active or therapeutic ingredients. The present disclosure aims to provide a simplified, portable, cost-effective means of delivering a pharmaceutical composition to an individual via the nasal cavity. It is contemplated that the present disclosure can feature tamper-safe construction as a feature of the particular construction described herein. These features will further include simplified, single-use hermetic seals separating the internally stored medicant from external contamination or degradation. The specific structures related to these functions are understood to increase shelf-life, decrease manufacturing costs, and enable any user to be confident that their tools will remain suitably potent to treat an overdosing individual.

In addition, devices and methods described herein are beneficial in that, for example, they cause a therapeutic to be administrable to a patient when a patient is in multiple different positions. For example, the devices and methods described herein are configured to deliver a therapeutic to a nasal cavity and/or upper airway of an individual when the individual is lying in a supine position. For example, the devices and methods described herein are configured to deliver a therapeutic to a nasal cavity and/or upper airway of an individual when the individual is lying in a prone position. For example, the devices and methods described herein are configured to deliver a therapeutic to a nasal cavity and/or upper airway of an individual when the individual is lying on his or her side. For example, the devices and methods described herein are configured to deliver a therapeutic to a nasal cavity and/or upper airway of an individual when the individual is in a seated position. For example, the devices and methods described herein are configured to deliver a therapeutic to a nasal cavity and/or upper airway of an individual when the individual is standing. This feature is beneficial in that, for example, it allows for effective and speedy administration of a therapeutic to an individual when the individual is found down and unresponsive.

In addition, devices and methods described herein are configured to cause a therapeutic to be administered to different anatomical surfaces of the nasal passage and/or upper airway of an individual. As a result, an applicator of a therapeutic can be inserted into a nasal passage and/or upper airway in different orientations and directions with respect to the nasal passage and/or upper airway and still deliver the therapeutic to the nasal passage and/or upper airway. Described herein, in some embodiments, is a device for delivering a naloxone containing formulation to a surface of a nasal passage of an individual, the device comprising: an applicator; a cover; and the naloxone containing formulation; wherein the naloxone containing formulation is held by a surface of the applicator and positioned on the surface of the applicator so that when the device is inserted into the nasal passage of the individual, the naloxone containing formulation is transmitted to the surface of the nasal passage via direct contact of the applicator surface with the surface of the nasal passage. In some embodiments, the cover and the applicator are connected by an engagement between the cover and the applicator. In some embodiments, the engagement is a threaded engagement. In some embodiments, said cover comprises a seal. In some embodiments, the device further comprises a frangible connection between the cover and the applicator, and wherein the frangible connection is broken when the cover is disconnected from the applicator. In some embodiments, the device includes a reservoir. In some embodiments, the applicator has the configuration of a nasal trumpet. In some embodiments, the nasal trumpet has a conical shape and is curved along its longitudinal axis so that it conforms to the anatomy of the nasal passage. In some embodiments, the nasal trumpet comprises a proximal end; a distal end; and a tubular member connecting the proximal end to the distal end, said tubular member comprises at least one lumen. In some embodiments, the proximal end comprises a flanged end. In some embodiments, the proximal end comprises an opening. In some embodiments, the opening of the proximal end forms a fluid communication with the at least one lumen. In some embodiments, the proximal end comprises at least one injection port, said at least one injection port forms a fluid communication with the at least one lumen of the tubular member. In some embodiments, the distal comprises a beveled end. In some embodiments, the beveled end comprises an opening. In some embodiments, the opening of the beveled end forms a fluid communication with the at least one lumen. In some embodiments, the tubular member comprises at least one opening on a longitudinal surface of the tubular member. In some embodiments, the at least one opening on the longitudinal surface of the tubular member forms a fluid communication with the at least one lumen. In some embodiments, the at least one opening comprises at least one linear opening. In some embodiments, the at least one opening comprises at least one mesh opening. In some embodiments, the nasal trumpet comprises a slit. In some embodiments, the nasal trumpet comprises an inflatable cuff. In some embodiments, the at least one lumen comprises a reservoir for storing the naloxone containing formulation. In some embodiments, the applicator comprises a swab that is positioned on an applicator tip. In some embodiments, the applicator has an applicator tip comprising a roller-ball, and the surface of the applicator that holds the naloxone containing formulation is a surface of the roller-ball. In some embodiments, the applicator has an applicator tip that is movable relative to the applicator and that is configured to be manually advanced relative to the applicator, and wherein the surface of the applicator which holds the naloxone containing formulation is a surface of the applicator tip. In some embodiments, the applicator tip is configured to move relative to the applicator when the applicator is rotated relative to the applicator tip. In some embodiments, the applicator comprises a shaft or a stick. In some embodiments, the naloxone containing formulation comprises naloxone hydrochloride. In some embodiments, the naloxone containing formulation comprises a viscosity between about 0.01 centipoise to about 1,000,000 centipoise at 20 degrees Celsius. In some embodiments, the naloxone containing formulation comprises a viscosity between about 0.1 centipoise to about 100,000 centipoise at 20 degrees Celsius. In some embodiments, the naloxone containing formulation comprises a viscosity between about 1 centipoise to about 10,000 centipoise at 20 degrees Celsius. In some embodiments, the naloxone containing formulation comprises a solvent. In some embodiments, the naloxone containing formulation comprises at least one tonicity agent. In some embodiments, the naloxone containing formulation comprises at least one preservative. In some embodiments, the naloxone containing formulation comprises at least one chelating agent. In some embodiments, the naloxone containing formulation comprises at least one stabilizing agent. In some embodiments, the naloxone containing formulation comprises at least one thickening agent. In some embodiments, the naloxone containing formulation comprises at least one thinning agent. In some embodiments, the naloxone containing formulation comprises at least one surfactant. In some embodiments, the naloxone containing formulation comprises at least one excipient. In some embodiments, the naloxone containing formulation comprises a penetration enhancer. In some embodiments, the naloxone containing formulation comprises at least one additional active ingredient, said at least one additional active ingredient is not naloxone hydrochloride. In some embodiments, the at least one more active ingredient comprises a respiratory stimulant. In some embodiments, the naloxone containing formulation comprises a pH between about 1.5 to about 6.9. In some embodiments, the pH is between about 5.5 to about 6.9. In some embodiments, the naloxone containing formulation is an aqueous formulation. In some embodiments, the naloxone containing formulation is a gel formulation. In some embodiments, the naloxone containing formulation is a semi-solid formulation. In some embodiments, the naloxone containing formulation is a solid formulation. In some embodiments, the solid formulation is a powder formulation, said powder formulation comprises powder naloxone hydrochloride. In some embodiments, the solid formulation is a bead formulation, said bead formulation comprises beads comprising naloxone hydrochloride. In some embodiments, the solid formulation is a crystal formulation, said crystal formulation comprises crystals comprising naloxone hydrochloride. In some embodiments, the applicator delivers at least 150 µl of the naloxone containing formulation to the nasal passage of the individual. In some embodiments, the applicator delivers at least about 45 mg/ml of naloxone hydrochloride. In some embodiments, the applicator completes delivery of the naloxone containing formulation within 1 second. In some embodiments, the applicator completes delivery of the naloxone containing formulation after at least 1 second. In some embodiments, the device further comprises a thermal and/or humidity regulator.

Described herein, in some instances, is a method for delivering a naloxone containing formulation to nasal passage of an individual, the method comprising: receiving a delivery device comprising an applicator, a cover, and the naloxone containing formulation, wherein the naloxone containing formulation is held by a surface of the applicator; and inserting the delivery device into the nasal passage of the individual so that the surface of the applicator upon which the naloxone containing formulation is held contacts a surface of the nasal passage. In some embodiments, the cover and the applicator are connected by an engagement between the cover and the applicator. In some embodiments, the engagement is a threaded engagement. In some embodiments, wherein said cover comprises a seal. In some embodiments, the device further comprises a frangible connection between the cover and the applicator, and wherein the frangible connection is broken when the cover is disconnected from the applicator. In some embodiments, the device includes a reservoir. In some embodiments, the applicator has the configuration of a nasal trumpet. In some embodiments, the nasal trumpet has a conical shape and is curved along its longitudinal axis so that it conforms to the anatomy of the nasal passage. In some embodiments, the applicator comprises a swab that is positioned on an applicator tip. In some embodiments, the applicator has an applicator tip comprising a roller-ball, and the surface of the applicator that holds the naloxone containing formulation is a surface of the roller ball. In some embodiments, the applicator has an applicator tip that is movable relative to the applicator and that is configured to be manually advanced relative to the applicator, and wherein the surface of the applicator which holds the naloxone containing formulation is a surface of the applicator tip. In some embodiments, the applicator tip is configured to move relative to the applicator when the applicator is rotated relative to the applicator tip. In some embodiments, the applicator comprises a shaft or a stick. In some embodiments, the naloxone containing formulation comprises naloxone hydrochloride. In some embodiments, the naloxone containing formulation comprises a viscosity between about 0.01 centipoise to about 1,000,000 centipoise at 20 degrees Celsius. In some embodiments, the naloxone containing formulation comprises a viscosity between about 0.1 centipoise to about 100,000 centipoise at 20 degrees Celsius. In some embodiments, the naloxone containing formulation comprises a viscosity between about 1 centipoise to about 10,000 centipoise at 20 degrees Celsius. In some embodiments, the naloxone containing formulation comprises a solvent. In some embodiments, the naloxone containing formulation comprises at least one tonicity agent. In some embodiments, the naloxone containing formulation comprises at least one preservative. In some embodiments, the naloxone containing formulation comprises at least one chelating agent. In some embodiments, the naloxone containing formulation comprises at least one stabilizing agent. In some embodiments, the naloxone containing formulation comprises at least one thickening agent. In some embodiments, the naloxone containing formulation comprises at least one thinning agent. In some embodiments, the naloxone containing formulation comprises at least one surfactant. In some embodiments, the naloxone containing formulation comprises at least one excipient. In some embodiments, the naloxone containing formulation comprises a penetration enhancer. In some embodiments, the naloxone containing formulation comprises at least one additional active ingredient, said at least one additional active ingredient is not naloxone hydrochloride. In some embodiments, the at least one more active ingredient comprises a respiratory stimulant. In some embodiments, the naloxone containing formulation comprises a pH between about 1.5 to about 6.9. In some embodiments, the pH is between about 5.5 to about 6.9. In some embodiments, the naloxone containing formulation is an aqueous formulation. In some embodiments, the naloxone containing formulation is a gel formulation. In some embodiments, the naloxone containing formulation is a semi-solid formulation. In some embodiments, the naloxone containing formulation is a solid formulation. In some embodiments, the solid formulation is a powder formulation, said powder formulation comprises powder naloxone hydrochloride. In some embodiments, the applicator delivers at least 150 µl of the naloxone containing formulation to the nasal passage of the individual. In some embodiments, the applicator delivers at least about 45 mg/ml of naloxone hydrochloride. In some embodiments, the applicator completes delivery of the naloxone containing formulation within 1 second. In some embodiments, the applicator completes delivery of the naloxone containing formulation after at least 1 second. In some embodiments, the device further comprises a thermal and/or humidity regulator.

Described herein is a nasal trumpet comprising: a proximal end; a distal end; a tubular member connecting the proximal end to the distal end, said tubular member comprises at least one lumen; and a slit. In some embodiments, the proximal end comprises a flanged end. In some embodiments, the proximal end comprises an opening. In some embodiments, the opening of the proximal end forms a fluid communication with the at least one lumen. In some embodiments, the proximal end comprises at least one injection port. In some embodiments, the at least one injection port forms a fluid communication with the at least one lumen. In some embodiments, the proximal end comprises a protrusion. In some embodiments, the distal end comprises a beveled end. In some embodiments, the distal end comprises an opening. In some embodiments, the opening of the distal end forms a fluid communication with the at least one lumen. In some embodiments, the at least one lumen comprises a reservoir. In some embodiments, the tubular member comprises at least one opening on a longitudinal surface of the tubular member. In some embodiments, the at least one opening forms a fluid communication with the at least one lumen. In some embodiments, the at least one opining comprises a linear opening. In some embodiments, the at least one opening comprises a mesh opening. In some embodiments, the nasal trumpet comprises the slit along a longitudinal length of the nasal trumpet. In some embodiments, the nasal trumpet comprises the slit along an entire longitudinal length of the nasal trumpet. In some embodiments, the nasal trumpet comprises the slit along at least 50% longitudinal length of the nasal trumpet. In some embodiments, the nasal trumpet comprises the slit along at most 50% longitudinal length of the nasal trumpet. In some embodiments, the nasal trumpet further comprises an inflatable cuff.

Described herein is a nasal trumpet for delivering a naloxone containing formulation to a surface of a nasal passage of an individual, the nasal trumpet comprising: a proximal end; a distal end; and a tubular member connecting the proximal end to the distal end, said tubular member comprises at least one lumen, wherein the naloxone containing formulation is transmitted to the surface of the nasal passage by direct contact a surface of the nasal trumpet to the surface of the nasal passage. In some embodiments, the proximal end comprises a flanged end. In some embodiments, the proximal end comprises an opening. In some embodiments, the opening of the proximal end forms a fluid communication with the at least one lumen. In some embodiments, the proximal end comprises a protrusion. In some embodiments, the proximal end comprises at least one injection port. In some embodiments, the at least one injection port forms a fluid communication with the at least one lumen. In some embodiments, the distal end comprises a beveled end. In some embodiments, the distal end comprises an opening. In some embodiments, the opening of the distal end forms fluid communication with the at least one lumen. In some embodiments, the tubular member comprises at least one opening on a longitudinal surface of the tubular member. In some embodiments, the at least one opening comprises at least one linear opening. In some embodiments, the at least one opening comprises at least one mesh opening. In some embodiments, the at least one lumen comprises a reservoir. In some embodiments, the at least one lumen comprises a reservoir for storing the naloxone containing formulation, In some embodiments, the nasal trumpet further comprises a slit along a longitudinal axis of the nasal trumpet. In some embodiments, the nasal trumpet further comprises an inflatable cuff.

Described herein is a method for delivering a naloxone containing formulation to nasal passage of an individual, the method comprising: receiving a nasal trumpet, said nasal trumpet comprising: a proximal end; a distal end; and a tubular member connecting the proximal end to the distal end, said tubular member comprises at least one lumen; and inserting the nasal trumpet into the nasal passage of the individual so that the nasal trumpet directly contacts a surface of the nasal passage, thereby delivering the naloxone containing formulation. In some embodiments, the proximal end comprises at least one injection port. In some embodiments, the naloxone containing formulation is injected into the at least one injection port of the nasal trumpet. In some embodiments, the distal end comprises an opening. In some embodiments, the naloxone containing formulation is delivered by direct contact of the opening of the distal end to the surface of the nasal passage. In some embodiments, the at least one lumen comprises a reservoir for storing the naloxone containing formulation. In some embodiments, the tubular member comprises at least one opening on a longitudinal surface of the tubular member. In some embodiments, the at least one opening comprise at least one linear opening. In some embodiments, the at least one opening comprises a mesh opening. In some embodiments, the naloxone containing formulation is stored on the longitudinal surface of the tubular member. In some embodiments, the naloxone containing formulation is delivered by direct contact the at least one opening of the tubular member to the surface of the nasal passage.

Described herein is a method for delivering a naloxone containing formulation to nasal passage of an individual in need of endotracheal intubation, the method comprising: receiving a nasal trumpet, said nasal trumpet comprising: a proximal end; a distal end; a tubular member connecting the proximal end to the distal end, said tubular member comprises at least one lumen; and a slit along a longitudinal length of the nasal trumpet; inserting a fiberoptic scope coupled to an endotracheal tube at least partially into the at least one lumen of the tubular member; inserting the nasal trumpet into the nasal passage of the individual so that the nasal trumpet directly contacts a surface of the nasal passage, thereby delivering the naloxone containing formulation; removing the nasal trumpet from the nasal passage by sliding the fiberoptic scope coupled to the endotracheal tube through the slit, thereby separating the fiberoptic scoped coupled to the endotracheal tube from the at least one lumen of the nasal trumpet; and pushing the fiberoptic scope coupled to the endotracheal tube into a tracheal of the individual, thereby supporting breathing of the individual. In some embodiments, the proximal end comprises at least one injection port. In some embodiments, the naloxone containing formulation is injected into the at least one injection port of the nasal trumpet. In some embodiments, the distal end comprises an opening. In some embodiments, the naloxone containing formulation is delivered by direct contact of the opening of the distal end to the surface of the nasal passage. In some embodiments, the tubular member comprises at least one opening on a longitudinal surface of the tubular member. In some embodiments, the at least one opening comprise at least one linear opening. In some embodiments, the at least one opening comprises a mesh opening. In some embodiments, the naloxone containing formulation is stored on the longitudinal surface of the tubular member. In some embodiments, the naloxone containing formulation is delivered by direct contact of the at least one opening of the tubular member to the surface of the nasal passage. In some embodiments, the method comprises inserting the endotracheal tube via nasal trumpet reduces trauma to nasal mucosa during endotracheal intubation.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments.

FIG. 10 is a schematic view of an alternate embodiment of an illustrative device described herein, where the base is rounded and not flat.

FIG. 14 illustrates the device comprising an applicator in the form of a roll-on or roller-ball for delivering a pharmaceutical composition by directly contacting the roll-on or roller ball located on the tip of the applicator to the nasal passage or nasal cavity of an individual who is in need of the pharmaceutical composition.

FIG. 19 also illustrates an embodiment where the pharmaceutical composition can be stored on the outside surface of the applicator portion of the nasal trumpet.

FIG. 21A illustrates openings along the longitudinal axis of the nasal trumpet, where the pharmaceutical composition can be dispensed in one direction when the applicator of the nasal trumpet is directly contacted with nasal passage. FIG. 21B illustrates a different version of the nasal trumpet of FIG. 21A, where the pharmaceutical composition can be dispensed in more than one directions when the applicator of the nasal trumpet is directly contacted with the nasal passage.

DETAILED DESCRIPTION

Figure 1:
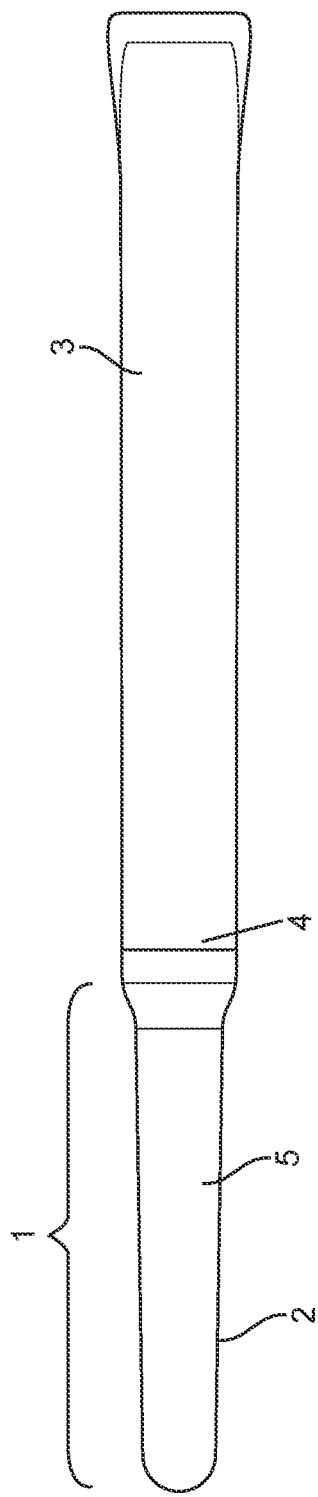
FIG. 1 is top view of an illustrative device described herein.
Figure 2:
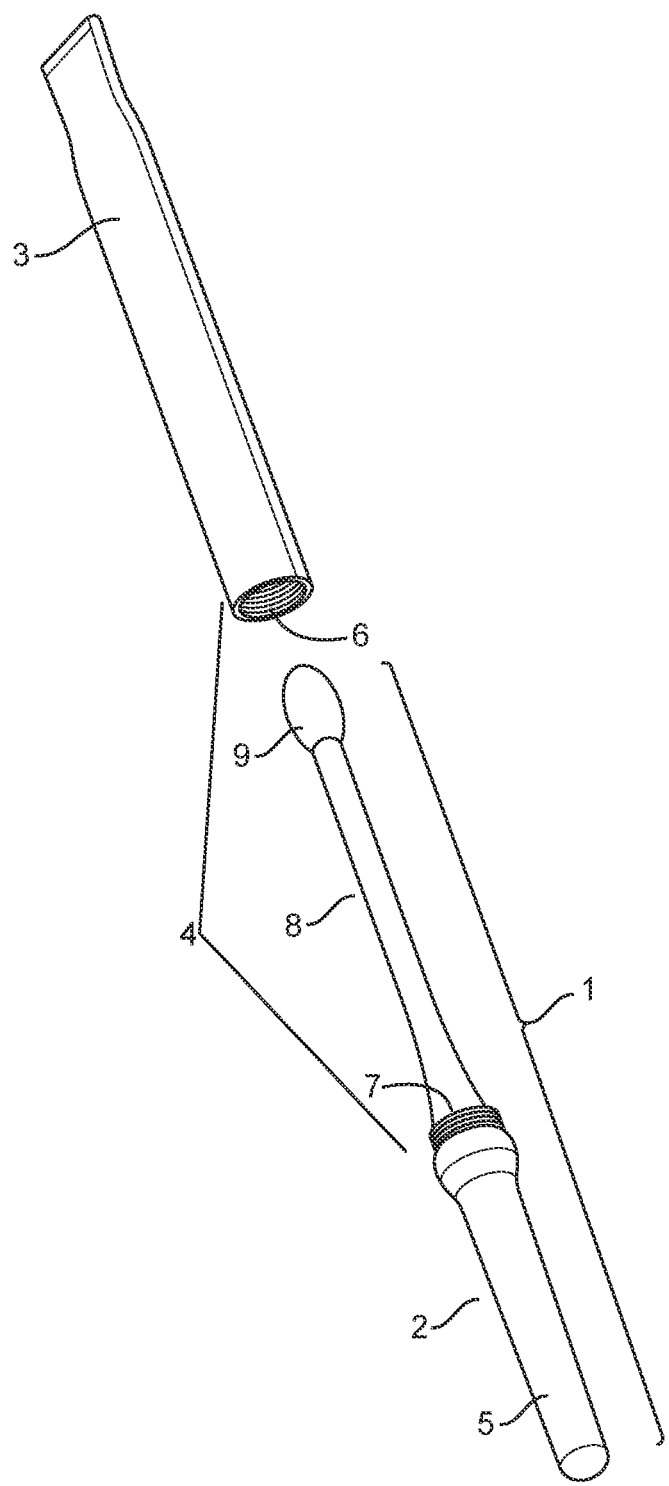
FIG. 2 is an exploded perspective view of an illustrative device described herein, where cover 3 and the applicator 1 (applicator can be without an applicator tip) are separated from each other to create a broken engagement 4.
Figure 3:
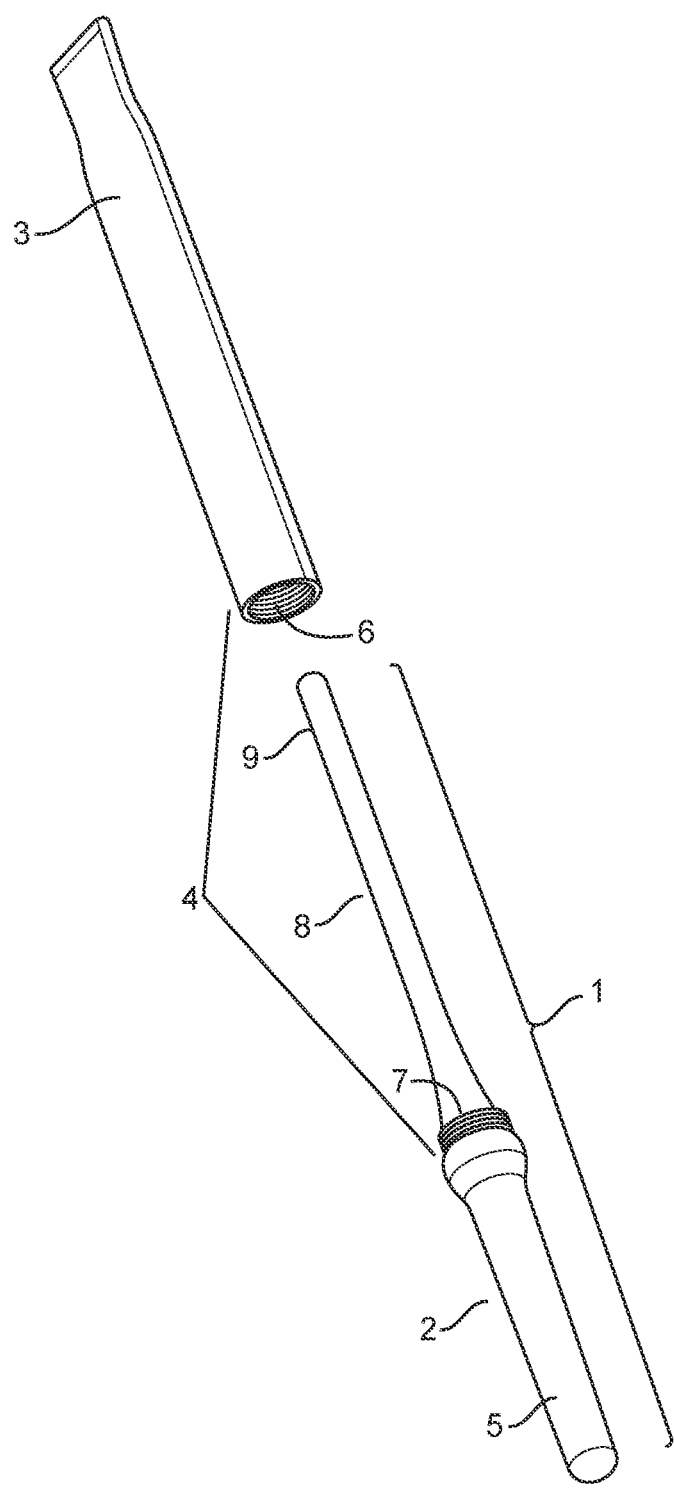
FIG. 3 is a different exploded perspective view of an illustrative device described herein, where cover 3 and applicator 1 are separated from each other to create a broken engagement 4.
Figure 4:
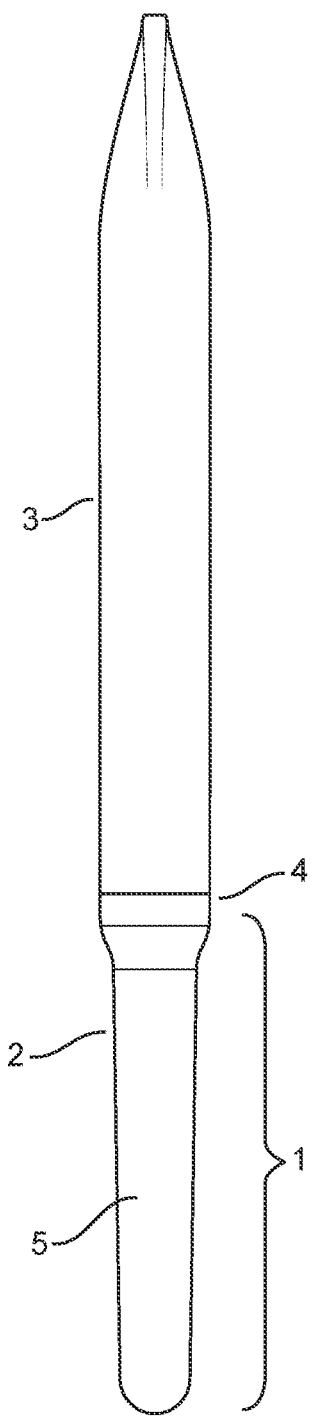
FIG. 4 is a side view of an illustrative device described herein.
Figure 5:
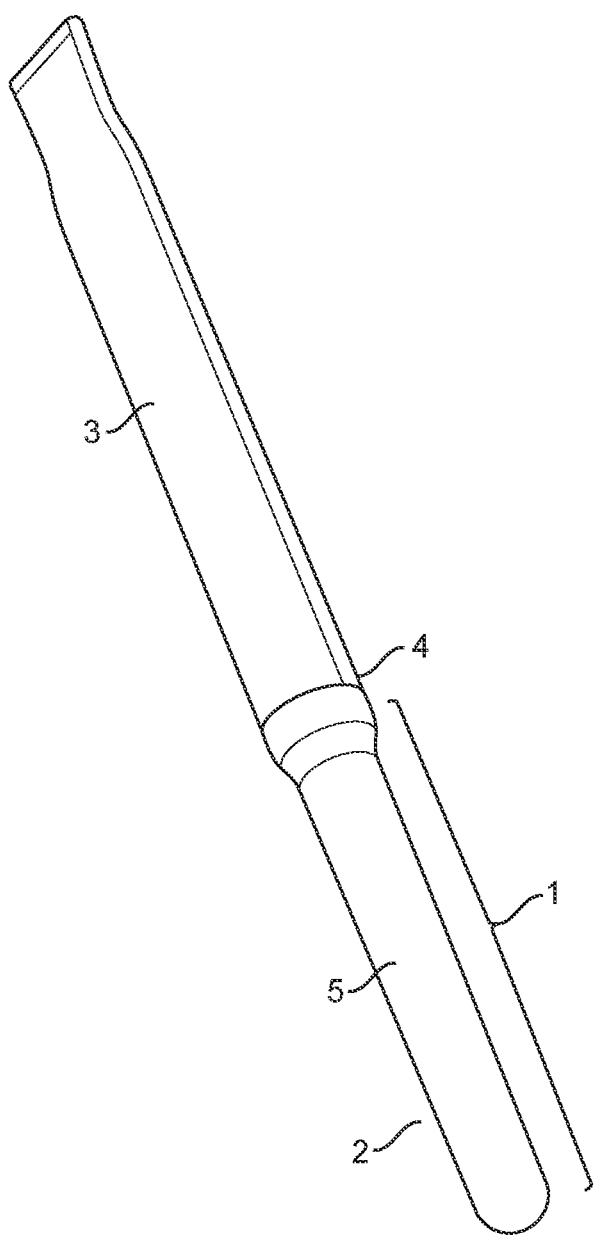
FIG. 5 is a top perspective view of an illustrative device described herein.
Figure 6:
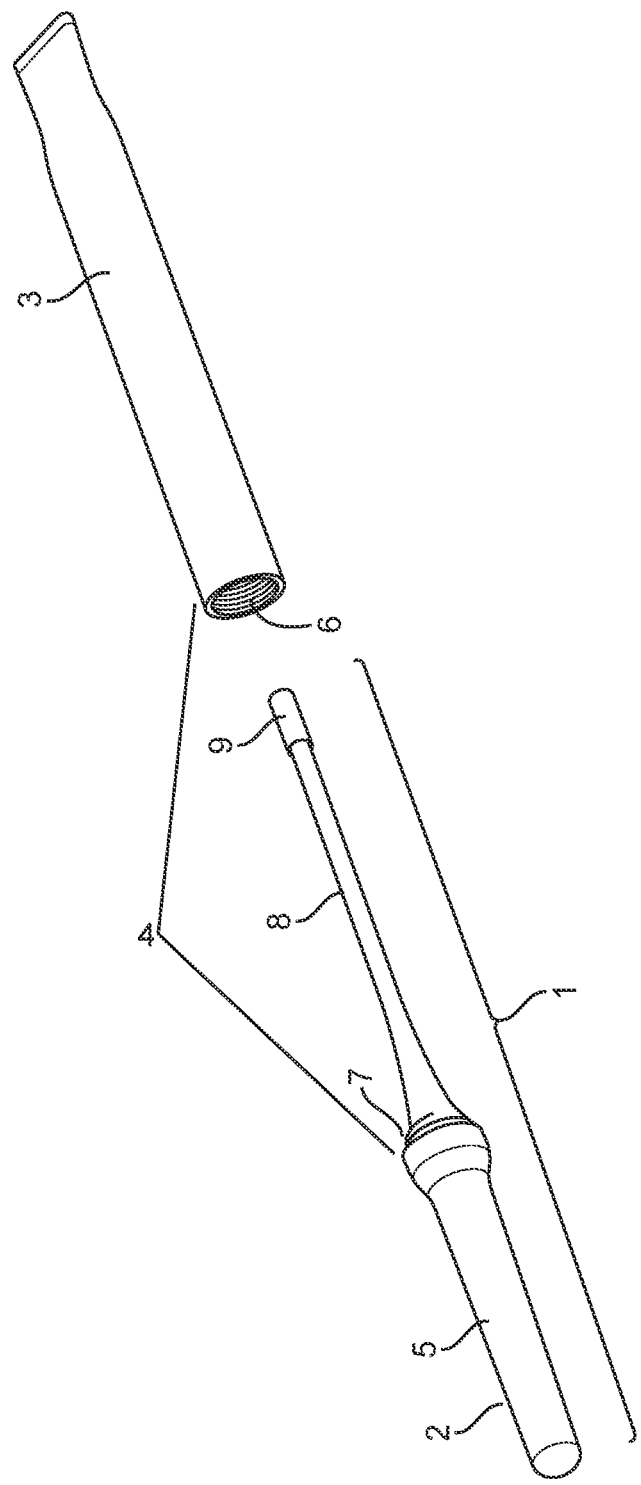
FIG. 6 is a top perspective view of an alternate embodiment of an illustrative device described herein, where a roller assembly in the form of a roller-ball is depicted and the cover 3 and the applicator 1 are separated to create a broken engagement 4.
Figure 7:
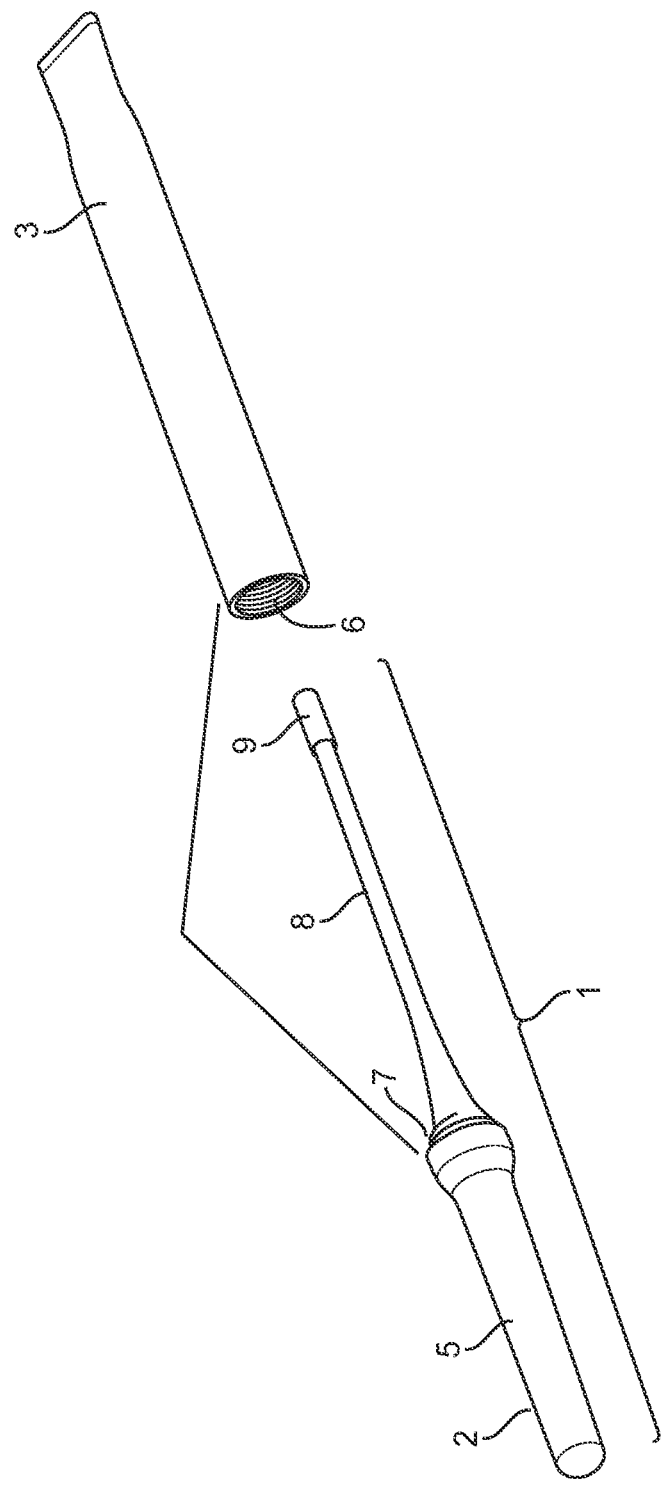
FIG. 7 is an alternate top perspective view of an alternate embodiment of an illustrative device described herein, where the roller assembly in the form of a roller-ball is depicted and cover 3 and applicator 1 are separated to create a broken engagement 4.

While preferred embodiments of the present disclosure have been shown and described herein, it will be obvious to those skilled in the art that such embodiments are provided by ways of example only. Numerous variations, changes, and substitutions will now occur to those skilled in the art without departing from the disclosure. It should be understood that various alternatives to the embodiments of the disclosure described herein can be employed in practicing the disclosure. It is intended that the following claims define the scope of the disclosure and that methods and structures within the scope of these claims and their equivalents be covered thereby.

Described herein, in some embodiments, are devices for delivering pharmaceutical compositions to an individual in need thereof. In some cases, the device comprises an applicator, a cover, and a pharmaceutical composition. In some cases, the applicator delivers the pharmaceutical composition to the individual. In some cases, the pharmaceutical composition comprises a naloxone containing formulation. In some embodiments, the naloxone containing formulation can be held by a surface of the applicator and positioned on the surface of the applicator so that when the device is inserted into the nasal passage or nasal cavity of the individual, the naloxone containing formulations are transmitted to the surface of the nasal passage or nasal cavity by directly contacting the applicator surface with the surface of the nasal passage or nasal cavity. In some cases, the cover can be connected to the applicators by an engagement. In some cases, the engagement can be threaded engagement. In some embodiments, the engagement can be sliding engagement, where the cover can be disconnected from the applicator by sliding the cover away from the applicator. In some embodiments, the engagement comprises a frangible connection, where the frangible connection is broken or disconnected when the cover is disconnected, separated, or removed from the applicator. In some cases, the frangible connection can be broken by tearing, peeling, or pulling the cover away from the applicator. In some embodiments, the cover comprises a seal. In some instances, the seal can be hermetic seals. In some embodiments, the device comprises at least one reservoir for storing the pharmaceutical compositions. In some embodiments, the reservoirs can be part of the cover or part of the applicator. In some embodiments, the reservoir can be both part of the cover and part of the applicator.

In some embodiments, the applicator comprises a nasal trumpet with a conical shape that is curved along its longitudinal axis so that it conforms to the anatomy of the nasal passage. In some cases, the applicator comprises a swab that is positioned on a tip of the applicator. In some embodiments, the applicator tip comprises a roller-ball or a roll-on. In some embodiments, the surface of the applicators that holds the naloxone containing formulation is the surface of the roller-ball. In some embodiments, the applicator tip can be movable or rotatable relative to the applicator and is configured to be manually advanced relative to the applicator, and wherein the surface of the applicator which holds the naloxone containing formulation is a surface of the applicator tip. In some embodiments, the applicator tip is configured to move relative to the applicator when the applicator is rotated relative to the applicator tip. In some embodiments, the applicator comprises a shaft or a stick. In some instances, the applicator can be removable or releasable from the cover. In some embodiments, the tip of the applicator can be removed on the shaft of the applicator. In some embodiments, the applicator can be pre-loaded with the naloxone containing formulation. In some embodiments, the applicator can be loaded with the naloxone containing formulation when the applicator is removed from the cover. In some embodiments, the applicator can be loaded with the naloxone containing formulation by the individual using the device.

In some embodiments, the naloxone containing formulation comprises naloxone hydrochloride. In some instances, the naloxone containing formulation comprises a viscosity between about 0.01 centipoise to about 1,000,000 centipoise at 20 degrees Celsius. In some cases, the naloxone containing formulation comprises a solvent. In some embodiments, the naloxone containing formulation comprises any one of or any combination of the following: at least one tonicity agent; at least one preservative; at least one chelating agent, at least one stabilizing agent; at least one thickening agent; at least one thinning agent; at least one surfactant; at least one excipient; at least one penetration enhancer; at least one thermal regulator; at least one humidity regulator; or at least one additional active ingredient that is not an opioid antagonist. In some embodiments, the naloxone containing formulations can be aqueous formulations, powder formulations, gel formulations, semi-solid formulations, solid formulations, or a combination thereof.

Described herein, in some embodiments, are methods for delivering a pharmaceutical composition to an individual in need thereof. In some cases, the method comprises delivering the pharmaceutical composition to nasal passage or nasal cavity of the individual in need thereof. In some cases, the pharmaceutical composition comprises naloxone containing formulations. In some embodiments, the method of delivering the naloxone containing formulations comprises using the devices as described in the instant disclosure. In some cases, the method comprises: receiving a device comprising an applicator, a cover, and a naloxone containing formulation, where the naloxone containing formulation is held by a surface of the applicator; and inserting the device into the nasal passage of the individual so that the surface of the applicator upon which the naloxone containing formulation is held contacts a surface of the nasal passage. In some cases, the method of delivering the naloxone containing formulations with the devices does not include an injection motion of the devices. In some cases, the method of delivering the naloxone containing formulations with devices described herein comprises contacting the applicators of the devices to the nasal cavity directly. In some embodiments, the method of delivering the naloxone containing formulations with the devices described herein comprises manually inserting and rotating the applicator in the nasal cavity of the individual.

Definitions

Use of absolute or sequential terms, for example, "will", "will not", "shall", "shall not", "must", "must not", "first", "initially", "next", "subsequently", "before", "after," "lastly", and "finally" are not meant to limit scope of the present embodiments disclosed herein but as illustrative.

As used herein, the singular forms "a", "an", and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

Any systems, methods, software, platforms, components of an apparatus described herein are modular and not limited to sequential steps. Accordingly, terms such as "first" and "second" do not necessarily imply priority, order of importance, or order of acts.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

The term "increased" or "increase" as used herein generally means an increase by a statically significant amount. In some embodiments, the terms "increased" or "increase," mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, standard, or control. Other examples of "increase" include an increase of at least 2-fold, at least 5-fold, at least 10-fold, at least 20-fold, at least 50-fold, at least 100-fold, at least 1000-fold or more as compared to a reference level.

The term "decreased" or "decrease" as used herein generally means a decrease by a statistically significant amount. In some embodiments, "decreased" or "decrease" means a reduction by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference level), or any decrease between 10-100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without suffering from opioid overdose or individual being treated for opioid overdose with methods or apparatus that are not described in the instant disclosure.

The terms "patient", "subject", and "individual" are used interchangeably in the present disclosure and encompass mammals. Non-limiting examples of mammal include, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human. In some cases, the individual can be treated with the pharmaceutical composition as described in the present disclosure for opioid overdose or symptoms stemmed from opioid overdose. In some instances, the individual can be the person using the devices and methods described herein to treat another individual who is suffering from opioid overdose.

The term "nasal cavity" or "nasal passage" can be used interchangeably and can include external naris, inferior nasal choncha, middle nasal concha, superior nasal concha, frontal sinus, sphenoid sinus, internal naris, and nasopharynx. Nasal passage or nasal cavity can include epithelium or mucosal lining of any portion of the nasal cavity or nasal passage including, for example, the external naris, the inferior nasal choncha, the middle nasal concha, the superior nasal concha, the frontal sinus, the sphenoid sinus, the internal naris, and the nasopharynx. In some cases, nasal passage or nasal cavity can encompass intranasal blood vessels.

The term "pharmaceutical composition" or "pharmaceutical formulation" can mean a mixture of substances and compounds disclosed herein with at least one active ingredient. The pharmaceutical composition can increase absorption or pharmacokinetics of administration of the active ingredient to the individual in need thereof. In some cases, the pharmaceutical composition can comprise an active ingredient that is an opioid antagonist. In some cases, the pharmaceutical composition can comprise an active ingredient that is naloxone. In some cases, the pharmaceutical composition can comprise an active ingredient that is naloxone hydrochloride (HCl). In some embodiments, the pharmaceutical composition or pharmaceutical formulation is a naloxone containing formulation. In some cases, the pharmaceutical composition can comprise at least two active ingredients. In some cases, the at least two active ingredients can comprise naloxone and at least one additional active ingredient. In some embodiments, the pharmaceutical composition comprising the combination of naloxone with at least one additional active ingredient can increase bioavailability of naloxone in an individual compared to a when the individual is administered with a pharmaceutical composition comprising naloxone as the only active ingredient. In some cases, the pharmaceutical composition comprising naloxone and at least one additional active ingredient can extend the duration of the therapeutic effects of naloxone and/or the at least one additional active ingredient. In some instances, the at least one additional active ingredient that can be combined in a pharmaceutical composition with naloxone can be any of the active ingredients described herein. In some embodiments, the pharmaceutical composition can comprise a combination of naloxone and naltrexone.

The term "active ingredient", "active agent", "therapeutic ingredient", or "therapeutic agent" can refer to substances or compounds that confer therapeutic properties to the pharmaceutical compositions. In some cases, the active or therapeutic agent can comprise opioid antagonists. In some instances, the active or therapeutic agent can comprise agents that can be delivered intranasally. In some embodiments, the active or therapeutic agent that can be delivered intranasally can comprise naloxone. In some embodiments, the active or therapeutic agent that can be delivered intranasally can comprise naloxone HCl. In some embodiments, the active or therapeutic agent that can be delivered intranasally can be agents other than opioid antagonists. Examples of the active or therapeutic agents that can be delivered intranasally include azelastine hydrochloride, beclomethasone dipropionate, budesonide, ciclesonide, cromolyn sodium, flunisolide hemihydrate, fluticasone furoate, calcitonin (salmon, triamcinolone acetonide, ipratropium Bromide, desmopressin, zolmitriptan, dihydroergotamine mesylate, fentanyl citrate, esketamine, oxymetazoline hydrochloride, midazolam, phenylephrine, propylhexedrine, tetrahydrozoline hydrochloride, mometasone furoate monohydrate, olopatadine hydrochloride, and naphazoline In some embodiments, the active or therapeutic agents comprise agents that modulate respiration, cardiac function, circulation, or functions of nerve systems. In some embodiments, the active or therapeutic agents comprise agents that increase respiration, cardiac function, circulation, or functions of nerve systems. In some embodiments, the active or therapeutic agents comprise agents that decrease respiration, cardiac function, circulation, or functions of nerve systems.

The term "opioid antagonist" can mean any pharmaceutically active agent that binds to opioid receptors at higher affinities than opioid agonists, where the binding of opioid antagonists do not active the opioid receptors. Illustrative opioid antagonists can include naloxone, naloxone hydrochloride (naloxone HCl), naloxol, naloxegol oxalate, naloxazone, naltrexone, naltrexone HCl, nalmefene, nalmefene HCl, diprenorphine, nalorphine, nalorphine dinicotinate, levallorphan, samidorphan, nalodeine, 6β-naltrexol, 6α-hydroxynaltrexone, α-chlornaltrexamine, chlorocinnamoylaminodihydronormorphinone, axelopran, bevenopran, methylsamidorphan, nalfurafine hydrochloride, naldemedine, naltrindole hydrochloride, 6'-guanidinonaltrindole dihydrochloride, naltriben mesylate, nalorphine hydrochloride, diacetylnalorphine, naloxonazine dihydrochloride, norbinaltorphimine dihydrochloride, binaltorphimine, levellorphan tartarate, cyprodime, oxilorphan, 3-carboxamido-4-hydroxynaltrexone, cyclazocine, flumazenil, and naldemedine.

The term "opioid overdose", as used herein, is induced by excessive use of opioids. Symptoms of opioid overdose can include depressions or decreases of respiration, cardiovascular function, circulation, or functions of nerve systems. In some cases, the individual suffering from opioid overdose is not fully conscious.

The term "therapeutically effective amount" as used herein relates to an amount of active or therapeutic agent, delivered to the individual that elicits a medicinal response to opioid overdose in the individual. In some embodiments, the therapeutically effective amounts can be at least partially determined by median effective dose ($ED_{50}$) or effective dose required to achieve the desired effect in 95% of a population ($ED_{95}$).

The term "pharmacokinetics" can refer to absorption and distribution of the pharmaceutical compositions that have been administered to an individual. In some cases, pharmacokinetics can be at least partially determined based on a combination of any one of area under the curve (AUC), C max, T max, dose, dose interval, concentration, volume of distribution, elimination half-life, elimination rate constant, clearance, bioavailability, or fluctuation.

The term "solvent" relates to any substances or compounds that dissolve a solute. In some cases, the solutes comprise the active or therapeutic agents as described herein. Non-limiting examples of solvents can include, but are not limited to, water, buffered solutions, other aqueous solutions, alcohols (e.g., ethanol, methanol, butanol), and mixtures thereof that optionally include other components such as pharmaceutical excipients, polymers, salts, preservatives, viscosity modifiers, tonicity agents, taste masking agents, antioxidants, pH modifier, or a combination thereof. In other embodiments, an organic solvent can be used.

The term "excipient" or "pharmaceutically acceptable carrier" refers to substances or compounds formulated in conjunction with the active ingredient of the pharmaceutical compositions. Inclusion of excipients can increase long-term stabilization or storage, increase the physical size of the pharmaceutical formulations as fillers, diluents, or bulking agents, or enhance absorption of the active ingredient of the pharmaceutical formulation. In some instances, excipients can be used during manufacturing of the pharmaceutical compositions.

The term "tonicity agent", as described herein, can refer to substances or compounds that modify or maintain osmolality of the pharmaceutical composition. The tonicity agents can modify the pharmaceutical composition to be hypotonic, isotonic, or hypertonic. In some embodiments, the tonic agents can be hypotonic agents, isotonic agents, or hypertonic agents. Illustrative tonicity agents include: sugar such as dextrose, lactose, sorbitol, sucrose, mannitol, trehalose, raffinose, and hydroxyethyl starch; and salt such as sodium chloride, calcium chloride, and magnesium chloride. Tonicity agents can also be polyethylene glycol or glycine.

The term "surfactant" refers to substances or compounds that decrease surface tension. Surfactants can be detergents, wetting agents, emulsifiers, foaming agents, or dispersants. In some cases, the surfactants can be anionic, cationic, zwitterionic, or non-ionic. Illustrative surfactants that can be formulated as part of the pharmaceutical compositions as described in the present disclosure include sulfate, sulfonate, phosphate, carboxylates, ammonium lauryl sulfate, sodium lauryl sulfate (sodium dodecyl sulfate, SLS, or SDS), alkyl-ether sulfates sodium laureth sulfate (sodium lauryl ether sulfate or SLES), sodium myreth sulfate, docusate (dioctyl sodium sulfosuccinate), perfluorooctanesulfonate (PFOS), perfluorobutanesulfonate, alkyl-aryl ether phosphates, alkyl ether phosphates, carboxylate salts (soaps) such as sodium stearate, sodium lauroyl sarcosinate, carboxylate-based fluorosurfactants such as perfluorononanoate or perfluorooctanoate (PFOA or PFO), octenidine dihydrochloride, cetrimonium bromide (CTAB), cetylpyridinium chloride (CPC), benzalkonium chloride (BAC), benzethonium chloride (BZT), dimethyldioctadecylammonium chloride, dioctadecyldimethylammonium bromide (DODAB), CHAPS (3-[(3-cholamidopropyl)dimethylammonio]-1-propane-sulfonate), cocamidopropyl hydroxysultaine, cocamidopropyl betaine, phospholipids phosphatidylserine, phosphatidylethanolamine, phosphatidylcholine, sphingomyelins, ethoxylates, octaethylene glycol monododecyl ether, pentaethylene glycol monododecyl ether, nonoxynols, Triton X-100, polyethoxylated tallow amine, cocamide monoethanolamine, cocamide diethanolamine, sorbitan monolaurate, sorbitan monostearate, sorbitan tristearate, Tween, decyl glucoside, lauryl glucoside, octyl glucoside, lauryldimethylamine oxide, dimethyl sulfoxide, or phosphine oxide.

The term "chelating agent" means substances or compounds that react with metal ions, forming a stable and water-soluble complex. Chelating agents can also be referred to as chelants, chelators, or sequestering agents. Illustrative chelating agents that can be formulated as part of the pharmaceutical compositions include dimercaprol, penicillamine, trientine, Zinc, deferasirox, deferiprone, deferoxamine, EDTA, EGTA, and succimer.

The term "stabilizing agent" refers to substances or compounds that decrease or prevent degradation of the active ingredient of the pharmaceutical compositions. In some cases, the stabilizing agents can be antioxidants, chelating agents, or polymers that protect against ultraviolet (UV) light. In some cases, the stabilizing agent can be emulsifiers or surfactants. In some embodiments, the stabilizing agent can be thickening agent, thinning agent, or gelling agent. Examples of stabilizing agents include, but are not limited to: glycerol, methionine, monothioglycerol, EDTA, ascorbic acid, polysorbate 80, polysorbate 20, arginine, heparin, dextran sulfate, cyclodextrins, pentosan polysulfate and other heparinoids, divalent cations such as magnesium and zinc, or combinations thereof.

The term "preservative" can refer to a pharmaceutically active agent with antimicrobial properties, where preservative can be added to pharmaceutical compositions to prevent propagation or activities of microbes in the pharmaceutical composition. In some cases, the preservative can maintain the sterility of the pharmaceutical composition.

The term "penetration enhancer" as disclosed herein, can mean an agent which increases absorption of the active ingredient in the pharmaceutical composition through nasal mucosal membrane. In some cases, the penetration enhancer increases absorption of the opioid antagonist by nasal mucosal membrane.

The term "thickening agent" or "thinning agent" refers to substances or compounds that increase or decrease viscosity of the pharmaceutical compositions. In some embodiments, the thickening agent can be polysaccharide such as hydroxypropyl methylcellulose (HPMC), hydroxypropyl cellulose, methyl cellulose, carboxymethylcellulose calcium, sodium carboxymethylcellulose, sodium alginate, xanthan gum, acacia, guar gum, locust bean gum, gum tragacanth, starch, carbopols, methylcellulose, polyvinylpyrrolidone, or a combination thereof. In some embodiments, the thinning agent can be maltose, maltodextrin, lactose, fructose, dextrin, microcrystalline cellulose, starch, sorbitol, sucrose, silicate microcrystalline, cellulose, dextrates, copovidone, mannitol, glucose, calcium phosphate, or a combinations thereof.

The term "gelling agent" refers to hydrophobic or hydrophilic substances or compounds that thicken an aqueous pharmaceutical composition into a gallant form of a pharmaceutical composition. In some cases, gelling agent can be a thickening agent. Non-limiting examples of a hydrophobic gelling agent comprises a liquid paraffin with polyethylene or fatty oils gelled with colloidal silica, or aluminum or zinc soaps. Non-limiting examples of a hydrophilic gelling agent include tragacanth, starch, cellulose derivatives, carboxyvinylpolymers, and magnesium-aluminum silicates.

"Device" as used herein, refers to an apparatus configured to deliver pharmaceutical compositions to an individual in need thereof. In some embodiments, the device comprises an applicator configured for delivering pharmaceutical compositions to an individual. In some cases, the applicator can deliver pharmaceutical compositions by directly contacting pharmaceutical composition to the nasal passage or nasal cavity of the individual. In some cases, the applicator can deliver pharmaceutical compositions via a mechanism that does not include an injection motion of the applicator nor the device. In some cases, the applicator can deliver the pharmaceutical composition by directly contacting the applicator to the nasal cavity or nasal passage of the individual. In some embodiments, the direct contact can comprise inserting or rotating the applicator inside the nasal passage or nasal cavity of the individual. In some embodiments, the device can comprise a cover. In some cases, the cover prevents exposure of the applicator to environment. In some embodiments, the cover prevents delivery of the naloxone containing formulation prior to the cover being removed from the device. In some embodiments, the device can be used by healthcare professionals such as doctors, nurses, and emergency medical technicians to deliver pharmaceutical compositions. In some instances, the device can be used by individuals without training or healthcare backgrounds to deliver pharmaceutical compositions. In some embodiments, the device can be operated by only one hand. In some embodiments, the device can be used by healthcare professionals such as doctors, nurses, and emergency medical technicians to deliver naloxone containing compositions. In some instances, the device can be used by individuals without training or healthcare backgrounds to deliver naloxone containing compositions. In some embodiments, the device can be operated by only one hand to deliver naloxone containing formulation. In some embodiments, once inserted the device delivers the naloxone containing formulation without additional manual manipulation such as injection or a motion that mimics injection of the applicator or the device. Illustrative material that can be used to manufacture the devices include polyethylene, polypropylene, polyoxy methylene, rubber, elastomer, glass, stainless steel, or aluminum.

"Cover" as described in the instant application pertains to parts of the devices that, prior to removal from the rest of the devices, prevents delivery of the pharmaceutical compositions by the applicators to the nasal passage or nasal cavity. In some embodiments, the cover can be at least partially removed from the device to expose the applicators. In some embodiments, the cover comprises a seal such as a hermetic seal. In some embodiments, the cover comprises a reservoir for storing the pharmaceutical composition. In some embodiments, the cover comprises a reservoir for storing the naloxone containing composition. In some embodiments, the cover comprises a part of an engagement to be engaged with the engagement of the applicator. In some cases, the engagement can be reversibly or irreversibly broken or separated by removing the cover to at least partially expose the applicator.

"Applicator" refers to the parts of the device that, after removal of the cover, delivers pharmaceutical composition to the individual in need thereof. In some embodiments, the applicator delivers the pharmaceutical composition to the nasal passage or nasal cavity of the individual. In some embodiment, the applicator delivers the pharmaceutical compositions by direct contact between the applicator and the nasal passage or nasal cavity. In some embodiment, the applicator delivers the naloxone containing composition by direct contact between the applicator and the nasal cavity. In some embodiments, the applicator comprises a seal such as a hermetic seal. In some embodiments, the applicator comprises a reservoir for storing the pharmaceutical compositions. In some embodiments, the applicator comprises a reservoir for storing the naloxone containing compositions. In some embodiments, the applicators comprises a part of the engagement that can be engaged with the engagement of the cover. In some cases, the engagement can be reversibly or irreversibly broken by removing the cover to at least partially expose the applicator.

Devices

In reference to FIG. 1-23, the present disclosure directs to an intranasal delivery device. The intranasal delivery device aims to provide a simplified, portable, cost-effective means of delivering medicant or pharmaceutical compositions to an individual via the nasal cavity. In some embodiments, the pharmaceutical computations comprise a naloxone containing formulation. It is contemplated that the intranasal delivery apparatus can feature tamper-safe construction as a feature of the particular construction described herein. These features will further include simplified, single-use hermetic seals separating the internally stored medicant or pharmaceutical compositions from external contamination or degradation. The specific structures related to these functions are understood to increase shelf-life, decrease manufacturing costs, and enable any user to be confident that their tools will remain suitably potent to treat an overdosing individual.

The intranasal delivery apparatus comprises a cover and an applicator in the ideal embodiment of the present disclosure, ideally separable prior to use such that a medication or pharmaceutical compositions can be dispensed from the applicator. All aspects related to the material of the casing of the device, the covers, or the applicators are to be contemplated within the scope of the present disclosure, including all stipulations or recommendations extended by local administrative authorities or industry best-practices. In various embodiments, the casing of the devices constitutes a reinforced storage vessel containing any variety of medicant or pharmaceutical compositions in pre-metered dosages. In combination with the applicator, the casing of the device will additionally feature a series of frangible connections constituting portions of the anti-tamper features referenced above. These anti-tamper or tamper-evident properties are related to the detachment of the applicator from said casing but are considered to not significantly impede the removal and deployment of the applicator in any embodiment. This removal process will ideally permanently sever or otherwise deform a series of frangible components arranged about the connection between the applicator and the cover, indicating that the medication contained therein is to be considered unsuitable for use (apart from the intentional removal of the applicator for immediate use).

In some embodiments, the applicator comprises a handle or haft, a cap or a cover, a plurality of first threads, a first seal, a shaft, a body of substrate, and a first bond. The haft or handle constitutes a graspable section of material contiguous with the cap, ideally extending substantially outward from conjoined form of the intranasal delivery apparatus when the casing and applicator are fixed together. This haft or handle can define any shape congruent to the human hand or fingers without departing from the original scope of the disclosure including tabs, rings, posts, or other ergonomic shapes. The cap or the cover ideally defines a domed body congruent to the cross-sectional diameter of the casing, suitable to completely enclose at least one end of said casing. The plurality of first threads defines a series of helical machined threads as can be understood in the manufacturing industry generally. This plurality of first threads is ideally proud of the surface of the cap, congruent to and capable of interface with a similar feature of the casing to facilitate attachment between the applicator and the casing. The first seal ideally defines an O-ring aligned with the end of the plurality of first threads, directly adjacent to the cap. In another instance, the first seal can define a similar O-ring that is integral to the plurality of first threads, such that the first seal can be compressed against the inner diameter of the casing when the applicator is stored within the casing. In further alternate embodiments, the first seal can constitute a portion of the plurality of first threads that has been radially molded to the casing such that the first seal must be broken before a user can remove the applicator from the casing. The shaft defines an elongated rod ideally molded into the cap as a single contiguous body, extending outward from the cap opposite the haft. The distal end of the shaft terminates with a body of substrate affixed to the shaft by the first bond. The body of substrate and the first bond are ideally contemplated to define a wad of spun cotton and a chemical adhesive, respectively. However, it is contemplated that the first bond can constitute any other attachment means or associated methods of manufacturing known to any reasonably skilled individual. In this instance, the volume of substrate will constitute an absorbent swap of type and design that can be readily understood in the medical field. In another instance, the volume of substrate constitutes a hollow, cylindrical body rotatably fixed about the shaft. In this instance, the first bond can constitute a rotating sleeve fixed within the volume of substrate or can constitute a terminal pin fixed to the distal end of the shaft such that the volume of substrate remains attached to the shaft. In this configuration, the volume of substrate can rotate about an axis defined by the longest dimension of the shaft in a manner contemplated to more effectively spread medicant on the internal nasal walls. In various alternate embodiments, the volume of substrate is contemplated to be an absorbent carrier for any medicants associated with the intranasal delivery apparatus, facilitating both storage and dispersal of said medicants. The casing comprises a reservoir, a portal, a plurality of second threads, a second seal, a concavity, a volume of compound, a seam, a shell, and a second bond. The reservoir defines a substantially hollow package of suitable scale and dimensions to substantially contain and support the applicator, in addition to any active compounds associated with various embodiments of the present disclosure. The portal defines an open face of the reservoir, enabling direct access to the concavity defined within the reservoir. The plurality of second threads is ideally embossed within the inner diameter of the portal, such that the plurality of first threads associated with the applicator can be intermeshed and fixed therein. The second seal ideally defines an O-ring affixed to the portal, adjacent to the plurality of second threads. Similar to the plurality of first threads and the first seal, it is contemplated that the second seal can be integral to the plurality of second threads such that the insertion of the applicator will hermetically seal the concavity until the applicator is removed for use. The shell defines a rigid, hollow insert fixed within the reservoir opposite the portal. The shell will, in the ideal embodiment of the present disclosure, offer structural support to the body of the casing such that a user can grasp the casing and twist the applicator loose without the casing deforming. It is further contemplated that the shell will provide additional puncture, crush, and shear resistance to the casing, ensuring that the integrity of the concavity is maintained even in adverse use-cases or storage conditions. The shell can additionally prevent the separation of the volume of substrate and the volume of compound during prolonged periods of storage, preventing any loss of potency caused by a reduction of the available volume of compound deliverable to an individual when the intranasal delivery apparatus is eventually deployed. The shell is ideally fixed within the reservoir by the second bond, defined as any known means of permanently fixing a planar material to a rigid body; ideally constituting a non-volatile adhesive known in the medical manufacture industry to be safe for contact with all known forms of medicant. The volume of compound defines the above-referenced medicant, ideally constituting a pre-measured amount of naloxone (or similar opioid antagonist agent) know to be used to treat overdosed individuals. As described, it is contemplated that the volume of compound will be primarily absorbed by and stored within the volume of substrate until administered to an individual via direct contact between the volume of substrate and an individual's nasal walls. It should be understood that the present disclosure can be reasonably adapted to contain and dispense a variety of other compounds, via a variety of other known methods, without departing from the original scope of the disclosure. Given the particular construction of the casing (i.e. the frangible-mounted applicator and the otherwise hermetically sealed casing), it is considered that the volume of compound can be added via a temporary breach in the reservoir. Said breach would ideally be closed by welding the material of the reservoir together, constituting the seam referenced above.

In some embodiments, described herein are devices configured to deliver pharmaceutical compositions to an individual in need thereof. In some embodiments, the pharmaceutical composition comprises a naloxone containing formulations. FIG. 1-23 illustrate various embodiments of the devices as described herein. In some embodiments, the device comprises an applicator 1, a cover 3, and a naloxone containing formulation, where the naloxone containing formulation is held by a surface of the applicator 1 and positioned on the surface of the applicator 1 so that when the device is inserted into the nasal passage of the individual, the naloxone containing formulation is transmitted or delivered to the surface of the nasal passage or nasal cavity via direct contact of the applicator surface with the surface of the nasal passage or nasal cavity. In some embodiments, the device comprises a casing 2. In some cases, the casing 2 is part of the applicator 1. In some cases, the casing 2 is part of the cover 3. In some embodiments, the device comprises a haft or a handle 5. In some embodiments, the handle 5 can be part of the applicator 1.

Figure 11A:
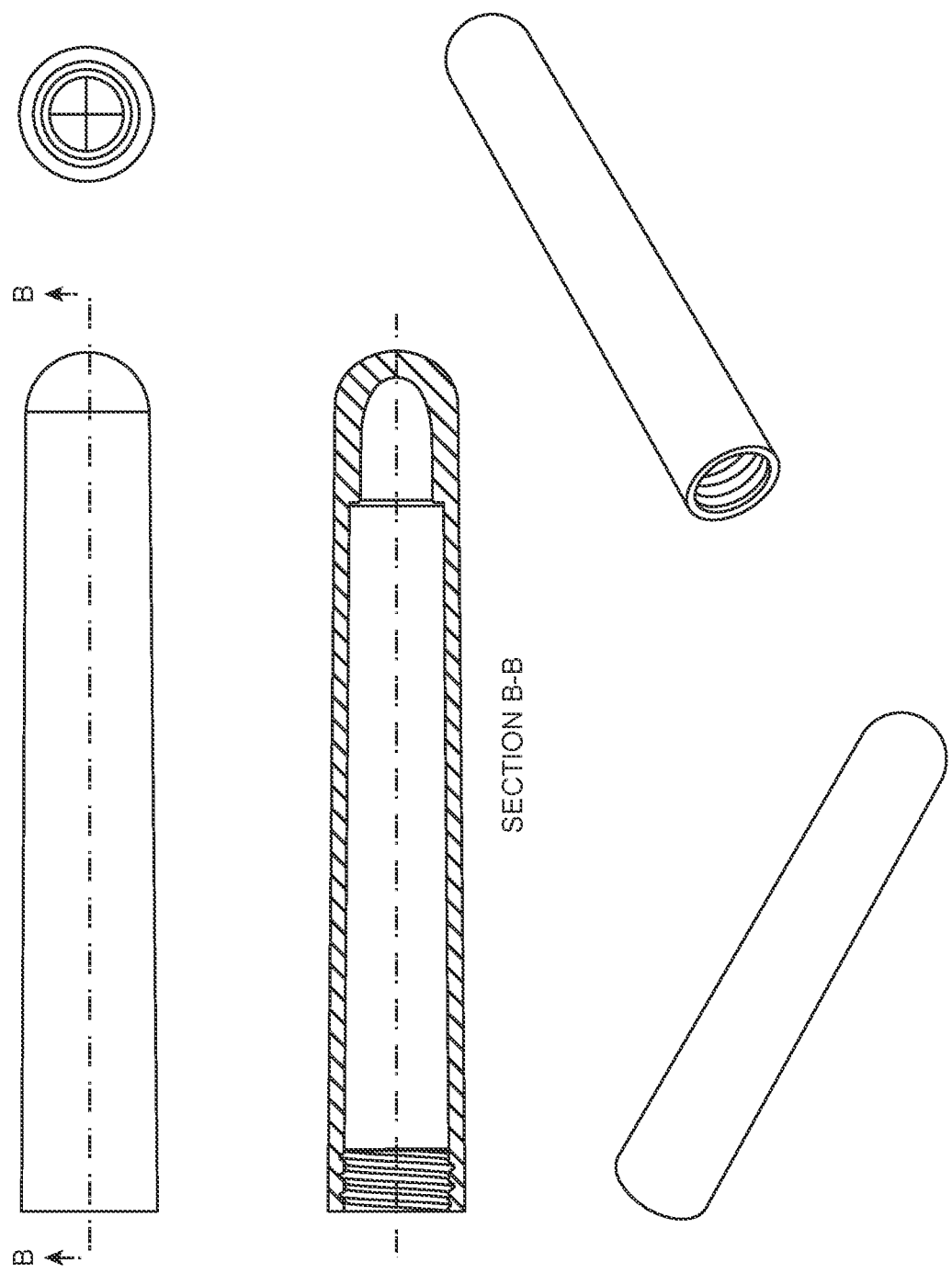
FIG. 11A illustrates the cover of the device as shown in FIG. 10.
Figure 11B:
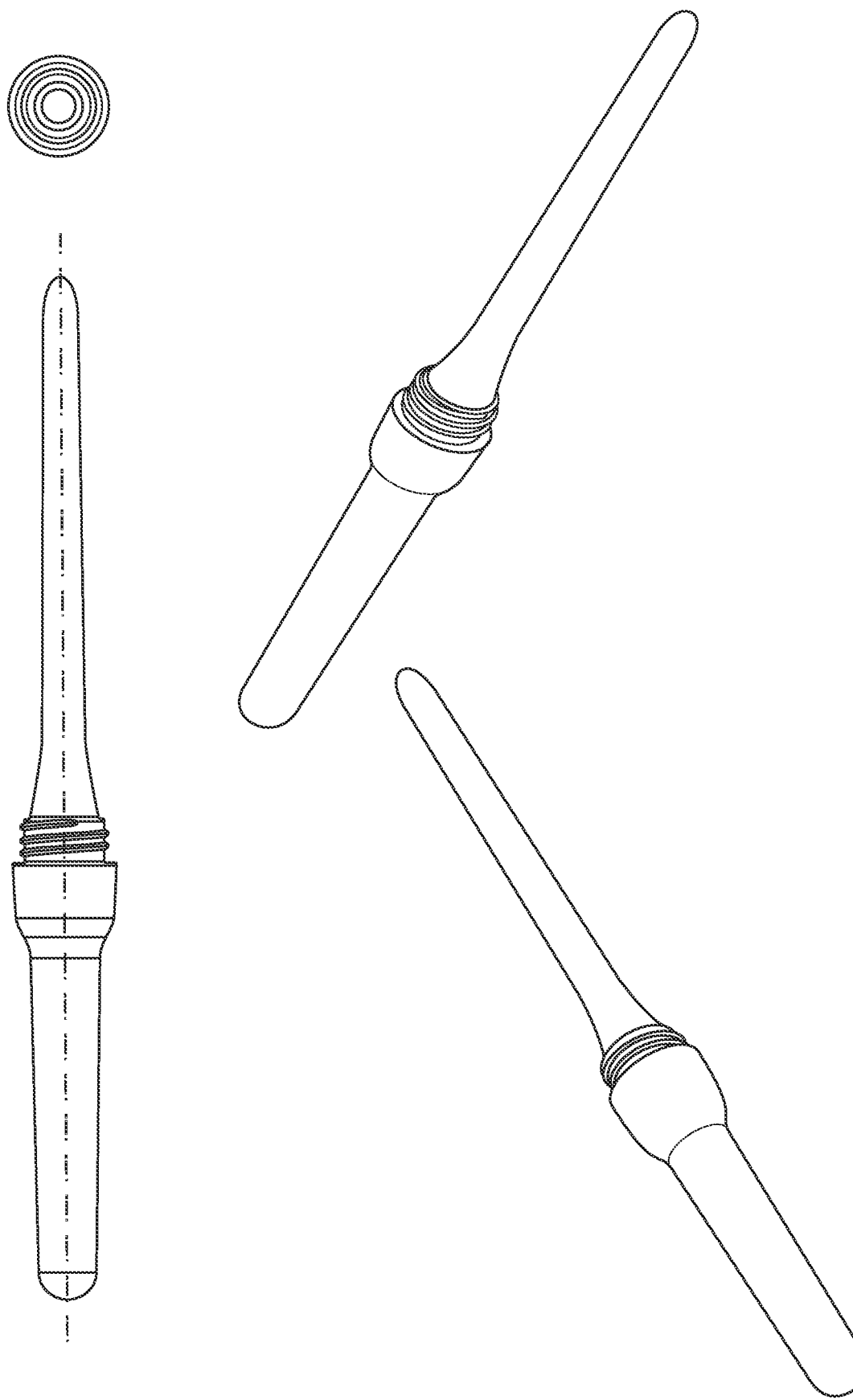
FIG. 11B illustrates the applicator of the device as shown in FIG. 10.

In some embodiments, the applicator 1 and the cover 3 as described herein can be connected by forming an engagement 4 between the applicator 1 and the cover 3. In some cases, the engagement 4 can be formed by connecting first engagement part 6 located on the cover 3 to the second engagement part 7 located on the applicator 1. In some cases, the cover 3 at least partially encapsulates the applicator 1 when the engagement 4 is in an engaged or connected position. In some cases, when the engagement 4 is at least partially broken or disconnected, the cover 3 do not fully encapsulate the applicator 1. In some cases, the applicator 1 can be at least partially exposed when the engagement 4 is broken or disconnected. In some embodiments, the engagement 4 comprises a frangible connection, which can be irreversibly disconnected or broken when the cover 3 is removed from the devices. In some cases, the engagement 4 can be a threaded engagement 10 (e.g. as shown in FIG. 8, FIG. 9, FIG. 10, and FIG. 11A-B), where the first engagement part 6 comprises a first set of threads and the second engagement part 7 comprises a second set of threads to be threaded to the first set of threads. In some instances, as shown in FIG. 10 and FIG. 11A-B, the base of the device can be a rounded base instead of a flattered base. The rounded base can be injection molded. The flattered base can be formed by thermal crimping.

Figure 13:
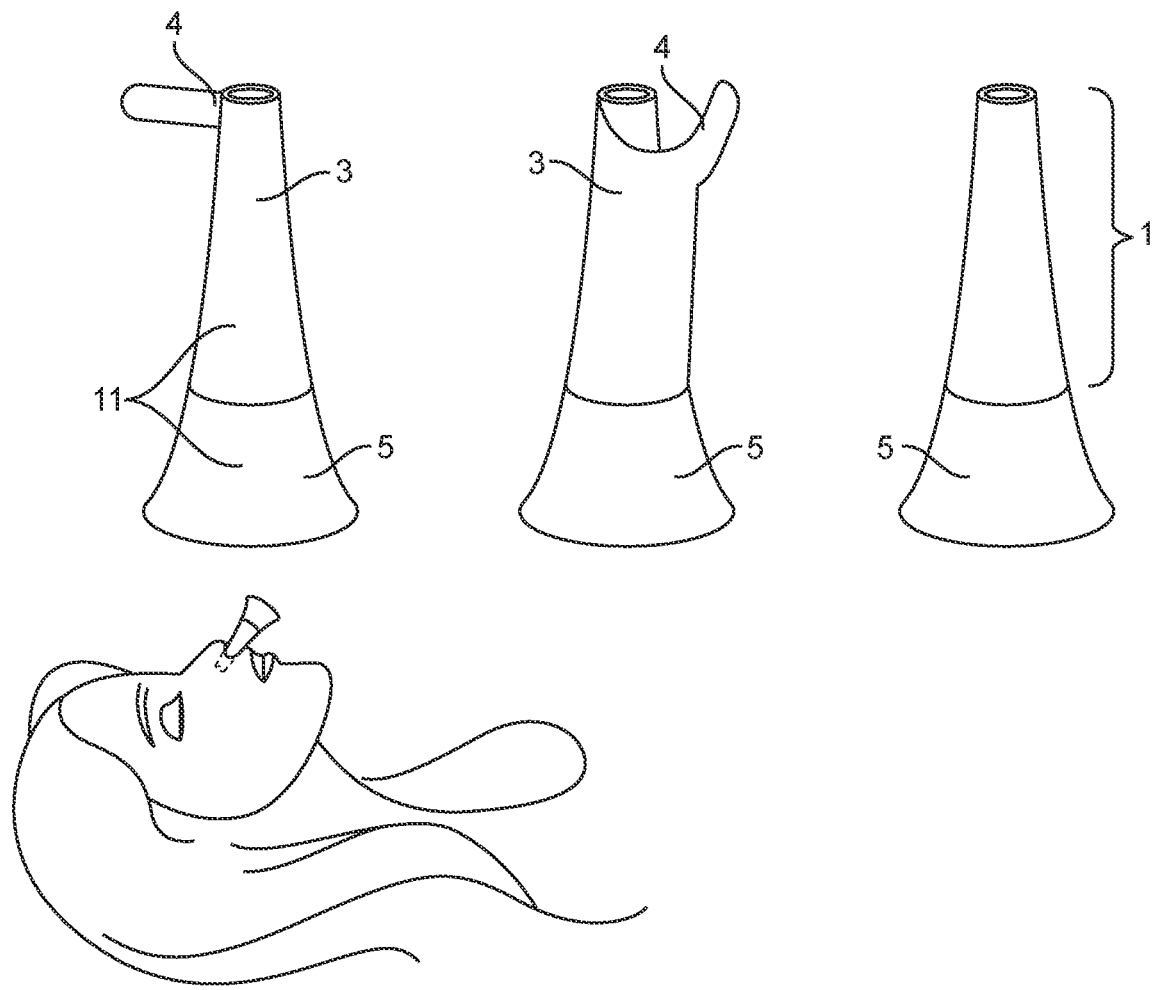
FIG. 13 illustrates the device comprising an applicator in the form a nasal trumpet for delivering a pharmaceutical composition by directly contacting the nasal trumpet to the nasal passage or nasal cavity of an individual who is in need of the pharmaceutical composition, said nasal trumpet comprises a conical shape to conform the anatomy of the nasal passage or nasal cavity.

Upon unscrewing of the cover 3, the threaded engagement 10 is reversibly disconnected and the applicator 1 is at least partially exposed. In some instances, the engagement 4 can be a mechanical engagement, where the first engagement part 6 can be mechanically connected or disconnected from the second engagement part 7 by manually moving the cover 3 or applicator 1. In some embodiments, the mechanical engagement can be a reversible or an irreversible engagement. In some cases, the mechanical engagement is reversibly or irreversibly disconnected by moving the cover 3 away from the applicator 1 along a longitudinal axis of the devices. In some embodiments, the mechanical engagement is reversibly or irreversibly disconnected by moving the cover 3 away from the applicator 1 along a vertical axis of the devices. In some embodiments, the mechanical engagement is reversibly or irreversibly disconnected by moving the cover 3 away from the applicator 1 along a lateral axis of the devices. In some embodiments, the mechanical engagement is reversibly or irreversibly disconnected by moving the cover 3 away from the applicator 1 along a combination of longitudinal, vertical, or lateral axes of the device. In some embodiments, the engagement 4 can be single-handedly reversibly or irreversibly broken or disconnected. In some embodiments, the engagement 4 comprises a frangible connection, where the frangible connection is broken or disconnected when the cover 3 is disconnected, separated, or removed from the applicator 1. In some cases, the frangible connections can be broken by tearing, peeling, or pulling the covers away from the applicators as shown in FIG. 13. In some embodiments, the engagement 4 comprises a threading engagement formed by a first set of threads on the cover 3 and a second set of threads on the applicator 1. In some instances, the engagement 4 comprise a sliding engagement, where the cover 3 can slide towards the applicator 1 to connect or slide away from the applicator 1 to disconnect.

In some embodiments, cover 3, prior to be removed from the rest of the devices, prevents delivery of the pharmaceutical compositions by the applicators to the nasal passage or nasal cavity. In some embodiments, the cover 3 can be at least partially removed from the devices to expose the applicator 1. In some embodiments, the cover 3 comprises seals such as hermetic seals. In some embodiments, the cover 3 comprise a reservoir 11 for storing the pharmaceutical compositions. In some embodiments, the cover 3 comprise a reservoir 11 for storing the naloxone containing compositions.

In some embodiments, applicator 1, after removal of the cover 3, delivers pharmaceutical compositions to the individual in need thereof. In some embodiments, the applicator 1 delivers the pharmaceutical compositions to the nasal passage or nasal cavity of the individual. In some embodiment, the applicator 1 delivers the pharmaceutical compositions by direct contact between the applicator 1 and the nasal passage or nasal cavity. In some embodiment, the applicator 1 delivers the naloxone containing compositions by direct contact between the applicator 1 and the nasal passage or nasal cavity. In some embodiments, the applicator 1 comprises seals such as hermetic seals. In some embodiments, the applicator 1 comprises a reservoir 11 for storing the pharmaceutical compositions. In some embodiments, the applicator 1 comprises a reservoir 11 for storing the naloxone containing compositions.

Figure 8:
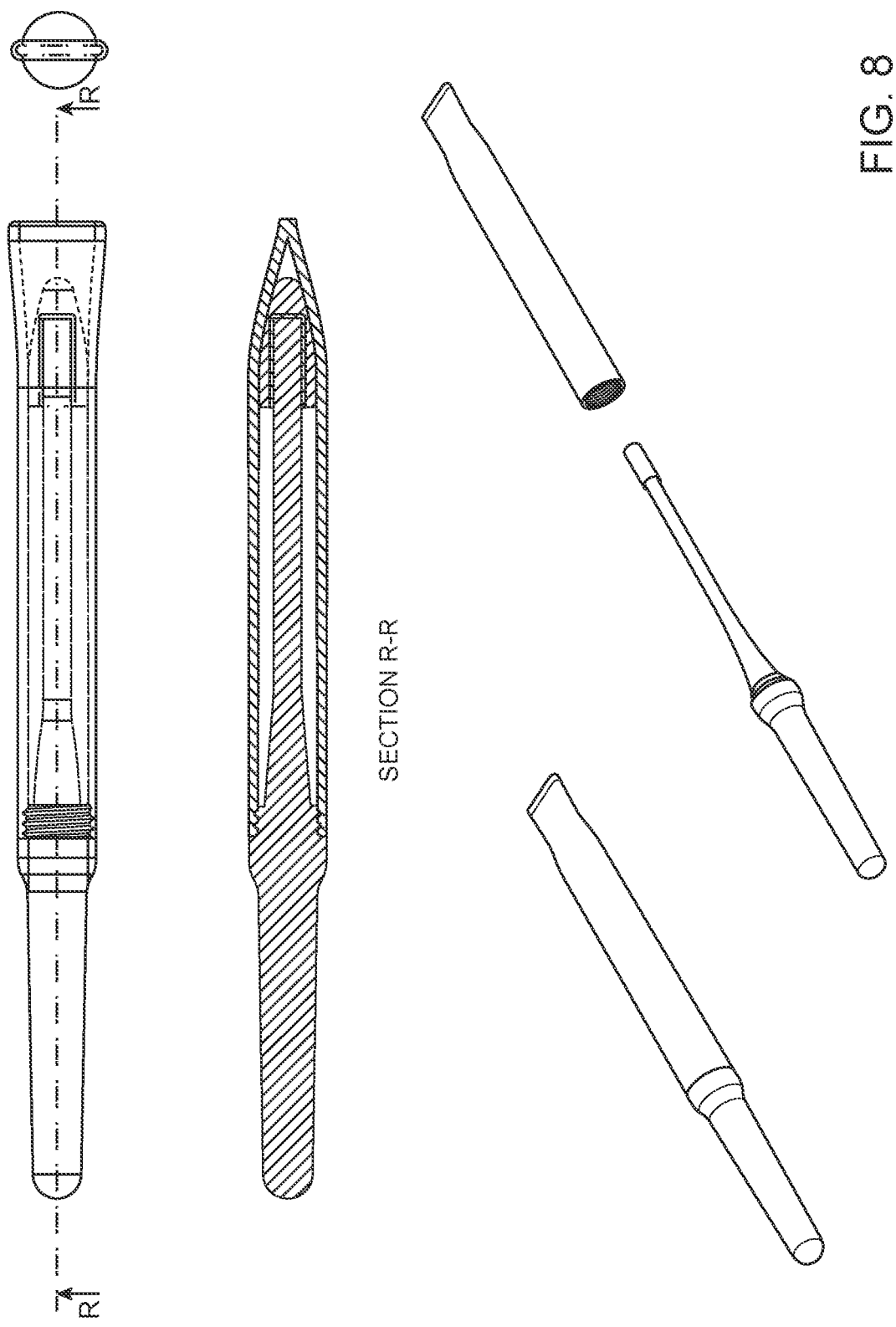
FIG. 8 is a schematic view of an alternate embodiment of an illustrative device described herein, where multiple section and perspective views of the roller assembly in the form of a roller-ball and inner reservoirs are depicted.
Figure 9:
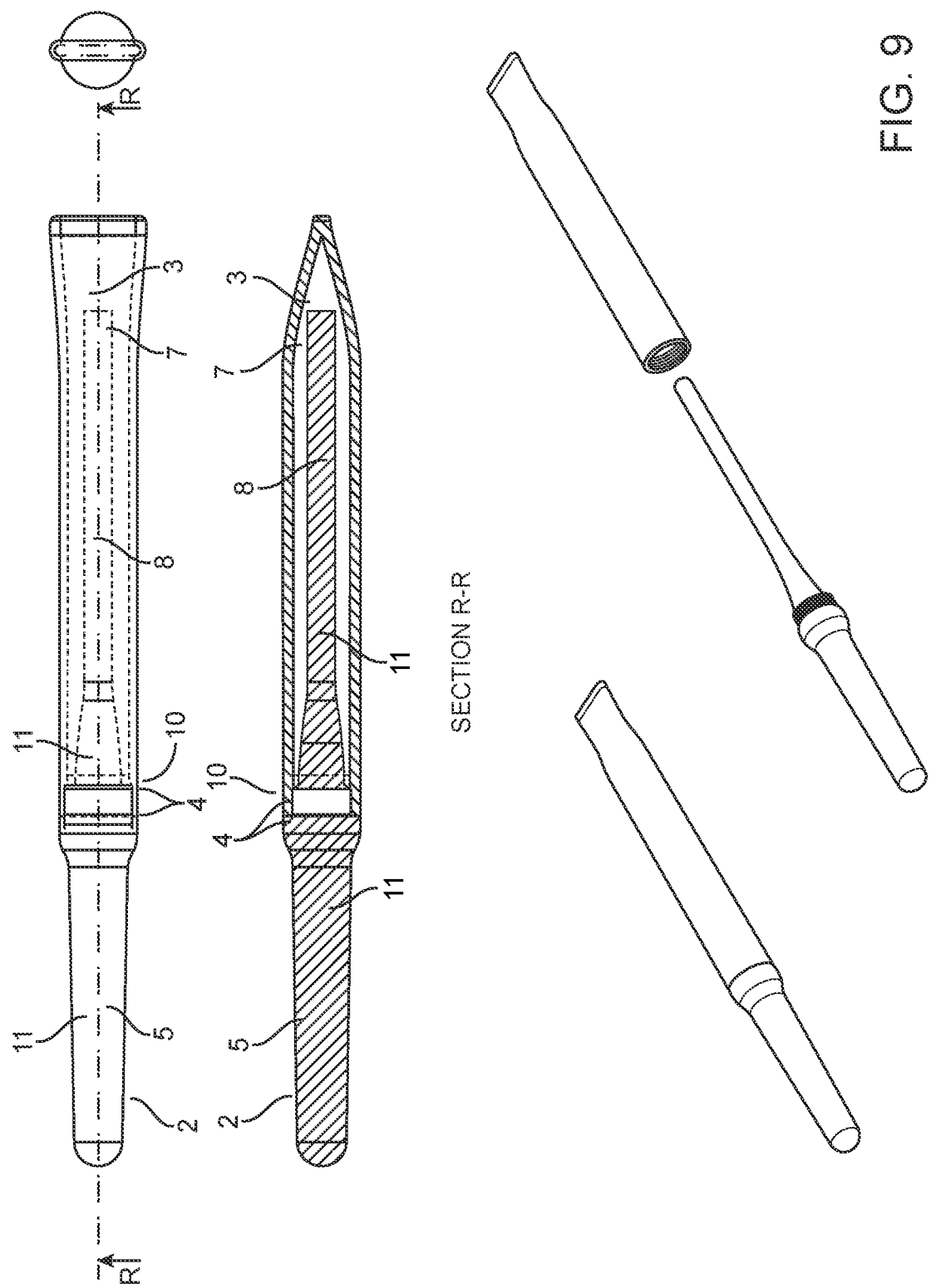
FIG. 9 is a schematic view of an alternate embodiment of an illustrative device described herein, where multiple section and perspective views of the roller assembly in the form of a roller-ball and an inner protective layer are depicted.

In some embodiments, the device described herein can comprise more than one reservoir. In some cases, the device can comprise a reservoir in the applicator and a reservoir in the cover. In some cases, the device can optionally comprise a reservoir that is between the applicator and the cover. As shown in FIG. 8, a second reservoir 11 is between the applicator 1 and the cover 3.

In some embodiments, the applicator 1 comprises a shaft 8 and a tip 9. In some cases, either shaft 8, tip 9, or both shaft 8 and tip 9 are bonded to the cover 3. In some cases, the bond can be an adhesive bond. In some cases, the bond can be broken when cover 3 is removed from applicator 1. In some embodiments, prior to the bond being broken the applicator 1 cannot dispense nor deliver the naloxone containing formulation.

In some embodiments the applicator 1 comprises an extender, where applicator 1 can be extended along a longitudinal axis. In some cases, the extender can slide along the longitudinal axis of the device to extend the applicator. In some cases, the extender comprises a threading engagement where unscrewing or screwing the threads can extend the applicator. In some cases, the applicator 1 comprises mechanical joints or flexible material, where the applicator 1 can be bent before, during, or after delivering the naloxone containing formulation.

Figure 15:
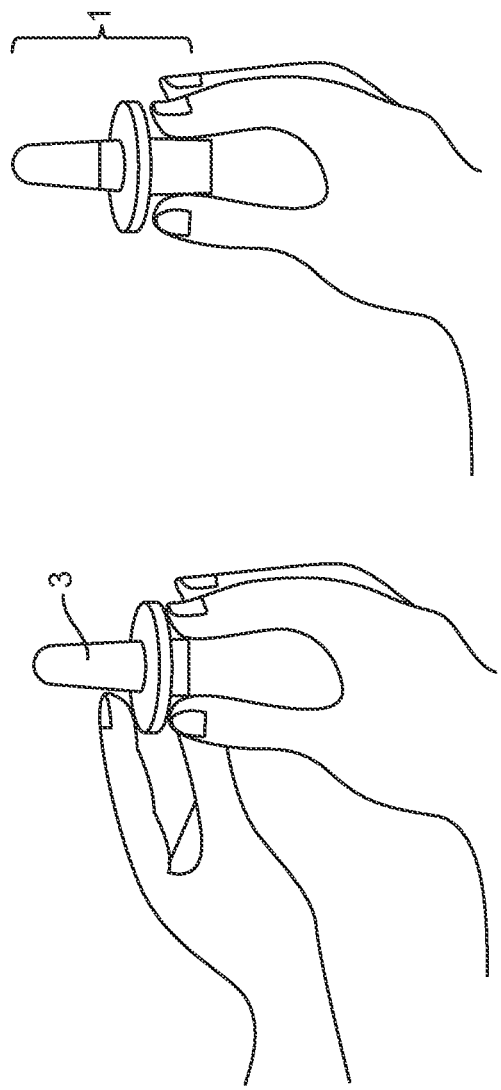
FIG. 15 illustrates the device comprising an applicator in the form of a balm for delivering a pharmaceutical composition by directly contacting the balm on the tip of the applicator to the nasal passage or nasal cavity of an individual who is in need of the pharmaceutical composition.
Figure 16:
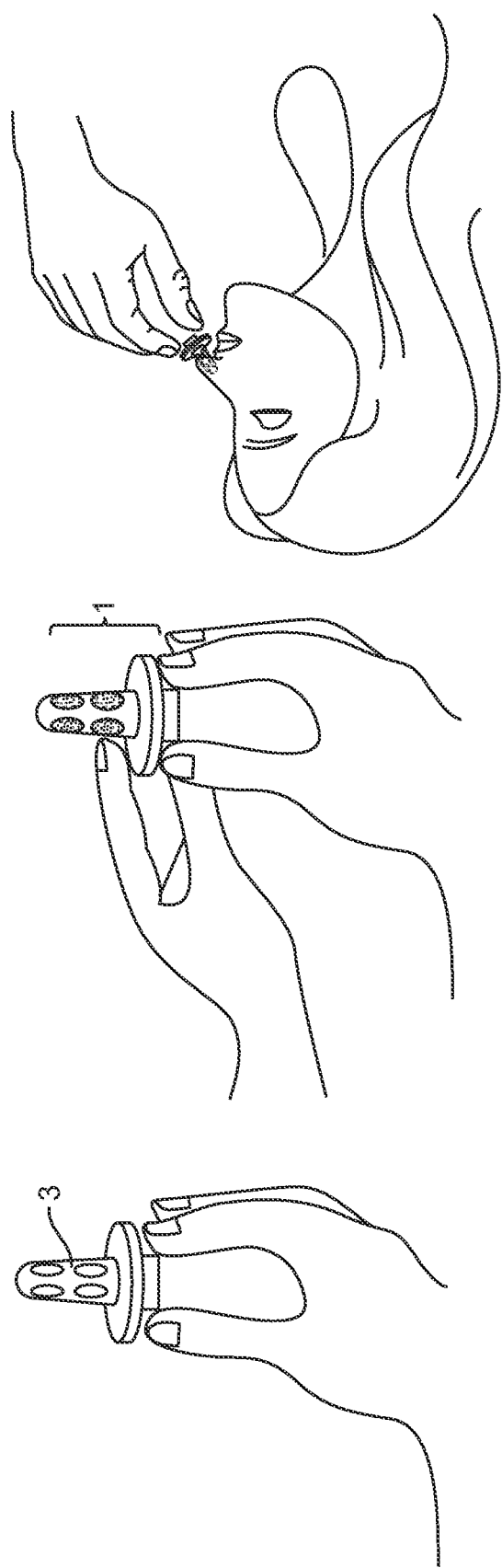
FIG. 16 illustrates the device comprising an applicator in the form of stick dispenser comprising a shaft or a stick for delivering a pharmaceutical composition by directly contacting the shaft or the stick to the nasal cavity of an individual who is in need of the pharmaceutical composition.

In some embodiments, the naloxone containing formulation can be delivered via contacting shaft 8 directly with the nasal passage or nasal cavity of the individual. In some instances, the naloxone containing formulation can be delivered by containing tip 9 directly with the nasal passage or nasal cavity of the individual. In some embodiments, the naloxone containing formulation can be delivered via contacting shaft 8 and tip 9 directly with the nasal passage or nasal cavity of the individual. In some embodiments, the applicator 1 comprises delivering the naloxone containing compositions via nasal swab (FIG. 12), nasal trumpet (FIG. 13), roll-on (FIG. 14), balm (FIG. 15), or a shaft or a stick dispenser (FIG. 16). In some embodiments, the applicator 1 does not actuate nor inject for delivering the naloxone containing formulation. In some embodiments, the nasal swab (FIG. 12) comprises absorbent material such as cotton on tip 9 or along shaft 8 or both tip 9 and shaft 8. In some embodiments, the nasal trumpet (FIG. 13) has a conical shape and is curved along its longitudinal axis so that it conforms to the anatomy of the nasal passage or nasal cavity. In some embodiments, the tip 9 can be movable or removable relative to the applicator 1 and is configured to be manually advanced relative to the applicator 1, and wherein the surface of the applicator 1 which holds the naloxone containing formulation is a surface of the applicator tip 9. In some cases, the tip 9 is rotatable relative to the applicator 1. In some embodiments, the applicator 1 is rotatable relative to the applicator tip 9.

Figure 17A:
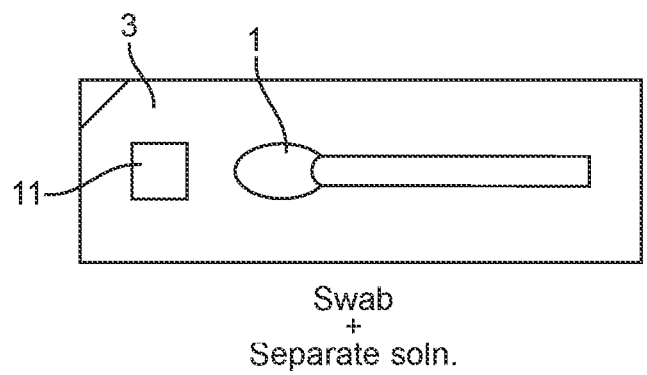
FIG. 17A illustrates the device comprising an applicator and a cover. The cover comprises a reservoir for storing the pharmaceutical composition.
Figure 17B:
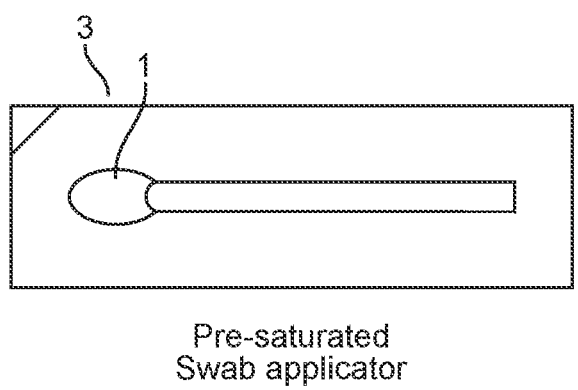
FIG. 17B illustrates the device comprising an applicator that is pre-loaded or pre-saturated with the pharmaceutical composition and a cover. Either the applicator or the cover can comprise a reservoir for storing or pre-loading the applicator with pharmaceutical composition.
Figure 17C:
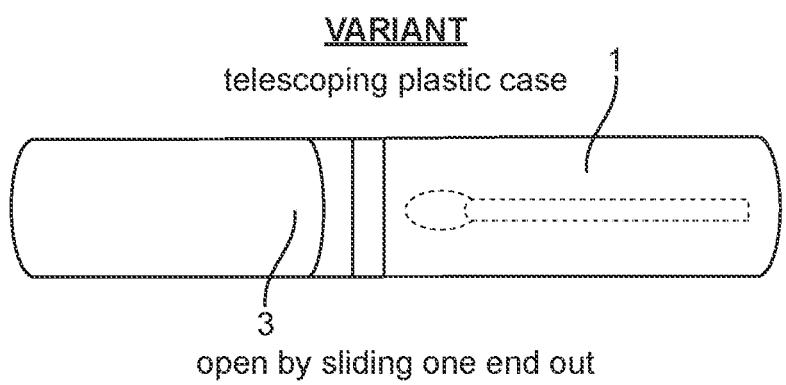
FIG. 17C illustrates a variation of FIG. 17A and FIG. 17B, where the cover, comprising a plastic case, and the applicator can be separated and disconnected from each other by sliding the cover away from the applicator.
Figure 17D:
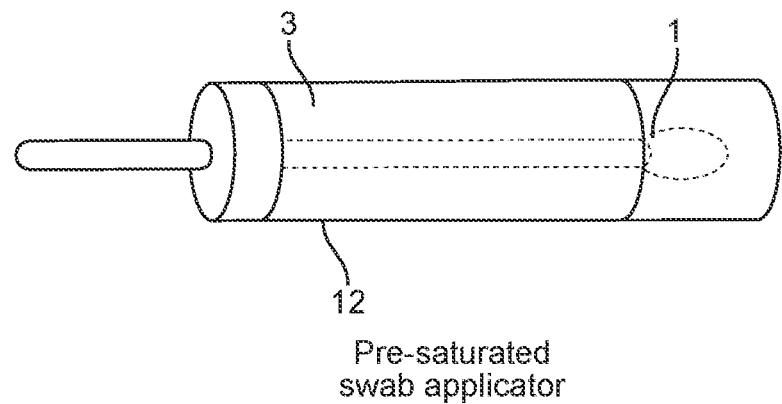
FIG. 17D illustrates a variation of FIG. 12, where the applicator is pre-loaded or pre-saturated with the pharmaceutical composition

In some instances, the applicator 1 is not pre-loaded with the naloxone containing formulation. As shown in FIG. 17A, the reservoir 11 is part of the cover 3. Upon removal of applicator 1 from cover 3, applicator 1 can then be loaded or dipped into the reservoir 11 to load the applicator 1 with the naloxone containing formulation. Also shown in FIG. 17A is cover 3 completely encapsulating applicator 1. In some embodiments, cover 3 comprises plastic pack that can be peeled and removed to expose applicator 1. In some embodiments, cover 3 can comprise thermoplastic formed cover. In some embodiments, cover 3 can comprise a plastic pack, plastic pouch, or foils comprising nickel, copper, or aluminum. In some cases, as shown in FIG. 17B, applicator 1 is pre-loaded with the naloxone containing formulation. In such arrangement, reservoir is integrated as part of applicator 1. In some embodiments, the cove 3 can be thermoformed package covering the pre-saturated swab applicator. FIG. 17C illustrates variations of the devices as shown in FIG. 17A and FIG. 17B, where applicator 1 can be exposed or retrieved by sliding cover 3 away from applicator 1. In such embodiment, cover 3 can be made of plastic case as opposed to a plastic pack or plastic pouch. In some cases, metallic material such as nickel, copper, or aluminum can coat the covers or the applicators or both the covers and the applicators to prevent evaporation of the naloxone containing formulation and to increase shelf life. For example, FIG. 17D demonstrates covering applicator 1 with cover 3, where cover 3 is coated with metallic foil 12. Such metabolic coating can be especially important for when the applicator is pre-loaded or pre-saturated with the naloxone containing formulation.

Figure 17E:
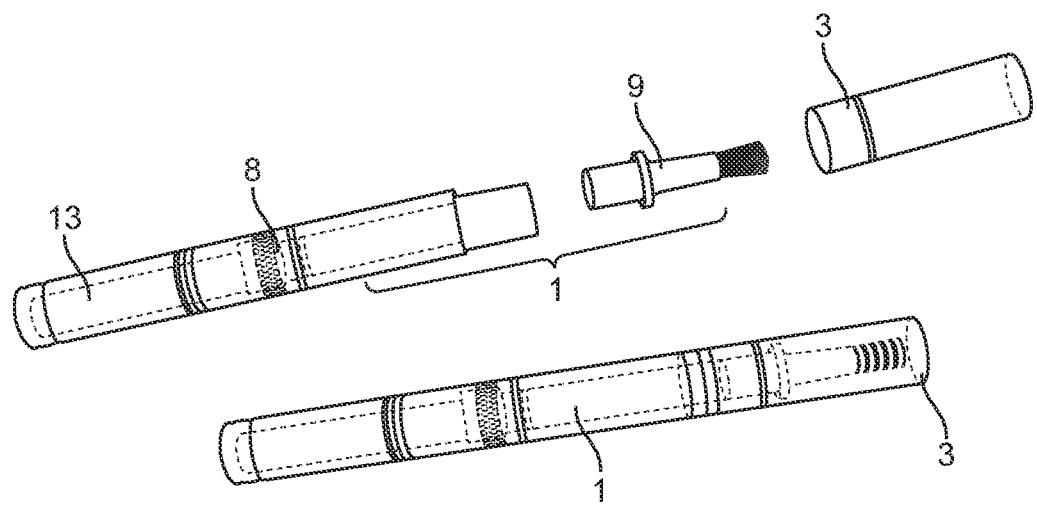
FIG. 17E illustrates the device comprising a replaceable, portable, or releasable applicator, where a metered or multiple doses of the pharmaceutical composition can be dispensed. The applicator and the pharmaceutical composition can be stored together (i.e. the applicator comprising the reservoir) or separately (i.e. the cover comprising the reservoir).
Figure 17F:
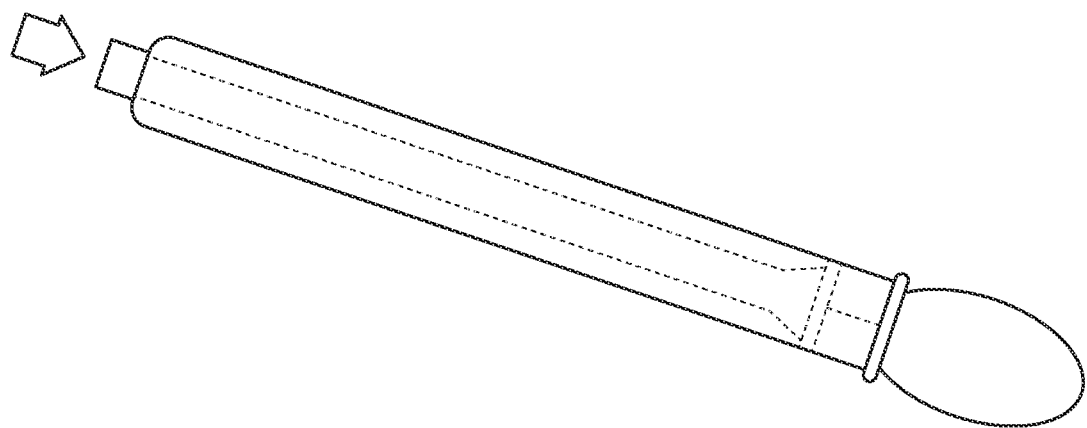
FIG. 17F illustrates the device comprising a delivery mechanism, where pressing of the delivery mechanism delivers the pharmaceutical composition.
Figure 17G:
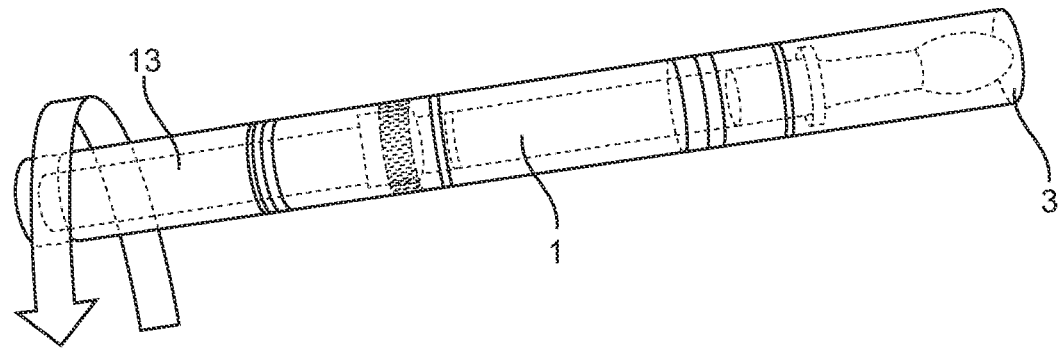
FIG. 17G illustrates a modified version of the device of FIG. 17F, where the pharmaceutical composition can be dispensed by rotating, as opposed to pressing, the delivery mechanism.

In some cases, the applicator comprises an applicator tip and an applicator shaft. As shown in FIG. 17E, applicator tip 9 can be detached from applicator shaft 8. Such embodiment is a reusable device, where the applicator tip can be reused or replaced. In some cases, the removable or detachable applicator tip 9 comprises the swab, nasal trumpet, roll-on, balm, or a shaft or a stick dispenser also described herein. In some cases, applicator tip 9 can be pre-loaded with the naloxone containing formulation. In some embodiments, applicator tip 9 can be loaded with the naloxone containing formulation when cover 3 is disconnected or removed from the applicator 1. In some embodiments, applicator tip 9 can be loaded with the naloxone containing formulation by the individual after cover 3 is removed. In some embodiments, applicator tip 9 delivers the naloxone containing formulation by direct contact with the nasal passage or nasal cavity of the individual. In some cases, applicator tip 9 comprises the reservoir for the naloxone containing formulation. In some cases, applicator shaft 8 comprises the reservoir for the naloxone containing formulation. In some instances, the applicator tip delivers the naloxone containing formulation by activating a delivery mechanism 13, which is at least partially embedded in the applicator shaft 8. In some embodiments, the delivery mechanism can be a push button or a plunger. In some instances, FIG. 17F illustrates a device comprising a delivery mechanism for delivering a pre-metered dose via a swab applicator. In some embodiments, the delivery mechanism can comprise a push button or a plunger that can be at least partially embedded in the applicator and can be activated by pressing or pushing the delivery mechanism 13. Activation of the plunger pushes a pre-metered dose of naloxone HCl through the applicator tip (swab tip). In some cases, instead of a delivery mechanism that can be active by pressing, the delivery mechanism 13 can be a screwing or twisting mechanism, where screwing, twisting, or rotating the delivery mechanism 13 can release naloxone HCl through the applicator tip (swab tip, FIG. 17G).

Figure 18:
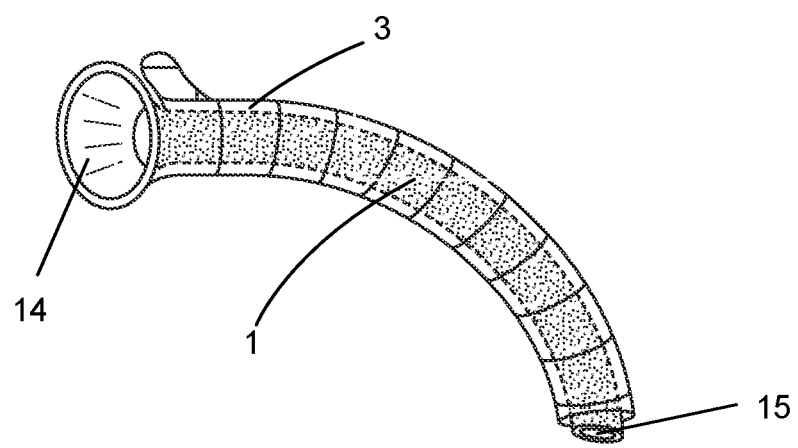
FIG. 18 illustrates a nasal trumpet with a removal cover and pharmaceutical composition pre-loaded on the outside of the applicator.
Figure 19:
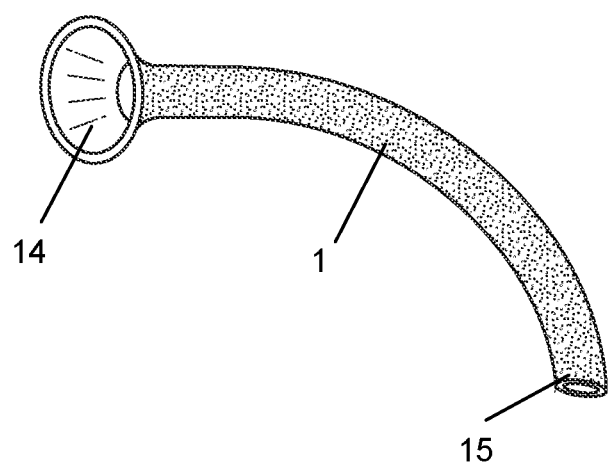
FIG. 19 illustrates the nasal trumpet of FIG. 18 with the cover removed.

Described herein, in some embodiments, is a nasal trumpet for delivering the pharmaceutical compositions described herein. FIG. 18 illustrates an exemplary embodiment of the nasal trumpet, where the cover 3 covers the entire length of the applicator 1. A tap on the cover 3 allows ease of removal of the cover 3 to expose the applicator 1 (FIG. 19). In some cases, the nasal trumpet comprises a proximal end 14 and a distal end 15, where the proximal end is away from the nasal passage when the device is in use. In some cases, the proximal end 14 comprises a flanged end. In some instances, the distal end 15 can comprise a beveled end. In some cases, as shown in FIG. 19, the pharmaceutical composition or the naloxone containing formulation can be stored on the outside of the applicator 1, where the pharmaceutical composition or the naloxone containing formulation can be delivered to the individual by direct contact of the surface of applicator 1 to the surface of the nasal cavity or nasal passage of the individual. In some embodiments, the pharmaceutical composition or the naloxone containing formulation can be delivered via the distal end.

Figure 20:
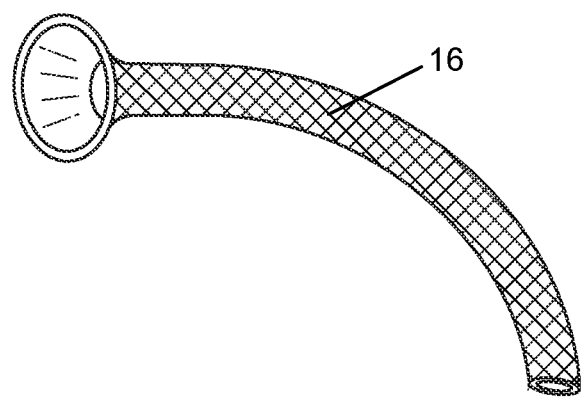
FIG. 20 illustrates a nasal trumpet with openings in the form of a mesh, where the pharmaceutical composition can be dispensed from the reservoir inside the applicator by direct contact of the nasal trumpet of FIG. 20 to the nasal passage.
Figure 21A:
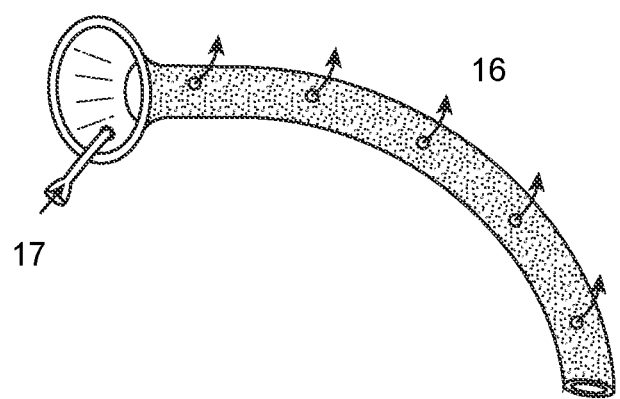
FIG. 21A-B illustrate a nasal trumpet comprising an injection port and with openings for dispensing the pharmaceutical composition.
Figure 21B:
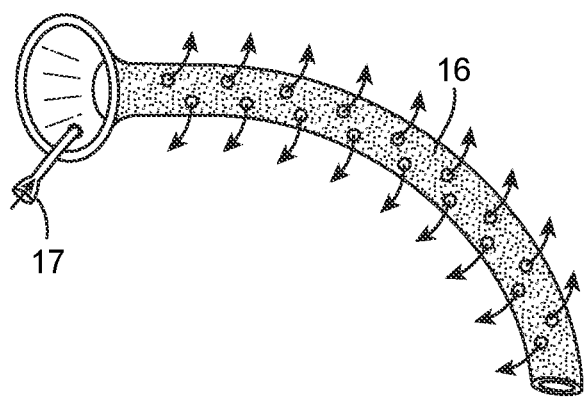

In some embodiments, the applicator can comprise a tubular member connecting the proximal end and the distal end. In some cases, the tubular member comprises at least one opening 16 on the surface of the tubular member. FIG. 20 illustrates the at least one opening 16 arranged in a mesh format, where the pharmaceutical composition of the naloxone containing formulation can be delivered. In some embodiments, the tubular member of the applicator can comprise at least one lumen. In some cases, the at least one lumen can be a reservoir for storing the pharmaceutical composition or the naloxone containing formulation. In some cases, the at least one opening 16 forms a fluid communication with the at least one lumen to dispense the stored pharmaceutical composition or the naloxone containing formulation. In some cases, the at least one opening 16 can deliver a pre-metered dose of the pharmaceutical composition of the naloxone containing formulation.

In some embodiments, the nasal trumpet can comprise at least one injection port 17, where the injection port 17 forms a fluid communication with at least one lumen in the tubular member. In some cases, the pharmaceutical composition or naloxone containing formulation can be injected into the device via injection port 17. In some embodiments, the injected pharmaceutical composition or naloxone containing formulation can be delivered via the fluid communications between the injector port 17 and the at least one lumen and between the at least one lumen with the at least one opening 16. In some cases, the pharmaceutical composition or the naloxone containing formulation can be delivered in one (FIG. 21A) or multiple (FIG. 21B) directions.

In some embodiments, the nasal trumpet (FIG. 22) can comprise a slit 18 along the longitudinal axis of the nasal trumpet device. In some cases, the slit 18 can run the entire length of the longitudinal axis of the nasal trumpet. In some cases, the slit 18 can run a partial length of the longitudinal axis of the nasal trumpet. In some embodiments, the slit 18 can run at least 10%, 20%, 30%, 40%, 50%, 60%, 70%, 80%, 90%, 95%, or 99% length of the longitudinal axis of the nasal trumpet. In some embodiments, the slit 18 can run at most 10%, 20%, 30%, 40%, 50%, 60%, 70%, 80%, 90%, 95%, or 99% length of the longitudinal axis of the nasal trumpet. In some cases, the nasal trumpet comprises protrusion 19 at the flanged proximal end of the nasal trumpet. In some cases, a user of the nasal trumpet of FIG. 22 can open the slit 18 via the opening of the protrusion 19 in the directions as indicated by the arrows. In some cases, the opening of the slit 18 via protrusion 19 enables the use of the nasal trumpet with a fiberoptic scope coupled to an endotracheal tube. In some cases, the nasal trumpet can be used to deliver the pharmaceutical composition or the naloxone containing formulation, while allowing the insertion of the fiberoptic scoped coupled to an endotracheal tube via the at least one lumen inside the tubular member of the applicator. In some cases, the slit 18 allows nasal trumpet to be removed from the partially inserted fiberoptic scope coupled to the endotracheal tube. Upon removal of the nasal trumpet, the fiberoptic scope can be inserted further into the tracheal of the individual. In some cases, nasal trumpet with slit 18 reduces damages to the nasal mucosa and tissues of the nasal cavity and the nasal passage.

Figure 23:
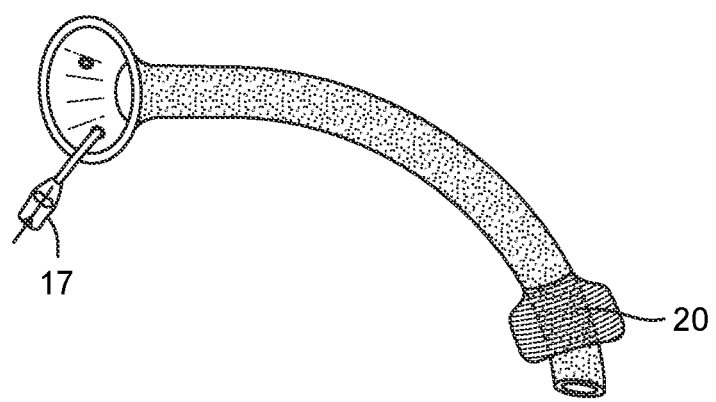
FIG. 23 illustrates a nasal trumpet comprising at least one injection port and an inflatable cuff, where the injection port can form a connection with at least one lumen of the nasal trumpet and the pharmaceutical composition can be injected and administered by through the injection port. The inflatable cuff can be inflated to expand inside the trachea of the individual. In some cases, the inflatable cuff can be inflated via a fluid communication formed between the inflatable cuff, the at least one lumen, and the at least one injection port.

In some embodiments, the nasal trumpet can comprise an inflatable cuff 20 as shown in FIG. 23. In some cases, the inflatable cuff 20 can form a fluid communication with at least one lumen and/or at least one injection port 17, where the inflatable cuff 20 can be inflated via the injection of air or fluids into the at least injector port 17. In some cases, the expansion of the inflatable cuff 20 expands the nasal passage to allow the insertion of the endotracheal tube. In some cases, the use of the combination of slit 18 and inflatable cuff 20 allows the insertion of the endotracheal tube while the nasal trumpet delivers the pharmaceutical composition or the naloxone containing formulation. In some cases, the use of the combination of slit 18 and inflatable cuff 20 allows the insertion of the endotracheal tube before the nasal trumpet delivers the pharmaceutical composition or the naloxone containing formulation. In some cases, the use of the combination of slit 18 and inflatable cuff 20 allows the insertion of the endotracheal tube after the nasal trumpet delivers the pharmaceutical composition or the naloxone containing formulation. In some cases, the use of the combination of slit 18 and inflatable cuff 20 allows the insertion of the endotracheal tube while reducing the damages to the nasal mucosa and tissues of the nasal cavity and the nasal passage.

In some embodiments, the applicator can only be saturated at the point of release (i.e., not stored as pre-saturated). In some cases, the device can be reusable. In some cases, the applicator can be reusable. In some embodiments, the device can deliver multiple doses of the naloxone containing formulation. In some embodiments, the device can deliver multiple doses of the naloxone containing formulation, where the doses of the naloxone containing formulation contain the same volume or amount of naloxone HCl per each dose. In some embodiments, the device can deliver multiple doses of the naloxone containing formulation, where the doses of the naloxone containing formulation contain different volumes or amounts of naloxone HCl per each dose. In some embodiments, only the applicator needs to be replaced after each use. In some embodiments, only the applicator tip needs to be replaced after each use. In some embodiments, the device as described herein can deliver multiple doses of the naloxone containing formulation. In some embodiments, the device can deliver multiple does of the naloxone containing formulation before the applicator or the applicator tip needs to be replaced. In some embodiments, the device can deliver multiple pre-metered doses of the naloxone containing formulation. In some embodiments, the device can deliver multiple pre-metered doses of the naloxone containing formulation before the applicator or the applicator tip needs to be replaced. In some embodiments, the device can be single-use.

In some embodiments, the applicator completes the delivery of the naloxone containing formulation in a single motion via inserting the applicator into the nasal passage or nasal cavity. In some embodiments, the applicator completes the delivery of the naloxone containing formulation in two motions: inserting the applicator into the nasal passage or nasal cavity and an additional motion of moving the inserted applicator. Illustrative one additional motion includes pressing the applicator against the nasal passage or nasal cavity, rotating the inserted applicator, rolling the applicator in a back-and-forth manner, rolling the applicator along the inside of the nasal passage or nasal cavity, or pressing on a push-delivery mechanism.

In some embodiments, the applicator completes the delivery of the naloxone containing formulation within 1 second, after at least 1 second, after at least 10 seconds, after at least 30 seconds, after at least 1 minute, after at least 5 minutes, or after at least 10 minutes.

In some embodiments, the applicator delivers a pre-metered amount or volume of the naloxone containing formulation. In some embodiments, the amount or volume of the naloxone containing formulation is pre-metered by the amount or volume stored in the reservoir in the cover. In some embodiments, the amount or volume of the naloxone containing formulation is pre-metered by the amount or volume stored in the reservoir in the applicator. In some embodiments, the amount or volume of the naloxone containing formulation is pre-metered by the amount or volume stored in the applicator. In some embodiments, the amount or volume of the naloxone containing formulation is pre-metered by the amount or volume stored in the shaft of the applicator. In some embodiments, the amount or volume of the naloxone containing formulation is pre-metered by the amount or volume stored on the surface of the shaft of the applicator. In some embodiments, the amount or volume of the naloxone containing formulation is pre-metered by the amount or volume stored in the tip of the applicator. In some embodiments, the amount or volume of the naloxone containing formulation is pre-metered by the amount or volume stored on the surface of the tip of the applicator.

In some embodiments, the amount or volume of the naloxone containing formulation is pre-metered by the amount or volume stored in the nasal trumpet. In some embodiments, the amount or volume of the naloxone containing formulation is pre-metered by the amount or volume stored on the surface of the nasal trumpet. In some embodiments, the amount or volume of the naloxone containing formulation is pre-metered by the amount or volume of the naloxone containing formulation being absorbed by the nasal swab. In some embodiments, the amount or volume of the naloxone containing formulation is pre-metered by the amount or volume housing stored in the roller-ball or roll-on of the applicator. In some embodiments, the amount or volume of the naloxone containing formulation is pre-metered by the amount or volume housing stored on the surface of the roller-ball or roll-on of the applicator. In some embodiments, the amount or volume of the naloxone containing formulation is pre-metered by the amount or volume stored in the balm of the applicator. In some embodiments, the amount or volume of the naloxone containing formulation is pre-metered by the amount or volume stored on the surface of the balm of the applicator. In some embodiments, the pre-metered volume or amount of naloxone containing formulation being delivered can be an aqueous formulation, a semi-solid formulation, a gel, a solid formulation, or a powder formulation.

In some embodiments, the applicator delivers a volume of naloxone containing formulation that is about 10 μl to about 500 μl. In some embodiments, the applicator delivers an volume of naloxone containing formulation that is about 10 μl to about 20 μl, about 10 μl to about 50 μl, about 10 μl to about 100 μl, about 10 μl to about 150 μl, about 10 μl to about 200 μl, about 10 μl to about 250 μl, about 10 μl to about 300 μl, about 10 μl to about 450 μl, about 10 μl to about 500 μl, about 20 μl to about 50 μl, about 20 μl to about 100 μl, about 20 μl to about 150 μl, about 20 μl to about 200 μl, about 20 μl to about 250 μl, about 20 μl to about 300 μl, about 20 µl to about 450 µl, about 20 µl to about 500 µl, about 50 µl to about 100 µl, about 50 µl to about 150 µl, about 50 µl to about 200 µl, about 50 µl to about 250 µl, about 50 µl to about 300 µl, about 50 µl to about 450 µl, about 50 µl to about 500 µl, about 100 µl to about 150 µl, about 100 µl to about 200 µl, about 100 µl to about 250 µl, about 100 µl to about 300 µl, about 100 µl to about 450 µl, about 100 µl to about 500 µl, about 150 µl to about 200 µl, about 150 µl to about 250 µl, about 150 µl to about 300 µl, about 150 µl to about 450 µl, about 150 µl to about 500 µl, about 200 µl to about 250 µl, about 200 µl to about 300 µl, about 200 µl to about 450 µl, about 200 µl to about 500 µl, about 250 µl to about 300 µl, about 250 µl to about 450 µl, about 250 µl to about 500 µl, about 300 µl to about 450 µl, about 300 µl to about 500 µl, or about 450 µl to about 500 µl. In some embodiments, the applicator delivers a volume of naloxone containing formulation that is about 10 µl, about 20 µl, about 50 µl, about 100 µl, about 150 µl, about 200 µl, about 250 µl, about 300 µl, about 450 µl, or about 500 µl. In some embodiments, the applicator delivers a volume of naloxone containing formulation that is at least about 10 µl, about 20 µl, about 50 µl, about 100 µl, about 150 µl, about 200 µl, about 250 µl, about 300 µl, or about 450 µl. In some embodiments, the applicator delivers a volume of naloxone containing formulation that is at most about 20 µl, about 50 µl, about 100 µl, about 150 µl, about 200 µl, about 250 µl, about 300 µl, about 450 µl, or about 500 µl.

In some embodiments, the applicator delivers a volume of naloxone containing formulation that is at most about 10 µl to about 500 µl. In some embodiments, the applicator delivers an volume of naloxone containing formulation that is at most about 10 µl to about 20 µl, about 10 µl to about 50 µl, about 10 µl to about 100 µl, about 10 µl to about 150 µl, about 10 µl to about 200 µl, about 10 µl to about 250 µl, about 10 µl to about 300 µl, about 10 µl to about 450 µl, about 10 µl to about 500 µl, about 20 µl to about 50 µl, about 20 µl to about 100 µl, about 20 µl to about 150 µl, about 20 µl to about 200 µl, about 20 µl to about 250 µl, about 20 µl to about 300 µl, about 20 µl to about 450 µl, about 20 µl to about 500 µl, about 50 µl to about 100 µl, about 50 µl to about 150 µl, about 50 µl to about 200 µl, about 50 µl to about 250 µl, about 50 µl to about 300 µl, about 50 µl to about 450 µl, about 50 µl to about 500 µl, about 100 µl to about 150 µl, about 100 µl to about 200 µl, about 100 µl to about 250 µl, about 100 µl to about 300 µl, about 100 µl to about 450 µl, about 100 µl to about 500 µl, about 150 µl to about 200 µl, about 150 µl to about 250 µl, about 150 µl to about 300 µl, about 150 µl to about 450 µl, about 150 µl to about 500 µl, about 200 µl to about 250 µl, about 200 µl to about 300 µl, about 200 µl to about 450 µl, about 200 µl to about 500 µl, about 250 µl to about 300 µl, about 250 µl to about 450 µl, about 250 µl to about 500 µl, about 300 µl to about 450 µl, about 300 µl to about 500 µl, or about 450 µl to about 500 µl. In some embodiments, the applicator delivers a volume of naloxone containing formulation that is at most about 10 µl, about 20 µl, about 50 µl, about 100 µl, about 150 µl, about 200 µl, about 250 µl, about 300 µl, about 450 µl, or about 500 µl. In some embodiments, the applicator delivers a volume of naloxone containing formulation that is at most at least about 10 µl, about 20 µl, about 50 µl, about 100 µl, about 150 µl, about 200 µl, about 250 µl, about 300 µl, or about 450 µl. In some embodiments, the applicator delivers a volume of naloxone containing formulation that is at most at most about 20 µl, about 50 µl, about 100 µl, about 150 µl, about 200 µl, about 250 µl, about 300 µl, about 450 µl, or about 500 µl.

In some embodiments, the applicator delivers a volume of naloxone containing formulation that is at least about 10 µl to about 500 µl. In some embodiments, the applicator delivers an volume of naloxone containing formulation that is at least about 10 µl to about 20 µl, about 10 µl to about 50 µl, about 10 µl to about 100 µl, about 10 µl to about 150 µl, about 10 µl to about 200 µl, about 10 µl to about 250 µl, about 10 µl to about 300 µl, about 10 µl to about 350 µl, about 10 µl to about 400 µl, about 10 µl to about 450 µl, about 10 µl to about 500 µl, about 20 µl to about 50 µl, about 20 µl to about 100 µl, about 20 µl to about 150 µl, about 20 µl to about 200 µl, about 20 µl to about 250 µl, about 20 µl to about 300 µl, about 20 µl to about 350 µl, about 20 µl to about 400 µl, about 20 µl to about 450 µl, about 20 µl to about 500 µl, about 50 µl to about 100 µl, about 50 µl to about 150 µl, about 50 µl to about 200 µl, about 50 µl to about 250 µl, about 50 µl to about 300 µl, about 50 µl to about 350 µl, about 50 µl to about 400 µl, about 50 µl to about 450 µl, about 50 µl to about 500 µl, about 100 µl to about 150 µl, about 100 µl to about 200 µl, about 100 µl to about 250 µl, about 100 µl to about 300 µl, about 100 µl to about 350 µl, about 100 µl to about 400 µl, about 100 µl to about 450 µl, about 100 µl to about 500 µl, about 150 µl to about 200 µl, about 150 µl to about 250 µl, about 150 µl to about 300 µl, about 150 µl to about 350 µl, about 150 µl to about 400 µl, about 150 µl to about 450 µl, about 150 µl to about 500 µl, about 200 µl to about 250 µl, about 200 µl to about 300 µl, about 200 µl to about 350 µl, about 200 µl to about 400 µl, about 200 µl to about 450 µl, about 200 µl to about 500 µl, about 250 µl to about 300 µl, about 250 µl to about 350 µl, about 250 µl to about 400 µl, about 250 µl to about 450 µl, about 250 µl to about 500 µl, about 300 µl to about 350 µl, about 300 µl to about 400 µl, about 300 µl to about 450 µl, about 300 µl to about 500 µl, about 350 µl to about 400 µl, about 350 µl to about 450 µl, about 350 µl to about 500 µl, about 400 µl to about 450 µl, about 400 µl to about 500 µl, or about 450 µl to about 500 µl. In some embodiments, the applicator delivers a volume of naloxone containing formulation that is at least about 10 µl, about 20 µl, about 50 µl, about 100 µl, about 150 µl, about 200 µl, about 250 µl, about 300 µl, about 350 µl, about 400 µl, about 450 µl, or about 500 µl. In some embodiments, the applicator 1 delivers a volume of naloxone containing formulation that is at least at least about 10 µl, about 20 µl, about 50 µl, about 100 µl, about 150 µl, about 200 µl, about 250 µl, about 300 µl, about 350 µl, about 400 µl, or about 450 µl. In some embodiments, the applicator delivers a volume of naloxone containing formulation that is at least at most about 20 µl, about 50 µl, about 100 µl, about 150 µl, about 200 µl, about 250 µl, about 300 µl, about 350 µl, about 400 µl, about 450 µl, or about 500 µl.

In some embodiments, the applicator delivers a naloxone containing formulation comprising naloxone HCl in the amount that is about 0.1 mg/dose to about 100 mg/dose. In some embodiments, the applicator delivers a naloxone containing formulation comprising naloxone HCl in the amount that is about 0.1 mg/dose to about 0.5 mg/dose, about 0.1 mg/dose to about 1 mg/dose, about 0.1 mg/dose to about 2.5 mg/dose, about 0.1 mg/dose to about 5 mg/dose, about 0.1 mg/dose to about 7.5 mg/dose, about 0.1 mg/dose to about 10 mg/dose, about 0.1 mg/dose to about 12.5 mg/dose, about 0.1 mg/dose to about 15 mg/dose, about 0.1 mg/dose to about 20 mg/dose, about 0.1 mg/dose to about 50 mg/dose, about 0.1 mg/dose to about 100 mg/dose, about 0.5 mg/dose to about 1 mg/dose, about 0.5 mg/dose to about 2.5 mg/dose, about 0.5 mg/dose to about 5 mg/dose, about 0.5 mg/dose to about 7.5 mg/dose, about 0.5 mg/dose to about 10 mg/dose, about 0.5 mg/dose to about 12.5 mg/dose, about 0.5 mg/dose to about 15 mg/dose, about 0.5 mg/dose to about 20 mg/dose, about 0.5 mg/dose to about 50 mg/dose, about 0.5 mg/dose to about 100 mg/dose, about 1 mg/dose to about 2.5 mg/dose, about 1 mg/dose to about 5 mg/dose, about 1 mg/dose to about 7.5 mg/dose, about 1 mg/dose to about 10 mg/dose, about 1 mg/dose to about 12.5 mg/dose, about 1 mg/dose to about 15 mg/dose, about 1 mg/dose to about 20 mg/dose, about 1 mg/dose to about 50 mg/dose, about 1 mg/dose to about 100 mg/dose, about 2.5 mg/dose to about 5 mg/dose, about 2.5 mg/dose to about 7.5 mg/dose, about 2.5 mg/dose to about 10 mg/dose, about 2.5 mg/dose to about 12.5 mg/dose, about 2.5 mg/dose to about 15 mg/dose, about 2.5 mg/dose to about 20 mg/dose, about 2.5 mg/dose to about 50 mg/dose, about 2.5 mg/dose to about 100 mg/dose, about 5 mg/dose to about 7.5 mg/dose, about 5 mg/dose to about 10 mg/dose, about 5 mg/dose to about 12.5 mg/dose, about 5 mg/dose to about 15 mg/dose, about 5 mg/dose to about 20 mg/dose, about 5 mg/dose to about 50 mg/dose, about 5 mg/dose to about 100 mg/dose, about 7.5 mg/dose to about 10 mg/dose, about 7.5 mg/dose to about 12.5 mg/dose, about 7.5 mg/dose to about 15 mg/dose, about 7.5 mg/dose to about 20 mg/dose, about 7.5 mg/dose to about 50 mg/dose, about 7.5 mg/dose to about 100 mg/dose, about 10 mg/dose to about 12.5 mg/dose, about 10 mg/dose to about 15 mg/dose, about 10 mg/dose to about 20 mg/dose, about 10 mg/dose to about 50 mg/dose, about 10 mg/dose to about 100 mg/dose, about 12.5 mg/dose to about 15 mg/dose, about 12.5 mg/dose to about 20 mg/dose, about 12.5 mg/dose to about 50 mg/dose, about 12.5 mg/dose to about 100 mg/dose, about 15 mg/dose to about 20 mg/dose, about 15 mg/dose to about 50 mg/dose, about 15 mg/dose to about 100 mg/dose, about 20 mg/dose to about 50 mg/dose, about 20 mg/dose to about 100 mg/dose, or about 50 mg/dose to about 100 mg/dose. In some embodiments, the applicator delivers a naloxone containing formulation comprising naloxone HCl in the amount that is about 0.1 mg/dose, about 0.5 mg/dose, about 1 mg/dose, about 2.5 mg/dose, about 5 mg/dose, about 7.5 mg/dose, about 10 mg/dose, about 12.5 mg/dose, about 15 mg/dose, about 20 mg/dose, about 50 mg/dose, or about 100 mg/dose. In some embodiments, the applicator delivers a naloxone containing formulation comprising naloxone HCl in the amount that is at least about 0.1 mg/dose, about 0.5 mg/dose, about 1 mg/dose, about 2.5 mg/dose, about 5 mg/dose, about 7.5 mg/dose, about 10 mg/dose, about 12.5 mg/dose, about 15 mg/dose, about 20 mg/dose, or about 50 mg/dose. In some embodiments, the applicator delivers a naloxone containing formulation comprising naloxone HCl in the amount that is at most about 0.5 mg/dose, about 1 mg/dose, about 2.5 mg/dose, about 5 mg/dose, about 7.5 mg/dose, about 10 mg/dose, about 12.5 mg/dose, about 15 mg/dose, about 20 mg/dose, about 50 mg/dose, or about 100 mg/dose.

In some embodiments, the applicator delivers a naloxone containing formulation comprising naloxone HCl in the amount that is at most about 0.1 mg/dose to about 100 mg/dose. In some embodiments, the applicator delivers a naloxone containing formulation comprising naloxone HCl in the amount that is at most about 0.1 mg/dose to about 0.5 mg/dose, about 0.1 mg/dose to about 1 mg/dose, about 0.1 mg/dose to about 2.5 mg/dose, about 0.1 mg/dose to about 5 mg/dose, about 0.1 mg/dose to about 7.5 mg/dose, about 0.1 mg/dose to about 10 mg/dose, about 0.1 mg/dose to about 12.5 mg/dose, about 0.1 mg/dose to about 15 mg/dose, about 0.1 mg/dose to about 20 mg/dose, about 0.1 mg/dose to about 50 mg/dose, about 0.1 mg/dose to about 100 mg/dose, about 0.5 mg/dose to about 1 mg/dose, about 0.5 mg/dose to about 2.5 mg/dose, about 0.5 mg/dose to about 5 mg/dose, about 0.5 mg/dose to about 7.5 mg/dose, about 0.5 mg/dose to about 10 mg/dose, about 0.5 mg/dose to about 12.5 mg/dose, about 0.5 mg/dose to about 15 mg/dose, about 0.5 mg/dose to about 20 mg/dose, about 0.5 mg/dose to about 50 mg/dose, about 0.5 mg/dose to about 100 mg/dose, about 1 mg/dose to about 2.5 mg/dose, about 1 mg/dose to about 5 mg/dose, about 1 mg/dose to about 7.5 mg/dose, about 1 mg/dose to about 10 mg/dose, about 1 mg/dose to about 12.5 mg/dose, about 1 mg/dose to about 15 mg/dose, about 1 mg/dose to about 20 mg/dose, about 1 mg/dose to about 50 mg/dose, about 1 mg/dose to about 100 mg/dose, about 2.5 mg/dose to about 5 mg/dose, about 2.5 mg/dose to about 7.5 mg/dose, about 2.5 mg/dose to about 10 mg/dose, about 2.5 mg/dose to about 12.5 mg/dose, about 2.5 mg/dose to about 15 mg/dose, about 2.5 mg/dose to about 20 mg/dose, about 2.5 mg/dose to about 50 mg/dose, about 2.5 mg/dose to about 100 mg/dose, about 5 mg/dose to about 7.5 mg/dose, about 5 mg/dose to about 10 mg/dose, about 5 mg/dose to about 12.5 mg/dose, about 5 mg/dose to about 15 mg/dose, about 5 mg/dose to about 20 mg/dose, about 5 mg/dose to about 50 mg/dose, about 5 mg/dose to about 100 mg/dose, about 7.5 mg/dose to about 10 mg/dose, about 7.5 mg/dose to about 12.5 mg/dose, about 7.5 mg/dose to about 15 mg/dose, about 7.5 mg/dose to about 20 mg/dose, about 7.5 mg/dose to about 50 mg/dose, about 7.5 mg/dose to about 100 mg/dose, about 10 mg/dose to about 12.5 mg/dose, about 10 mg/dose to about 15 mg/dose, about 10 mg/dose to about 20 mg/dose, about 10 mg/dose to about 50 mg/dose, about 10 mg/dose to about 100 mg/dose, about 12.5 mg/dose to about 15 mg/dose, about 12.5 mg/dose to about 20 mg/dose, about 12.5 mg/dose to about 50 mg/dose, about 12.5 mg/dose to about 100 mg/dose, about 15 mg/dose to about 20 mg/dose, about 15 mg/dose to about 50 mg/dose, about 15 mg/dose to about 100 mg/dose, about 20 mg/dose to about 50 mg/dose, about 20 mg/dose to about 100 mg/dose, or about 50 mg/dose to about 100 mg/dose. In some embodiments, the applicator delivers a naloxone containing formulation comprising naloxone HCl in the amount that is at most about 0.1 mg/dose, about 0.5 mg/dose, about 1 mg/dose, about 2.5 mg/dose, about 5 mg/dose, about 7.5 mg/dose, about 10 mg/dose, about 12.5 mg/dose, about 15 mg/dose, about 20 mg/dose, about 50 mg/dose, or about 100 mg/dose. In some embodiments, the applicator delivers a naloxone containing formulation comprising naloxone HCl in the amount that is at most at least about 0.1 mg/dose, about 0.5 mg/dose, about 1 mg/dose, about 2.5 mg/dose, about 5 mg/dose, about 7.5 mg/dose, about 10 mg/dose, about 12.5 mg/dose, about 15 mg/dose, about 20 mg/dose, or about 50 mg/dose. In some embodiments, the applicator delivers a naloxone containing formulation comprising naloxone HCl in the amount that is at most at most about 0.5 mg/dose, about 1 mg/dose, about 2.5 mg/dose, about 5 mg/dose, about 7.5 mg/dose, about 10 mg/dose, about 12.5 mg/dose, about 15 mg/dose, about 20 mg/dose, about 50 mg/dose, or about 100 mg/dose.

In some embodiments, the applicator delivers a naloxone containing formulation comprising naloxone HCl in the amount that is at least about 0.1 mg/dose to about 100 mg/dose. In some embodiments, the applicator delivers a naloxone containing formulation comprising naloxone HCl in the amount that is at least about 0.1 mg/dose to about 0.5 mg/dose, about 0.1 mg/dose to about 1 mg/dose, about 0.1 mg/dose to about 2.5 mg/dose, about 0.1 mg/dose to about 5 mg/dose, about 0.1 mg/dose to about 7.5 mg/dose, about 0.1 mg/dose to about 10 mg/dose, about 0.1 mg/dose to about 12.5 mg/dose, about 0.1 mg/dose to about 15 mg/dose, about 0.1 mg/dose to about 20 mg/dose, about 0.1 mg/dose to about 50 mg/dose, about 0.1 mg/dose to about 100 mg/dose, about 0.5 mg/dose to about 1 mg/dose, about 0.5 mg/dose to about 2.5 mg/dose, about 0.5 mg/dose to about 5 mg/dose, about 0.5 mg/dose to about 7.5 mg/dose, about 0.5 mg/dose to about 10 mg/dose, about 0.5 mg/dose to about 12.5 mg/dose, about 0.5 mg/dose to about 15 mg/dose, about 0.5 mg/dose to about 20 mg/dose, about 0.5 mg/dose to about 50 mg/dose, about 0.5 mg/dose to about 100 mg/dose, about 1 mg/dose to about 2.5 mg/dose, about 1 mg/dose to about 5 mg/dose, about 1 mg/dose to about 7.5 mg/dose, about 1 mg/dose to about 10 mg/dose, about 1 mg/dose to about 12.5 mg/dose, about 1 mg/dose to about 15 mg/dose, about 1 mg/dose to about 20 mg/dose, about 1 mg/dose to about 50 mg/dose, about 1 mg/dose to about 100 mg/dose, about 2.5 mg/dose to about 5 mg/dose, about 2.5 mg/dose to about 7.5 mg/dose, about 2.5 mg/dose to about 10 mg/dose, about 2.5 mg/dose to about 12.5 mg/dose, about 2.5 mg/dose to about 15 mg/dose, about 2.5 mg/dose to about 20 mg/dose, about 2.5 mg/dose to about 50 mg/dose, about 2.5 mg/dose to about 100 mg/dose, about 5 mg/dose to about 7.5 mg/dose, about 5 mg/dose to about 10 mg/dose, about 5 mg/dose to about 12.5 mg/dose, about 5 mg/dose to about 15 mg/dose, about 5 mg/dose to about 20 mg/dose, about 5 mg/dose to about 50 mg/dose, about 5 mg/dose to about 100 mg/dose, about 7.5 mg/dose to about 10 mg/dose, about 7.5 mg/dose to about 12.5 mg/dose, about 7.5 mg/dose to about 15 mg/dose, about 7.5 mg/dose to about 20 mg/dose, about 7.5 mg/dose to about 50 mg/dose, about 7.5 mg/dose to about 100 mg/dose, about 10 mg/dose to about 12.5 mg/dose, about 10 mg/dose to about 15 mg/dose, about 10 mg/dose to about 20 mg/dose, about 10 mg/dose to about 50 mg/dose, about 10 mg/dose to about 100 mg/dose, about 12.5 mg/dose to about 15 mg/dose, about 12.5 mg/dose to about 20 mg/dose, about 12.5 mg/dose to about 50 mg/dose, about 12.5 mg/dose to about 100 mg/dose, about 15 mg/dose to about 20 mg/dose, about 15 mg/dose to about 50 mg/dose, about 15 mg/dose to about 100 mg/dose, about 20 mg/dose to about 50 mg/dose, about 20 mg/dose to about 100 mg/dose, or about 50 mg/dose to about 100 mg/dose. In some embodiments, the applicator delivers a naloxone containing formulation comprising naloxone HCl in the amount that is at least about 0.1 mg/dose, about 0.5 mg/dose, about 1 mg/dose, about 2.5 mg/dose, about 5 mg/dose, about 7.5 mg/dose, about 10 mg/dose, about 12.5 mg/dose, about 15 mg/dose, about 20 mg/dose, about 50 mg/dose, or about 100 mg/dose. In some embodiments, the applicator 1 delivers a naloxone containing formulation comprising naloxone HCl in the amount that is at least at least about 0.1 mg/dose, about 0.5 mg/dose, about 1 mg/dose, about 2.5 mg/dose, about 5 mg/dose, about 7.5 mg/dose, about 10 mg/dose, about 12.5 mg/dose, about 15 mg/dose, about 20 mg/dose, or about 50 mg/dose. In some embodiments, the applicator delivers a naloxone containing formulation comprising naloxone HCl in the amount that is at least at most about 0.5 mg/dose, about 1 mg/dose, about 2.5 mg/dose, about 5 mg/dose, about 7.5 mg/dose, about 10 mg/dose, about 12.5 mg/dose, about 15 mg/dose, about 20 mg/dose, about 50 mg/dose, or about 100 mg/dose.

In some embodiments, the applicator delivers a naloxone containing formulation comprising naloxone HCl in the amount that is about 20 mg/ml to about 100 mg/ml. In some embodiments, the applicator delivers a naloxone containing formulation comprising naloxone HCl in the amount that is about 20 mg/ml to about 25 mg/ml, about 20 mg/ml to about 30 mg/ml, about 20 mg/ml to about 35 mg/ml, about 20 mg/ml to about 40 mg/ml, about 20 mg/ml to about 45 mg/ml, about 20 mg/ml to about 50 mg/ml, about 20 mg/ml to about 55 mg/ml, about 20 mg/ml to about 60 mg/ml, about 20 mg/ml to about 65 mg/ml, about 20 mg/ml to about 70 mg/ml, about 20 mg/ml to about 100 mg/ml, about 25 mg/ml to about 30 mg/ml, about 25 mg/ml to about 35 mg/ml, about 25 mg/ml to about 40 mg/ml, about 25 mg/ml to about 45 mg/ml, about 25 mg/ml to about 50 mg/ml, about 25 mg/ml to about 55 mg/ml, about 25 mg/ml to about 60 mg/ml, about 25 mg/ml to about 65 mg/ml, about 25 mg/ml to about 70 mg/ml, about 25 mg/ml to about 100 mg/ml, about 30 mg/ml to about 35 mg/ml, about 30 mg/ml to about 40 mg/ml, about 30 mg/ml to about 45 mg/ml, about 30 mg/ml to about 50 mg/ml, about 30 mg/ml to about 55 mg/ml, about 30 mg/ml to about 60 mg/ml, about 30 mg/ml to about 65 mg/ml, about 30 mg/ml to about 70 mg/ml, about 30 mg/ml to about 100 mg/ml, about 35 mg/ml to about 40 mg/ml, about 35 mg/ml to about 45 mg/ml, about 35 mg/ml to about 50 mg/ml, about 35 mg/ml to about 55 mg/ml, about 35 mg/ml to about 60 mg/ml, about 35 mg/ml to about 65 mg/ml, about 35 mg/ml to about 70 mg/ml, about 35 mg/ml to about 100 mg/ml, about 40 mg/ml to about 45 mg/ml, about 40 mg/ml to about 50 mg/ml, about 40 mg/ml to about 55 mg/ml, about 40 mg/ml to about 60 mg/ml, about 40 mg/ml to about 65 mg/ml, about 40 mg/ml to about 70 mg/ml, about 40 mg/ml to about 100 mg/ml, about 45 mg/ml to about 50 mg/ml, about 45 mg/ml to about 55 mg/ml, about 45 mg/ml to about 60 mg/ml, about 45 mg/ml to about 65 mg/ml, about 45 mg/ml to about 70 mg/ml, about 45 mg/ml to about 100 mg/ml, about 50 mg/ml to about 55 mg/ml, about 50 mg/ml to about 60 mg/ml, about 50 mg/ml to about 65 mg/ml, about 50 mg/ml to about 70 mg/ml, about 50 mg/ml to about 100 mg/ml, about 55 mg/ml to about 60 mg/ml, about 55 mg/ml to about 65 mg/ml, about 55 mg/ml to about 70 mg/ml, about 55 mg/ml to about 100 mg/ml, about 60 mg/ml to about 65 mg/ml, about 60 mg/ml to about 70 mg/ml, about 60 mg/ml to about 100 mg/ml, about 65 mg/ml to about 70 mg/ml, about 65 mg/ml to about 100 mg/ml, or about 70 mg/ml to about 100 mg/ml. In some embodiments, the applicator delivers a naloxone containing formulation comprising naloxone HCl in the amount that is about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, or about 100 mg/ml. In some embodiments, the applicator delivers a naloxone containing formulation comprising naloxone HCl in the amount that is at least about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, or about 70 mg/ml. In some embodiments, the applicator delivers a naloxone containing formulation comprising naloxone HCl in the amount that is at most about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, or about 100 mg/ml.

In some embodiments, the applicator delivers a naloxone containing formulation comprising naloxone HCl in the amount that is at most about 20 mg/ml to about 100 mg/ml. In some embodiments, the applicator delivers a naloxone containing formulation comprising naloxone HCl in the amount that is at most about 20 mg/ml to about 25 mg/ml, about 20 mg/ml to about 30 mg/ml, about 20 mg/ml to about 35 mg/ml, about 20 mg/ml to about 40 mg/ml, about 20 mg/ml to about 45 mg/ml, about 20 mg/ml to about 50 mg/ml, about 20 mg/ml to about 55 mg/ml, about 20 mg/ml to about 60 mg/ml, about 20 mg/ml to about 65 mg/ml, about 20 mg/ml to about 70 mg/ml, about 20 mg/ml to about 100 mg/ml, about 25 mg/ml to about 30 mg/ml, about 25 mg/ml to about 35 mg/ml, about 25 mg/ml to about 40 mg/ml, about 25 mg/ml to about 45 mg/ml, about 25 mg/ml to about 50 mg/ml, about 25 mg/ml to about 55 mg/ml, about 25 mg/ml to about 60 mg/ml, about 25 mg/ml to about 65 mg/ml, about 25 mg/ml to about 70 mg/ml, about 25 mg/ml to about 100 mg/ml, about 30 mg/ml to about 35 mg/ml, about 30 mg/ml to about 40 mg/ml, about 30 mg/ml to about 45 mg/ml, about 30 mg/ml to about 50 mg/ml, about 30 mg/ml to about 55 mg/ml, about 30 mg/ml to about 60 mg/ml, about 30 mg/ml to about 65 mg/ml, about 30 mg/ml to about 70 mg/ml, about 30 mg/ml to about 100 mg/ml, about 35 mg/ml to about 40 mg/ml, about 35 mg/ml to about 45 mg/ml, about 35 mg/ml to about 50 mg/ml, about 35 mg/ml to about 55 mg/ml, about 35 mg/ml to about 60 mg/ml, about 35 mg/ml to about 65 mg/ml, about 35 mg/ml to about 70 mg/ml, about 35 mg/ml to about 100 mg/ml, about 40 mg/ml to about 45 mg/ml, about 40 mg/ml to about 50 mg/ml, about 40 mg/ml to about 55 mg/ml, about 40 mg/ml to about 60 mg/ml, about 40 mg/ml to about 65 mg/ml, about 40 mg/ml to about 70 mg/ml, about 40 mg/ml to about 100 mg/ml, about 45 mg/ml to about 50 mg/ml, about 45 mg/ml to about 55 mg/ml, about 45 mg/ml to about 60 mg/ml, about 45 mg/ml to about 65 mg/ml, about 45 mg/ml to about 70 mg/ml, about 45 mg/ml to about 100 mg/ml, about 50 mg/ml to about 55 mg/ml, about 50 mg/ml to about 60 mg/ml, about 50 mg/ml to about 65 mg/ml, about 50 mg/ml to about 70 mg/ml, about 50 mg/ml to about 100 mg/ml, about 55 mg/ml to about 60 mg/ml, about 55 mg/ml to about 65 mg/ml, about 55 mg/ml to about 70 mg/ml, about 55 mg/ml to about 100 mg/ml, about 60 mg/ml to about 65 mg/ml, about 60 mg/ml to about 70 mg/ml, about 60 mg/ml to about 100 mg/ml, about 65 mg/ml to about 70 mg/ml, about 65 mg/ml to about 100 mg/ml, or about 70 mg/ml to about 100 mg/ml. In some embodiments, the applicator delivers a naloxone containing formulation comprising naloxone HCl in the amount that is at most about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, or about 100 mg/ml. In some embodiments, the applicator delivers a naloxone containing formulation comprising naloxone HCl in the amount that is at most at least about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, or about 70 mg/ml. In some embodiments, the applicator delivers a naloxone containing formulation comprising naloxone HCl in the amount that is at most at most about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, or about 100 mg/ml.

In some embodiments, the applicator delivers a naloxone containing formulation comprising naloxone HCl in the amount that is at least about 20 mg/ml to about 100 mg/ml. In some embodiments, the applicator delivers a naloxone containing formulation comprising naloxone HCl in the amount that is at least about 20 mg/ml to about 25 mg/ml, about 20 mg/ml to about 30 mg/ml, about 20 mg/ml to about 35 mg/ml, about 20 mg/ml to about 40 mg/ml, about 20 mg/ml to about 45 mg/ml, about 20 mg/ml to about 50 mg/ml, about 20 mg/ml to about 55 mg/ml, about 20 mg/ml to about 60 mg/ml, about 20 mg/ml to about 65 mg/ml, about 20 mg/ml to about 70 mg/ml, about 20 mg/ml to about 100 mg/ml, about 25 mg/ml to about 30 mg/ml, about 25 mg/ml to about 35 mg/ml, about 25 mg/ml to about 40 mg/ml, about 25 mg/ml to about 45 mg/ml, about 25 mg/ml to about 50 mg/ml, about 25 mg/ml to about 55 mg/ml, about 25 mg/ml to about 60 mg/ml, about 25 mg/ml to about 65 mg/ml, about 25 mg/ml to about 70 mg/ml, about 25 mg/ml to about 100 mg/ml, about 30 mg/ml to about 35 mg/ml, about 30 mg/ml to about 40 mg/ml, about 30 mg/ml to about 45 mg/ml, about 30 mg/ml to about 50 mg/ml, about 30 mg/ml to about 55 mg/ml, about 30 mg/ml to about 60 mg/ml, about 30 mg/ml to about 65 mg/ml, about 30 mg/ml to about 70 mg/ml, about 30 mg/ml to about 100 mg/ml, about 35 mg/ml to about 40 mg/ml, about 35 mg/ml to about 45 mg/ml, about 35 mg/ml to about 50 mg/ml, about 35 mg/ml to about 55 mg/ml, about 35 mg/ml to about 60 mg/ml, about 35 mg/ml to about 65 mg/ml, about 35 mg/ml to about 70 mg/ml, about 35 mg/ml to about 100 mg/ml, about 40 mg/ml to about 45 mg/ml, about 40 mg/ml to about 50 mg/ml, about 40 mg/ml to about 55 mg/ml, about 40 mg/ml to about 60 mg/ml, about 40 mg/ml to about 65 mg/ml, about 40 mg/ml to about 70 mg/ml, about 40 mg/ml to about 100 mg/ml, about 45 mg/ml to about 50 mg/ml, about 45 mg/ml to about 55 mg/ml, about 45 mg/ml to about 60 mg/ml, about 45 mg/ml to about 65 mg/ml, about 45 mg/ml to about 70 mg/ml, about 45 mg/ml to about 100 mg/ml, about 50 mg/ml to about 55 mg/ml, about 50 mg/ml to about 60 mg/ml, about 50 mg/ml to about 65 mg/ml, about 50 mg/ml to about 70 mg/ml, about 50 mg/ml to about 100 mg/ml, about 55 mg/ml to about 60 mg/ml, about 55 mg/ml to about 65 mg/ml, about 55 mg/ml to about 70 mg/ml, about 55 mg/ml to about 100 mg/ml, about 60 mg/ml to about 65 mg/ml, about 60 mg/ml to about 70 mg/ml, about 60 mg/ml to about 100 mg/ml, about 65 mg/ml to about 70 mg/ml, about 65 mg/ml to about 100 mg/ml, or about 70 mg/ml to about 100 mg/ml. In some embodiments, the applicator delivers a naloxone containing formulation comprising naloxone HCl in the amount that is at least about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, or about 100 mg/ml. In some embodiments, the applicator 1 delivers a naloxone containing formulation comprising naloxone HCl in the amount that is at least at least about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, or about 70 mg/ml. In some embodiments, the applicator delivers a naloxone containing formulation comprising naloxone HCl in the amount that is at least at most about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, or about 100 mg/ml.

In some embodiments, the applicator can deliver the naloxone containing formulation while the individual is not breathing. In some embodiments, the applicator can deliver the naloxone containing formulation while the individual is not inhaling. In some embodiments, the applicator can deliver the naloxone containing formulation while the individual is inhaling. In some embodiments, the applicator can deliver the naloxone containing formulation while the individual is not exhaling. In some embodiments, the applicator can deliver the naloxone containing formulation while the individual is exhaling. In some embodiments, the applicator can continuously deliver the naloxone containing formulation to the individual until the individual regains consciousness.

In some embodiments, the applicator delivers the naloxone containing formulation to the individual when the individual is facing up. In some embodiments, the applicator delivers the naloxone containing formulation to the individual when the individual is facing down. In some embodiments, the applicator delivers the naloxone containing formulation to the individual when the individual is in an upright position. In some embodiments, the applicator delivers the naloxone containing formulation to the individual when the individual is in a prone position. In some embodiments, the applicator delivers the naloxone containing formulation to the individual when the individual is in a supine position. In some embodiments, the applicator delivers the naloxone containing formulation to the individual when individual's head is tilted forward. In some embodiments, the applicator delivers the naloxone containing formulation to the individual when individual's head is tilted backward.

In some embodiments, a therapeutically effective amount of naloxone to treat opioid overdose can be delivered at a lower dose by the applicator direct contacting and dispensing the naloxone containing formulation to the nasal passage compared to a dose delivered by a nasal spray. In some embodiments, the dose required to achieve the therapeutically effective amount of naloxone via the applicator direct contacting and dispensing naloxone to the nasal passage is lowered by at least 10%, 20%, 30%, 40%, 50%, or more compared to the dose required for the nasal spray to achieve the same therapeutically effective amount.

In some embodiments, a dose dispensed by the applicator direct contacting and dispensing the naloxone to the nasal passage can increase pharmacokinetics compared to the same dose dispensed by a nasal spray. In some cases, the pharmacokinetics can be increased by at least 10%, 20%, 30%, 40%, 50%, or more by the dose dispensed by the applicator direct contacting and dispensing the naloxone to the nasal passage compared to the same dose dispensed by nasal spray.

As described herein, in some embodiments, are devices for delivering naloxone containing formulation to an individual in need thereof. In some instances, the devices comprise the applicator, the cover, and the naloxone containing formulation as described herein. In some cases, the devices further comprise a thermal regulator. In some embodiments, the thermal regulator increases temperature of the naloxone containing formulation. In some embodiments, the thermal regulator increases the temperature of the naloxone containing formulation by at least 1 degree Celsius over an ambient temperature. In some embodiments, the thermal regulator increases the temperature of the naloxone containing formulation by at least 10 degrees Celsius over an ambient temperature. In some embodiments, the thermal regulator increases the temperature of the naloxone containing formulation to at least 37 degrees Celsius.

In some embodiments, the thermal regulator increases the temperature of the naloxone containing formulation to reduce viscosity of naloxone containing formulation prior to delivery by directly contacting the nasal passage or nasal cavity. In some embodiments, the thermal regulator increases the temperature of the naloxone containing formulation to reduce viscosity of naloxone containing formulation during the delivery by directly contacting the nasal passage or nasal cavity. In some embodiments, the thermal regulator increases the temperature of the naloxone containing formulation to reduce viscosity of naloxone containing formulation upon completion of the delivery by directly contacting the nasal passage or nasal cavity. In some embodiments, the thermal regulator increases the temperature of the naloxone containing formulation to reduce viscosity of naloxone containing formulation during the delivery by directly contacting the nasal passage or nasal cavity. In some embodiments, the thermal regulator increases the temperature of the naloxone containing formulation to reduce viscosity of naloxone containing formulation upon completion of the delivery by directly contacting the nasal passage or nasal cavity.

In some embodiments, the thermal regulator increases the temperature of the naloxone containing formulation to facilitate gelling of naloxone containing formulation prior to delivery by directly contacting the nasal passage or nasal cavity. In some embodiments, the thermal regulator increases the temperature of the naloxone containing formulation to facilitate gelling of naloxone containing formulation during the delivery by directly contacting the nasal passage or nasal cavity. In some embodiments, the thermal regulator increases the temperature of the naloxone containing formulation to facilitate gelling of naloxone containing formulation upon completion of the delivery by directly contacting the nasal passage or nasal cavity.

In some embodiments, the thermal regulator increases the temperature of the naloxone containing formulation to facilitate absorption of the naloxone HCl through the nasal passage or nasal cavity. In some embodiments, the thermal regulator increases the temperature of the naloxone containing formulation to increase pharmacokinetics or reduce the therapeutic effective amount of the naloxone HCl delivered to the nasal passage or nasal cavity.

In some embodiments, the thermal regulator decreases temperature of the naloxone containing formulation. In some embodiments, the thermal regulator decreases the temperature of the naloxone containing formulation by at least 1 degree Celsius over an ambient temperature. In some embodiments, the thermal regulator decreases the temperature of the naloxone containing formulation by at least 10 degrees Celsius over an ambient temperature. In some embodiments, the thermal regulator decreases the temperature of the naloxone containing formulation to at most 20 degrees Celsius.

In some embodiments, the thermal regulator decreases the temperature of the naloxone containing formulation to facilitate gelling of naloxone containing formulation prior to delivery by directly contacting the nasal passage or nasal cavity. In some embodiments, the thermal regulator decreases the temperature of the naloxone containing formulation to facilitate gelling of naloxone containing formulation during the delivery by directly contacting the nasal passage or nasal cavity. In some embodiments, the thermal regulator decreases the temperature of the naloxone containing formulation to facilitate gelling of naloxone containing formulation upon completion of the delivery by directly contacting the nasal passage or nasal cavity.

In some embodiments, the thermal regulator decreases the temperature of the naloxone containing formulation to facilitate absorption of the naloxone HCl through the nasal passage or nasal cavity. In some embodiments, the thermal regulator decreases the temperature of the naloxone containing formulation to increase pharmacokinetics or reduce the therapeutic effective amount of the naloxone HCl delivered to the nasal passage or nasal cavity.

Described herein, in some embodiments, are devices for delivering naloxone containing formulation to an individual in need thereof. In some embodiments, the devices comprise a humidity regulator. In some embodiments, the humidity regulators maintain a relative humidity of the devices about 20 RH % to about 75 RH %. In some embodiments, the humidity regulators maintain a relative humidity of the devices about 20 RH % to about 25 RH %, about 20 RH % to about 30 RH %, about 20 RH % to about 35 RH %, about 20 RH % to about 40 RH %, about 20 RH % to about 45 RH %, about 20 RH % to about 50 RH %, about 20 RH % to about 55 RH %, about 20 RH % to about 60 RH %, about 20 RH % to about 65 RH %, about 20 RH % to about 70 RH %, about 20 RH % to about 75 RH %, about 25 RH % to about 30 RH %, about 25 RH % to about 35 RH %, about 25 RH % to about 40 RH %, about 25 RH % to about 45 RH %, about 25 RH % to about 50 RH %, about 25 RH % to about 55 RH %, about 25 RH % to about 60 RH %, about 25 RH % to about 65 RH %, about 25 RH % to about 70 RH %, about 25 RH % to about 75 RH %, about 30 RH % to about 35 RH %, about 30 RH % to about 40 RH %, about 30 RH % to about 45 RH %, about 30 RH % to about 50 RH %, about 30 RH % to about 55 RH %, about 30 RH % to about 60 RH %, about 30 RH % to about 65 RH %, about 30 RH % to about 70 RH %, about 30 RH % to about 75 RH %, about 35 RH % to about 40 RH %, about 35 RH % to about 45 RH %, about 35 RH % to about 50 RH %, about 35 RH % to about 55 RH %, about 35 RH % to about 60 RH %, about 35 RH % to about 65 RH %, about 35 RH % to about 70 RH %, about 35 RH % to about 75 RH %, about 40 RH % to about 45 RH %, about 40 RH % to about 50 RH %, about 40 RH % to about 55 RH %, about 40 RH % to about 60 RH %, about 40 RH % to about 65 RH %, about 40 RH % to about 70 RH %, about 40 RH % to about 75 RH %, about 45 RH % to about 50 RH %, about 45 RH % to about 55 RH %, about 45 RH % to about 60 RH %, about 45 RH % to about 65 RH %, about 45 RH % to about 70 RH %, about 45 RH % to about 75 RH %, about 50 RH % to about 55 RH %, about 50 RH % to about 60 RH %, about 50 RH % to about 65 RH %, about 50 RH % to about 70 RH %, about 50 RH % to about 75 RH %, about 55 RH % to about 60 RH %, about 55 RH % to about 65 RH %, about 55 RH % to about 70 RH %, about 55 RH % to about 75 RH %, about 60 RH % to about 65 RH %, about 60 RH % to about 70 RH %, about 60 RH % to about 75 RH %, about 65 RH % to about 70 RH %, about 65 RH % to about 75 RH %, or about 70 RH % to about 75 RH %. In some embodiments, the humidity regulators maintain a relative humidity of the devices about 20 RH %, about 25 RH %, about 30 RH %, about 35 RH %, about 40 RH %, about 45 RH %, about 50 RH %, about 55 RH %, about 60 RH %, about 65 RH %, about 70 RH %, or about 75 RH %. In some embodiments, the humidity regulators maintain a relative humidity of the devices at least about 20 RH %, about 25 RH %, about 30 RH %, about 35 RH %, about 40 RH %, about 45 RH %, about 50 RH %, about 55 RH %, about 60 RH %, about 65 RH %, or about 70 RH %. In some embodiments, the humidity regulators maintain a relative humidity of the devices at most about 25 RH %, about 30 RH %, about 35 RH %, about 40 RH %, about 45 RH %, about 50 RH %, about 55 RH %, about 60 RH %, about 65 RH %, about 70 RH %, or about 75 RH %.

In some embodiments, the humidity regulators maintain a relative humidity of the environment inside the reservoirs about 20 RH % to about 75 RH %. In some embodiments, the humidity regulators maintain a relative humidity of the environment inside the reservoirs about 20 RH % to about 25 RH %, about 20 RH % to about 30 RH %, about 20 RH % to about 35 RH %, about 20 RH % to about 40 RH %, about 20 RH % to about 45 RH %, about 20 RH % to about 50 RH %, about 20 RH % to about 55 RH %, about 20 RH % to about 60 RH %, about 20 RH % to about 65 RH %, about 20 RH % to about 70 RH %, about 20 RH % to about 75 RH %, about 25 RH % to about 30 RH %, about 25 RH % to about 35 RH %, about 25 RH % to about 40 RH %, about 25 RH % to about 45 RH %, about 25 RH % to about 50 RH %, about 25 RH % to about 55 RH %, about 25 RH % to about 60 RH %, about 25 RH % to about 65 RH %, about 25 RH % to about 70 RH %, about 25 RH % to about 75 RH %, about 30 RH % to about 35 RH %, about 30 RH % to about 40 RH %, about 30 RH % to about 45 RH %, about 30 RH % to about 50 RH %, about 30 RH % to about 55 RH %, about 30 RH % to about 60 RH %, about 30 RH % to about 65 RH %, about 30 RH % to about 70 RH %, about 30 RH % to about 75 RH %, about 35 RH % to about 40 RH %, about 35 RH % to about 45 RH %, about 35 RH % to about 50 RH %, about 35 RH % to about 55 RH %, about 35 RH % to about 60 RH %, about 35 RH % to about 65 RH %, about 35 RH % to about 70 RH %, about 35 RH % to about 75 RH %, about 40 RH % to about 45 RH %, about 40 RH % to about 50 RH %, about 40 RH % to about 55 RH %, about 40 RH % to about 60 RH %, about 40 RH % to about 65 RH %, about 40 RH % to about 70 RH %, about 40 RH % to about 75 RH %, about 45 RH % to about 50 RH %, about 45 RH % to about 55 RH %, about 45 RH % to about 60 RH %, about 45 RH % to about 65 RH %, about 45 RH % to about 70 RH %, about 45 RH % to about 75 RH %, about 50 RH % to about 55 RH %, about 50 RH % to about 60 RH %, about 50 RH % to about 65 RH %, about 50 RH % to about 70 RH %, about 50 RH % to about 75 RH %, about 55 RH % to about 60 RH %, about 55 RH % to about 65 RH %, about 55 RH % to about 70 RH %, about 55 RH % to about 75 RH %, about 60 RH % to about 65 RH %, about 60 RH % to about 70 RH %, about 60 RH % to about 75 RH %, about 65 RH % to about 70 RH %, about 65 RH % to about 75 RH %, or about 70 RH % to about 75 RH %. In some embodiments, the humidity regulators maintain a relative humidity of the environment inside the reservoirs about 20 RH %, about 25 RH %, about 30 RH %, about 35 RH %, about 40 RH %, about 45 RH %, about 50 RH %, about 55 RH %, about 60 RH %, about 65 RH %, about 70 RH %, or about 75 RH %. In some embodiments, the humidity regulators maintain a relative humidity of the environment inside the reservoirs at least about 20 RH %, about 25 RH %, about 30 RH %, about 35 RH %, about 40 RH %, about 45 RH %, about 50 RH %, about 55 RH %, about 60 RH %, about 65 RH %, or about 70 RH %. In some embodiments, the humidity regulators maintain a relative humidity of the environment inside the reservoirs at most about 25 RH %, about 30 RH %, about 35 RH %, about 40 RH %, about 45 RH %, about 50 RH %, about 55 RH %, about 60 RH %, about 65 RH %, about 70 RH %, or about 75 RH %.

In some embodiments, the humidity regulators maintain a relative humidity of the environment inside the covers covering the applicators about 20 RH % to about 75 RH %. In some embodiments, the humidity regulators maintain a relative humidity of the environment inside the covers covering the applicators about 20 RH % to about 25 RH %, about 20 RH % to about 30 RH %, about 20 RH % to about 35 RH %, about 20 RH % to about 40 RH %, about 20 RH % to about 45 RH %, about 20 RH % to about 50 RH %, about 20 RH % to about 55 RH %, about 20 RH % to about 60 RH %, about 20 RH % to about 65 RH %, about 20 RH % to about 70 RH %, about 20 RH % to about 75 RH %, about 25 RH % to about 30 RH %, about 25 RH % to about 35 RH %, about 25 RH % to about 40 RH %, about 25 RH % to about 45 RH %, about 25 RH % to about 50 RH %, about 25 RH % to about 55 RH %, about 25 RH % to about 60 RH %, about 25 RH % to about 65 RH %, about 25 RH % to about 70 RH %, about 25 RH % to about 75 RH %, about 30 RH % to about 35 RH %, about 30 RH % to about 40 RH %, about 30 RH % to about 45 RH %, about 30 RH % to about 50 RH %, about 30 RH % to about 55 RH %, about 30 RH % to about 60 RH %, about 30 RH % to about 65 RH %, about 30 RH % to about 70 RH %, about 30 RH % to about 75 RH %, about 35 RH % to about 40 RH %, about 35 RH % to about 45 RH %, about 35 RH % to about 50 RH %, about 35 RH % to about 55 RH %, about 35 RH % to about 60 RH %, about 35 RH % to about 65 RH %, about 35 RH % to about 70 RH %, about 35 RH % to about 75 RH %, about 40 RH % to about 45 RH %, about 40 RH % to about 50 RH %, about 40 RH % to about 55 RH %, about 40 RH % to about 60 RH %, about 40 RH % to about 65 RH %, about 40 RH % to about 70 RH %, about 40 RH % to about 75 RH %, about 45 RH % to about 50 RH %, about 45 RH % to about 55 RH %, about 45 RH % to about 60 RH %, about 45 RH % to about 65 RH %, about 45 RH % to about 70 RH %, about 45 RH % to about 75 RH %, about 50 RH % to about 55 RH %, about 50 RH % to about 60 RH %, about 50 RH % to about 65 RH %, about 50 RH % to about 70 RH %, about 50 RH % to about 75 RH %, about 55 RH % to about 60 RH %, about 55 RH % to about 65 RH %, about 55 RH % to about 70 RH %, about 55 RH % to about 75 RH %, about 60 RH % to about 65 RH %, about 60 RH % to about 70 RH %, about 60 RH % to about 75 RH %, about 65 RH % to about 70 RH %, about 65 RH % to about 75 RH %, or about 70 RH % to about 75 RH %. In some embodiments, the humidity regulators maintain a relative humidity of the environment inside the covers covering the applicators about 20 RH %, about 25 RH %, about 30 RH %, about 35 RH %, about 40 RH %, about 45 RH %, about 50 RH %, about 55 RH %, about 60 RH %, about 65 RH %, about 70 RH %, or about 75 RH %. In some embodiments, the humidity regulators maintain a relative humidity of the environment inside the covers covering the applicators at least about 20 RH %, about 25 RH %, about 30 RH %, about 35 RH %, about 40 RH %, about 45 RH %, about 50 RH %, about 55 RH %, about 60 RH %, about 65 RH %, or about 70 RH %. In some embodiments, the humidity regulators maintain a relative humidity of the environment inside the covers covering the applicators at most about 25 RH %, about 30 RH %, about 35 RH %, about 40 RH %, about 45 RH %, about 50 RH %, about 55 RH %, about 60 RH %, about 65 RH %, about 70 RH %, or about 75 RH %.

In some embodiments, the humidity regulators maintain a relative humidity of the environment of the applicators about 20 RH % to about 75 RH %. In some embodiments, the humidity regulators maintain a relative humidity of the environment of the applicators about 20 RH % to about 25 RH %, about 20 RH % to about 30 RH %, about 20 RH % to about 35 RH %, about 20 RH % to about 40 RH %, about 20 RH % to about 45 RH %, about 20 RH % to about 50 RH %, about 20 RH % to about 55 RH %, about 20 RH % to about 60 RH %, about 20 RH % to about 65 RH %, about 20 RH % to about 70 RH %, about 20 RH % to about 75 RH %, about 25 RH % to about 30 RH %, about 25 RH % to about 35 RH %, about 25 RH % to about 40 RH %, about 25 RH % to about 45 RH %, about 25 RH % to about 50 RH %, about 25 RH % to about 55 RH %, about 25 RH % to about 60 RH %, about 25 RH % to about 65 RH %, about 25 RH % to about 70 RH %, about 25 RH % to about 75 RH %, about 30 RH % to about 35 RH %, about 30 RH % to about 40 RH %, about 30 RH % to about 45 RH %, about 30 RH % to about 50 RH %, about 30 RH % to about 55 RH %, about 30 RH % to about 60 RH %, about 30 RH % to about 65 RH %, about 30 RH % to about 70 RH %, about 30 RH % to about 75 RH %, about 35 RH % to about 40 RH %, about 35 RH % to about 45 RH %, about 35 RH % to about 50 RH %, about 35 RH % to about 55 RH %, about 35 RH % to about 60 RH %, about 35 RH % to about 65 RH %, about 35 RH % to about 70 RH %, about 35 RH % to about 75 RH %, about 40 RH % to about 45 RH %, about 40 RH % to about 50 RH %, about 40 RH % to about 55 RH %, about 40 RH % to about 60 RH %, about 40 RH % to about 65 RH %, about 40 RH % to about 70 RH %, about 40 RH % to about 75 RH %, about 45 RH % to about 50 RH %, about 45 RH % to about 55 RH %, about 45 RH % to about 60 RH %, about 45 RH % to about 65 RH %, about 45 RH % to about 70 RH %, about 45 RH % to about 75 RH %, about 50 RH % to about 55 RH %, about 50 RH % to about 60 RH %, about 50 RH % to about 65 RH %, about 50 RH % to about 70 RH %, about 50 RH % to about 75 RH %, about 55 RH % to about 60 RH %, about 55 RH % to about 65 RH %, about 55 RH % to about 70 RH %, about 55 RH % to about 75 RH %, about 60 RH % to about 65 RH %, about 60 RH % to about 70 RH %, about 60 RH % to about 75 RH %, about 65 RH % to about 70 RH %, about 65 RH % to about 75 RH %, or about 70 RH % to about 75 RH %. In some embodiments, the humidity regulators maintain a relative humidity of the environment of the applicators about 20 RH %, about 25 RH %, about 30 RH %, about 35 RH %, about 40 RH %, about 45 RH %, about 50 RH %, about 55 RH %, about 60 RH %, about 65 RH %, about 70 RH %, or about 75 RH %. In some embodiments, the humidity regulators maintain a relative humidity of the environment of the applicators at least about 20 RH %, about 25 RH %, about 30 RH %, about 35 RH %, about 40 RH %, about 45 RH %, about 50 RH %, about 55 RH %, about 60 RH %, about 65 RH %, or about 70 RH %. In some embodiments, the humidity regulators maintain a relative humidity of the environment of the applicators at most about 25 RH %, about 30 RH %, about 35 RH %, about 40 RH %, about 45 RH %, about 50 RH %, about 55 RH %, about 60 RH %, about 65 RH %, about 70 RH %, or about 75 RH %.

Methods

Described herein, in some embodiments, is method for delivering a naloxone containing formulation to nasal passage or nasal cavity of an individual, the method comprising: receiving a delivery device comprising an applicator, a cover, the naloxone containing formulation, wherein the naloxone containing formulation is held by a surface of the applicator; and inserting the delivery device into the nasal passage or nasal cavity of the individual so that the surface of the applicator upon which the naloxone containing formulation is held contacts a surface of the nasal passage or nasal cavity.

Referencing FIG. 1-17, in some embodiments, the method can comprise receiving a device, said device comprising an applicator 1; a cover 3; and the naloxone containing formulation; inserting the device into the nasal passage or nasal cavity of the individual; and contacting a surface of the nasal passage or nasal cavity of the individual with the applicator 1, thereby delivering the naloxone containing formulation from the applicator to the surface of the nasal passage or nasal cavity by direct contact of the applicator and the surface of the nasal passage or nasal cavity In some embodiments, the method can comprise breaking or disconnecting the engagement 4 by disconnecting the first engagement part 6 located on the cover 3 from the second engagement part 7 located on the applicator 1 prior to using the devices to deliver the naloxone containing formulation.

In some embodiments, the method can comprise breaking the seal of the cover 3 prior to using the devices to deliver the naloxone containing formulation. In some embodiments, the method can comprise breaking the seal of the cover 3 during the use of the devices delivering the naloxone containing formulation. In some embodiments, the method can comprise breaking the seal of the applicator 1. In some embodiments, the method can comprise breaking the seal of the applicator 1 prior to using the devices to deliver the naloxone containing formulation. In some embodiments, the method can comprise breaking the seal of the applicator 1 during the use of the devices delivering the naloxone containing formulation. In some embodiments, the methods comprise breaking the adhesive bond between the applicator 1 and the cover 3. In some embodiments, the methods comprise breaking the adhesive bond between the applicator 1 and the cover 3 prior to using the devices to deliver the naloxone containing formulation. In some embodiments, the method can comprise breaking the adhesive bond between the applicator 1 and the cover 3 during the use of the devices delivering the naloxone containing formulation. In some embodiments, the method can comprise breaking the engagement 4 in the form of a frangible connection prior to using the devices for delivering the naloxone containing formulation.

Figure 12:
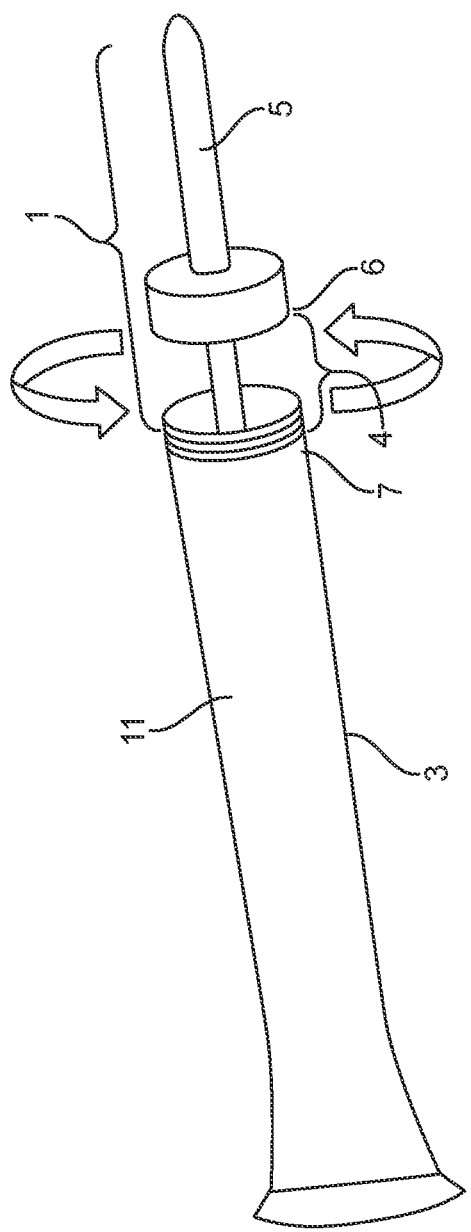
FIG. 12 illustrates the device comprising an applicator for delivering a pharmaceutical composition by directly contacting the nasal swab on the tip of the applicator to the nasal passage or nasal cavity of an individual who is in need of the pharmaceutical composition.

In some embodiments, the naloxone containing formulation is delivered to mucosal membrane of the nasal passage or nasal cavity of the individual. In some embodiments, the naloxone containing formulation is delivered to mucosal membrane of the nasal passage or nasal cavity of the individual by directly contacting the applicator of the device with the mucosal membrane of the nasal passage or nasal cavity. In some embodiments, the applicator 1 comprises a nasal trumpet (FIG. 13), where the nasal trumpet has a conical shape and is curved along its longitudinal axis so that it conforms to the anatomy of the nasal passage or nasal cavity. In some embodiments, the applicator 1 comprises a nasal swab (FIG. 12). In some embodiments, the applicator 1 comprises a nasal swab on the tip of the applicator. In some embodiments, the applicator comprises absorbent material such as cotton. In some embodiments, the applicator 1 comprises roll-on or roller-ball (FIG. 14). In some embodiments, the applicator comprises balm (FIG. 15). In some embodiments, the applicator comprises delivering the naloxone containing formulation by either the shaft 8 of the stick dispenser of the applicator, the tip 9 of the stick dispenser of the applicator, or both the shaft 8 and the tip 9 of the applicator 1 (FIG. 16). In some embodiments, the applicator tip 9 contacts a mucosa anywhere along the nasal passage. In some embodiments, the applicator tip 9 contacts a mucosa of the nasal passage 1.5-3 cm from the nasal opening. In some embodiments, the applicator tip 9 contacts a mucosa of the nasal passage 1.5-2.0 cm from the nasal opening. In some embodiments, the applicator tip 9 contacts a mucosa of the nasal passage 1.0-1.5 cm from the nasal opening. In some embodiments, the applicator tip 9 contacts a mucosa of the nasal passage 0.5-1.0 cm from the nasal opening. In some embodiments, the method can comprise the applicator delivering a pre-metered amount or volume of the naloxone containing formulation. In some embodiments, the amount or volume of the naloxone containing formulation is pre-metered by the housing of the reservoir 11 in the cover 3. In some embodiments, the amount or volume of the naloxone containing formulation is pre-metered by the housing of the reservoir 11 in the applicator 1. In some embodiments, the amount or volume of the naloxone containing formulation is pre-metered by the housing of the applicator. In some embodiments, the amount or volume of the naloxone containing formulation is pre-metered by the shaft 8 of the applicator 1. In some embodiments, the amount or volume of the naloxone containing formulation is pre-metered by the tip 9 of the applicator 1.

Figure 22:
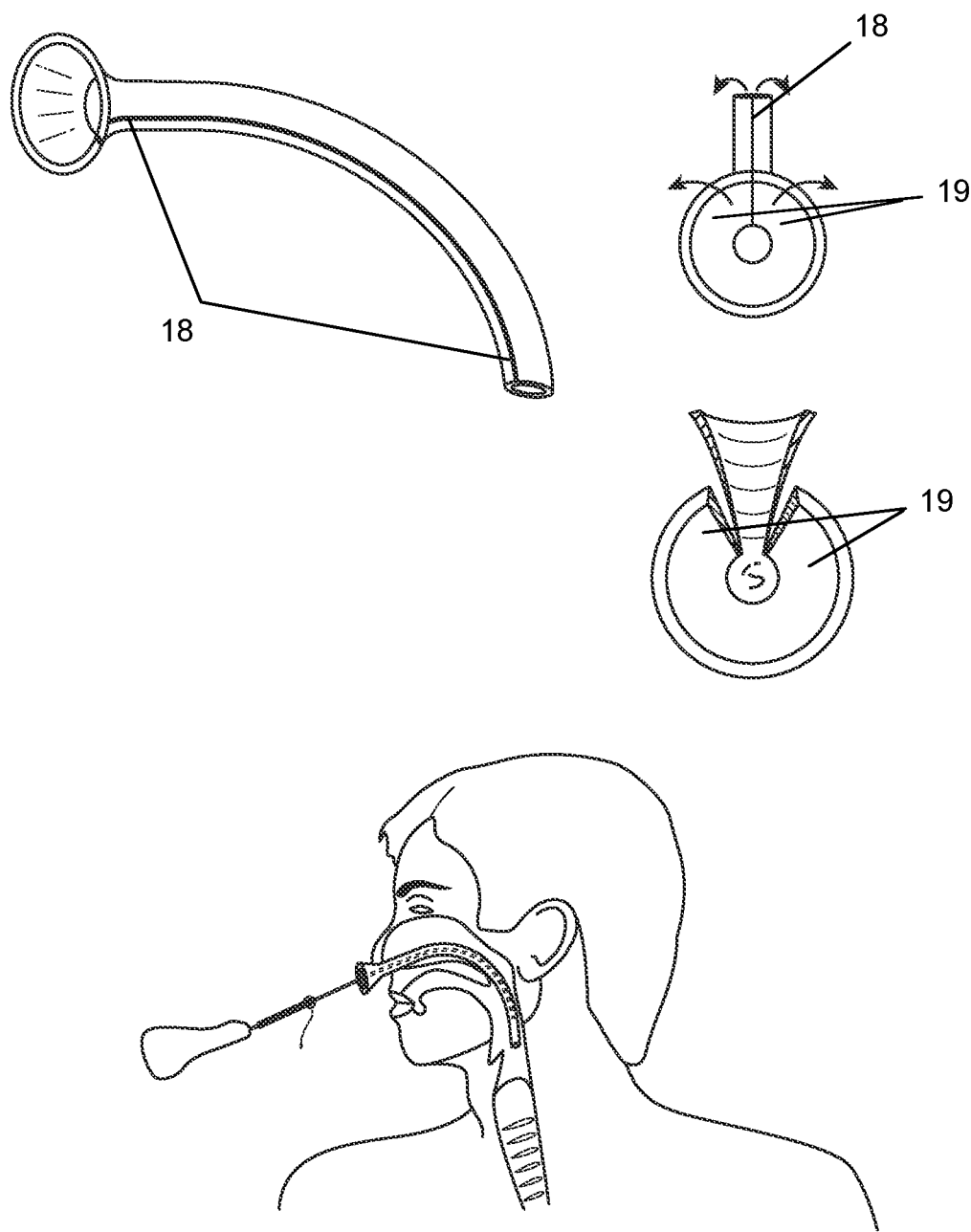
FIG. 22 illustrates a nasal trumpet comprising a slit that runs along a longitudinal axis of the nasal trumpet. The slit can be opened or closed to accommodate insertion or removal of fiberoptic scopes or endotracheal tubes during endotracheal intubation.

Described herein, in some embodiments, is a method of using the nasal trumpet as illustrated in FIGS. 18-23. In some embodiments, the method comprising delivering a naloxone containing formulation to nasal passage of an individual by direct contact of the tubular member of the applicator 1 with the surface of the nasal cavity or the nasal passage of the individual. In some embodiments, the naloxone containing formulation can be delivered via at least one opening 16 on the tubular member. In some cases, the method can comprise inserting a fiberoptic scope coupled to a endotracheal tube via the at least one lumen of the nasal trumpet as shown in FIG. 22. In some cases, the nasal trumpet comprises a slit 18, which allows the removal of the nasal trumpet while both the nasal trumpet and the fiberoptic scope are at least partially inserted into the nasal cavity or the nasal passage of the individual. In some cases, the method can comprise inserting the nasal trumpet into the nasal passage; the nasal trumpet dispensing the naloxone containing formulation; inserting the fiberoptic scope pre-loaded with the endotracheal tube through the nasal trumpet into the nasal passage to the back of oropharynx; removing the nasal trumpet via the slit 18; and inserting the endotracheal tube further down to prop open the depressed nasal passage. In some instances, the method can comprise inserting the nasal trumpet and the fiberoptic scope before the nasal trumpet delivering the naloxone containing formulation. In some instances, the method can comprise inserting the nasal trumpet and the fiberoptic scope after the nasal trumpet delivering the naloxone containing formulation. In some embodiments, method described herein can comprise using the nasal trumpet with slit 18 as a guide for the insertion of the fiberoptic scope pre-loaded with the endotracheal tube. In some embodiments, the use of the nasal trumpet with slit 18 can reduce trauma or damages to the nasal mucosa or nasal tissues during the insertion of the fiberoptic scope pre-loaded with the endotracheal tube. In some embodiments, the use of the nasal trumpet with slit 18 can reduce trauma or damages to the nasal mucosa or nasal tissues during endotracheal intubation.

In some embodiments, the method can comprise the use of an inflatable cuff 20 (FIG. 23) to expand the nasal passage. In embodiments, the inflatable cuff can be expanded before, during, or after the delivery of the naloxone containing formulation. In some cases, the inflatable cuff 20 can expand in the depressed nasal passage to allow the insertion of the endotracheal tube during endotracheal intubation. In some embodiments, the use of inflatable cuff 20 can reduce trauma or damages to the nasal mucosa or nasal tissues during endotracheal intubation. In some embodiments, the method described herein can comprise the use of both slit 18 and inflatable cuff 20 to reduce trauma or damages to the nasal mucosa or nasal tissues during endotracheal intubation.

In some embodiments, the method can deliver a pre-metered amount or volume of the naloxone containing formulation that is stored in the reservoir of the cover. In some embodiments, the methods deliver a pre-metered amount or volume of the naloxone containing formulation that is stored in the reservoir of the applicator. In some embodiments, the methods deliver a pre-metered amount or volume of the naloxone containing formulation that is stored in the nasal trumpet. In some embodiments, the methods deliver a pre-metered amount or volume of the naloxone containing formulation that is stored on the surface of the nasal trumpet. In some embodiments, the methods deliver a pre-metered amount or volume of the naloxone containing formulation that is stored by the absorbance of the nasal swab. In some embodiments, the methods deliver a pre-metered amount or volume of the naloxone containing formulation that is stored in the roller-ball or roll-on of the applicator. In some embodiments, the methods deliver a pre-metered amount or volume of the naloxone containing formulation that is stored in the balm of the applicator. In some embodiments, the methods deliver a pre-metered amount or volume of the naloxone containing formulation that is stored on the surface of the balm of the applicator. In some embodiments, the methods deliver a pre-metered amount or volume of the naloxone containing formulation that is stored in the shaft of the applicator. In some embodiments, the methods deliver a pre-metered amount or volume of the naloxone containing formulation that is stored on the surface of the shaft of the applicator. In some embodiments, the methods deliver a pre-metered amount or volume of the naloxone containing formulation that is stored in the tip of the applicator. In some embodiments, the methods deliver a pre-metered amount or volume of the naloxone containing formulation that is stored on the surface of the tip of the applicator.

In some embodiments, the methods described herein comprise delivering a naloxone containing formulation comprising at least one additional active ingredient, said at least one additional active ingredient is not naloxone hydrochloride. In some embodiments, the at least one more active ingredient comprises a respiratory stimulant. In some embodiments, the at least one more active ingredient comprises a cardiac stimulant. In some embodiments, the at least one more active ingredient comprises a nervous system stimulant. In some embodiments, the at least one more active ingredient narrows blood vessels and decreases blood flow. In some embodiments, the at least one more active ingredient dilates or increases blood vessels and increases blood flow. Examples of active ingredients that dilates or increases blood vessels and increase blood flow in the nasal passages or nasal cavities can include nitroprusside, phentolamine, or nifedipine. Other non-limiting examples of the at least one additional active ingredient include alpha-adrenoceptor agonists, vasopressin analogs, epinephrine, norepinephrine, phenylephrine, dopamine, dobutamine, serotonin 5-hydroxytryptamine agonists, triptans, nitroglycerin, alprostadil, riociguat, hydralazine, minoxidil, nesiritide, nitroprusside, doxapram, nikethamide, picrotoxin, pentylene tetrazol, bemegride, methyl xanthine derivatives, caffeine, aminophylline, nalorphine, levallorphan, diprenorphine, adrenaline, amrinone, angiotensinamide, antihypotensive agent, arbutamine, bufalin, cafedrine, dimetofrinem, dopexamine, enoximone, etilefrine, mephentermine, meta-hydroxynorephedrine, metaraminol, methamphetamine, midodrine, norfenefrine, prenalterol, theodrenaline, and xamoterol.

In some embodiments, the methods described herein comprise delivering a naloxone containing formulation comprising an aqueous formulation. In some embodiments, the methods described herein comprise delivering a naloxone containing formulation comprising a gel formulation. In some embodiments, the methods described herein comprise delivering a naloxone containing formulation comprising a semi-solid formulation. In some embodiments, the methods described herein comprise delivering a naloxone containing formulation comprising a solid formulation. In some embodiments, the methods described herein comprise delivering a naloxone containing formulation comprising a powder formulation, said powder formulation comprises powder naloxone hydrochloride.

In some embodiments, the methods described herein comprise delivering the naloxone containing formulation with the devices described herein while the individual is not breathing. In some embodiments, the methods comprise delivering the naloxone containing formulation with the devices described herein while the individual is not inhaling. In some embodiments, the methods comprise delivering the naloxone containing formulation with the devices described herein while the individual is inhaling. In some embodiments, the methods comprise delivering the naloxone containing formulation with the devices described herein while the individual is not exhaling. In some embodiments, the methods comprise delivering the naloxone containing formulation with the devices described herein while the individual is exhaling. In some embodiments, the methods comprise delivering the naloxone containing formulation with the devices described herein until the individual regains consciousness.

In some embodiments, the methods comprise delivering the naloxone containing formulation with the devices described herein to the individual when the individual is facing up. In some embodiments, the methods comprise delivering the naloxone containing formulation with the devices described herein to the individual when the individual is facing down. In some embodiments, the methods comprise delivering the naloxone containing formulation with the devices described herein to the individual when the individual is in an upright position. In some embodiments, the methods comprise delivering the naloxone containing formulation with the devices described herein to the individual when the individual is in a prone position. In some embodiments, the methods comprise delivering the naloxone containing formulation with the devices described herein to the individual when the individual is in a supine position. In some embodiments, the methods comprise delivering the naloxone containing formulation with the devices described herein to the individual when individual's head is tilted forward. In some embodiments, the methods comprise delivering the naloxone containing formulation with the devices described herein to the individual when individual's head is tilted backward.

In some embodiments, the methods described herein comprise delivering the naloxone containing formulation with the devices, where the applicator completes delivering the naloxone containing formulation within 1 second. In some embodiments, the methods described herein comprise delivering the naloxone containing formulation with the devices, where the applicator completes delivering the naloxone containing formulation after at least 1 second. In some embodiments, the methods described herein comprise delivering the naloxone containing formulation with the devices, where the applicator completes delivering the naloxone containing formulation after at least 5 seconds. In some embodiments, the methods described herein comprise delivering the naloxone containing formulation with the devices, where the applicator completes delivering the naloxone containing formulation after at least 30 seconds. In some embodiments, the methods described herein comprise delivering the naloxone containing formulation with the devices, where the applicator completes delivering the naloxone containing formulation after at least one minute. In some embodiments, the methods described herein comprise delivering the naloxone containing formulation with the devices, where the applicator completes delivering the naloxone containing formulation after at least five minutes.

In some embodiments, the pharmacokinetics are increased in individuals who receive the naloxone containing formulation via the methods and devices described herein compared to individuals who receive the same dosage of naloxone dispensed by nasal spray. In some embodiments, the therapeutically effective amount is decreased for individuals who receive the naloxone containing formulation via the methods and devices described herein compared to individuals who receive the same dosage of naloxone dispensed by nasal spray.

In some embodiments, the methods described herein comprise delivering the naloxone containing formulation where the temperature of the naloxone containing formulation is increased by at least 1 degree Celsius over an ambient temperature. In some embodiments, the methods described herein comprise delivering the naloxone containing formulation where the temperature of the naloxone containing formulation is increased by at least 10 degrees Celsius over an ambient temperature. In some embodiments, the methods described herein comprise delivering the naloxone containing formulation where the temperature of the naloxone containing formulation is at about 37 degrees Celsius. In some embodiments, the methods described herein comprise delivering the naloxone containing formulation where the temperature of the naloxone containing formulation is at least 37 degrees Celsius. In some embodiments, the methods described herein comprise delivering the naloxone containing formulation where the temperature of the naloxone containing formulation is decreased by at least 1 degree Celsius under an ambient temperature. In some embodiments, the methods described herein comprise delivering the naloxone containing formulation where the temperature of the naloxone containing formulation is decreased by at least 10 degrees Celsius under an ambient temperature.

In some embodiments, the methods described herein comprise delivering the naloxone containing formulation to treat opioid overdose in an individual. In some embodiments, the methods described herein comprise delivering the naloxone containing formulation to treat symptoms of opioid overdose in an individual. In some embodiments, the methods described herein comprise delivering the naloxone containing formulation to treat depression of respiration in an individual. In some embodiments, the methods described herein comprise delivering the naloxone containing formulation to treat depression of cardiac function in an individual. In some embodiments, the methods described herein comprise delivering the naloxone containing formulation to treat depression of function of nerve systems in an individual. In some embodiments, the methods described herein comprise delivering the naloxone containing formulation to treat addictive disorders in an individual. In some embodiments, the addictive disorders can be at least partially contributed by activities associated with opioid receptors. In some cases, the addictive disorders that can be treated by the methods described herein can include gambling disorder. In some embodiments, the methods described herein comprise delivering the naloxone containing formulation to treat chronic pain or constipation. In some embodiments, the methods described herein comprise delivering the naloxone containing formulation to treat chronic pain or constipation induced by opioid use.

Described herein, in some embodiments, are methods for delivering a naloxone containing formulation by direct contacting the applicator of the devices as described herein to the nasal passage or nasal cavity of an individual in need thereof. In some embodiments, the methods of delivering the naloxone containing formulation with the devices described herein increases pharmacokinetics compared to delivering the same naloxone containing formulation by nasal sprays.

In some embodiments, the methods of delivering the naloxone containing formulation with the devices described herein increases AUC compared to delivering the same naloxone containing formulation by nasal sprays. In some embodiments, the methods of delivering the naloxone containing formulation with the devices described herein increases AUC compared to delivering the same naloxone containing formulation by nasal sprays by at least 10%, 20%, 50%, 100%, 200%, 5 folds, 10 folds, or 50 folds. In some embodiments, the methods of delivering the naloxone containing formulation with the devices described herein increases C max compared to delivering the same naloxone containing formulation by nasal sprays. In some embodiments, the methods of delivering the naloxone containing formulation with the devices described herein increases C max compared to delivering the same naloxone containing formulation by nasal sprays by at least 10%, 20%, 50%, 100%, 200%, 5 folds, 10 folds, or 50 folds. In some embodiments, the methods of delivering the naloxone containing formulation with the devices described herein decreases T max compared to delivering the same naloxone containing formulation by nasal sprays. In some embodiments, the methods of delivering the naloxone containing formulation with the devices described herein decreases T max compared to delivering the same naloxone containing formulation by nasal sprays by at least 10%, 20%, 50%, 100%, 200%, 5 folds, 10 folds, or 50 folds.

Pharmaceutical Compositions

A pharmaceutical composition, as used herein, refers to a mixture of therapeutic or active agents, with other substances or compounds (i.e. pharmaceutically acceptable inactive ingredients), such as carriers, salts, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. Optionally, the compositions include two or more therapeutic agent (e.g., one or more therapeutic agents and one or more additional agents) as discussed herein. In practicing the methods of treatment or use provided herein, therapeutically effective amounts of therapeutic or active agents described herein are administered in a pharmaceutical composition to a mammal having a disease, disorder, or condition to be treated, e.g., opioid overdose or symptoms stemmed from opioid overdose. A therapeutically effective amount can vary widely depending on the severity of the opioid overdose, the age and relative health of the individual, the potency of the therapeutic agent used and other factors. The therapeutic agents can be used singly or in combination with one or more therapeutic agents as components of mixtures.

In some cases, the pharmaceutical compositions described herein can comprise naloxone containing formulations for treating opioid overdose or symptoms associated with opioid overdose. In some cases, the naloxone containing formulation can treat depression of respiration in an individual. In some embodiments, the naloxone containing formulation can treat depression of cardiac function in an individual. In some embodiments, the naloxone containing formulation can treat depression of function of nerve systems in an individual. In some embodiments, the naloxone containing formulation can treat addictive disorders in an individual. In some embodiments, the addictive disorders can be at least partially contributed by activities associated with opioid receptors. In some embodiments, the addictive disorders that can be treated by the naloxone containing formulation described herein can include gambling disorder. In some embodiments, the naloxone containing formulation can treat chronic pain or constipation. In some embodiments, the naloxone containing formulation can treat chronic pain or constipation induced by opioid use.

The pharmaceutical compositions described herein are administered to an individual by appropriate administration routes, including but not limited to, intravenous, intraarterial, oral, parenteral, buccal, topical, transdermal, rectal, intramuscular, subcutaneous, intraosseous, transmucosal, inhalation, or intraperitoneal administration routes. In some embodiments, the pharmaceutical formulations can be administered intranasally to the individual. In some embodiments, the pharmaceutical compositions can be administered by directly contacting the pharmaceutical compositions to the nasal mucosal membrane in the nasal cavity of the individual.

In some embodiments, the pharmaceutical compositions described herein comprises an active or therapeutic agent comprising at least one opioid antagonist. In some cases, the opioid antagonist is selected from naloxone, naltrexone, nalmefene, diprenorphine, nalorphine, nalorphine dinicotinate, levallorphan, samidorphan, nalodeine, 6β-naltrexol, axelopran, bevenopran, methylsamidorphan, or naldemedine. In some embodiments, the pharmaceutical compositions described herein are naloxone containing formulations.

In some embodiments, the pharmaceutical compositions comprise opioid antagonists between at least about 20 mg/ml to about 70 mg/ml. In some embodiments, the pharmaceutical compositions comprise opioid antagonists between at least about 20 mg/ml to about 25 mg/ml, about 20 mg/ml to about 30 mg/ml, about 20 mg/ml to about 35 mg/ml, about 20 mg/ml to about 40 mg/ml, about 20 mg/ml to about 45 mg/ml, about 20 mg/ml to about 50 mg/ml, about 20 mg/ml to about 55 mg/ml, about 20 mg/ml to about 60 mg/ml, about 20 mg/ml to about 65 mg/ml, about 20 mg/ml to about 70 mg/ml, about 25 mg/ml to about 30 mg/ml, about 25 mg/ml to about 35 mg/ml, about 25 mg/ml to about 40 mg/ml, about 25 mg/ml to about 45 mg/ml, about 25 mg/ml to about 50 mg/ml, about 25 mg/ml to about 55 mg/ml, about 25 mg/ml to about 60 mg/ml, about 25 mg/ml to about 65 mg/ml, about 25 mg/ml to about 70 mg/ml, about 30 mg/ml to about 35 mg/ml, about 30 mg/ml to about 40 mg/ml, about 30 mg/ml to about 45 mg/ml, about 30 mg/ml to about 50 mg/ml, about 30 mg/ml to about 55 mg/ml, about 30 mg/ml to about 60 mg/ml, about 30 mg/ml to about 65 mg/ml, about 30 mg/ml to about 70 mg/ml, about 35 mg/ml to about 40 mg/ml, about 35 mg/ml to about 45 mg/ml, about 35 mg/ml to about 50 mg/ml, about 35 mg/ml to about 55 mg/ml, about 35 mg/ml to about 60 mg/ml, about 35 mg/ml to about 65 mg/ml, about 35 mg/ml to about 70 mg/ml, about 40 mg/ml to about 45 mg/ml, about 40 mg/ml to about 50 mg/ml, about 40 mg/ml to about 55 mg/ml, about 40 mg/ml to about 60 mg/ml, about 40 mg/ml to about 65 mg/ml, about 40 mg/ml to about 70 mg/ml, about 45 mg/ml to about 50 mg/ml, about 45 mg/ml to about 55 mg/ml, about 45 mg/ml to about 60 mg/ml, about 45 mg/ml to about 65 mg/ml, about 45 mg/ml to about 70 mg/ml, about 50 mg/ml to about 55 mg/ml, about 50 mg/ml to about 60 mg/ml, about 50 mg/ml to about 65 mg/ml, about 50 mg/ml to about 70 mg/ml, about 55 mg/ml to about 60 mg/ml, about 55 mg/ml to about 65 mg/ml, about 55 mg/ml to about 70 mg/ml, about 60 mg/ml to about 65 mg/ml, about 60 mg/ml to about 70 mg/ml, or about 65 mg/ml to about 70 mg/ml. In some embodiments, the pharmaceutical compositions comprise opioid antagonists between at least about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, or about 70 mg/ml. In some embodiments, the pharmaceutical compositions comprise opioid antagonists between at least at least about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, or about 65 mg/ml. In some embodiments, the pharmaceutical compositions comprise opioid antagonists between at least at most about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, or about 70 mg/ml.

In some embodiments, the pharmaceutical compositions comprise naloxone between about 20 mg/ml to about 70 mg/ml. In some embodiments, the pharmaceutical compositions comprise naloxone between about 20 mg/ml to about 25 mg/ml, about 20 mg/ml to about 30 mg/ml, about 20 mg/ml to about 35 mg/ml, about 20 mg/ml to about 40 mg/ml, about 20 mg/ml to about 45 mg/ml, about 20 mg/ml to about 50 mg/ml, about 20 mg/ml to about 55 mg/ml, about 20 mg/ml to about 60 mg/ml, about 20 mg/ml to about 65 mg/ml, about 20 mg/ml to about 70 mg/ml, about 25 mg/ml to about 30 mg/ml, about 25 mg/ml to about 35 mg/ml, about 25 mg/ml to about 40 mg/ml, about 25 mg/ml to about 45 mg/ml, about 25 mg/ml to about 50 mg/ml, about 25 mg/ml to about 55 mg/ml, about 25 mg/ml to about 60 mg/ml, about 25 mg/ml to about 65 mg/ml, about 25 mg/ml to about 70 mg/ml, about 30 mg/ml to about 35 mg/ml, about 30 mg/ml to about 40 mg/ml, about 30 mg/ml to about 45 mg/ml, about 30 mg/ml to about 50 mg/ml, about 30 mg/ml to about 55 mg/ml, about 30 mg/ml to about 60 mg/ml, about 30 mg/ml to about 65 mg/ml, about 30 mg/ml to about 70 mg/ml, about 35 mg/ml to about 40 mg/ml, about 35 mg/ml to about 45 mg/ml, about 35 mg/ml to about 50 mg/ml, about 35 mg/ml to about 55 mg/ml, about 35 mg/ml to about 60 mg/ml, about 35 mg/ml to about 65 mg/ml, about 35 mg/ml to about 70 mg/ml, about 40 mg/ml to about 45 mg/ml, about 40 mg/ml to about 50 mg/ml, about 40 mg/ml to about 55 mg/ml, about 40 mg/ml to about 60 mg/ml, about 40 mg/ml to about 65 mg/ml, about 40 mg/ml to about 70 mg/ml, about 45 mg/ml to about 50 mg/ml, about 45 mg/ml to about 55 mg/ml, about 45 mg/ml to about 60 mg/ml, about 45 mg/ml to about 65 mg/ml, about 45 mg/ml to about 70 mg/ml, about 50 mg/ml to about 55 mg/ml, about 50 mg/ml to about 60 mg/ml, about 50 mg/ml to about 65 mg/ml, about 50 mg/ml to about 70 mg/ml, about 55 mg/ml to about 60 mg/ml, about 55 mg/ml to about 65 mg/ml, about 55 mg/ml to about 70 mg/ml, about 60 mg/ml to about 65 mg/ml, about 60 mg/ml to about 70 mg/ml, or about 65 mg/ml to about 70 mg/ml. In some embodiments, the pharmaceutical compositions comprise naloxone between about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, or about 70 mg/ml. In some embodiments, the pharmaceutical compositions comprise naloxone between at least about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, or about 65 mg/ml. In some embodiments, the pharmaceutical compositions comprise naloxone between at most about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, or about 70 mg/ml.

In some embodiments, the pharmaceutical compositions comprise naloxone between at least about 20 mg/ml to about 70 mg/ml. In some embodiments, the pharmaceutical compositions comprise naloxone between at least about 20 mg/ml to about 25 mg/ml, about 20 mg/ml to about 30 mg/ml, about 20 mg/ml to about 35 mg/ml, about 20 mg/ml to about 40 mg/ml, about 20 mg/ml to about 45 mg/ml, about 20 mg/ml to about 50 mg/ml, about 20 mg/ml to about 55 mg/ml, about 20 mg/ml to about 60 mg/ml, about 20 mg/ml to about 65 mg/ml, about 20 mg/ml to about 70 mg/ml, about 25 mg/ml to about 30 mg/ml, about 25 mg/ml to about 35 mg/ml, about 25 mg/ml to about 40 mg/ml, about 25 mg/ml to about 45 mg/ml, about 25 mg/ml to about 50 mg/ml, about 25 mg/ml to about 55 mg/ml, about 25 mg/ml to about 60 mg/ml, about 25 mg/ml to about 65 mg/ml, about 25 mg/ml to about 70 mg/ml, about 30 mg/ml to about 35 mg/ml, about 30 mg/ml to about 40 mg/ml, about 30 mg/ml to about 45 mg/ml, about 30 mg/ml to about 50 mg/ml, about 30 mg/ml to about 55 mg/ml, about 30 mg/ml to about 60 mg/ml, about 30 mg/ml to about 65 mg/ml, about 30 mg/ml to about 70 mg/ml, about 35 mg/ml to about 40 mg/ml, about 35 mg/ml to about 45 mg/ml, about 35 mg/ml to about 50 mg/ml, about 35 mg/ml to about 55 mg/ml, about 35 mg/ml to about 60 mg/ml, about 35 mg/ml to about 65 mg/ml, about 35 mg/ml to about 70 mg/ml, about 40 mg/ml to about 45 mg/ml, about 40 mg/ml to about 50 mg/ml, about 40 mg/ml to about 55 mg/ml, about 40 mg/ml to about 60 mg/ml, about 40 mg/ml to about 65 mg/ml, about 40 mg/ml to about 70 mg/ml, about 45 mg/ml to about 50 mg/ml, about 45 mg/ml to about 55 mg/ml, about 45 mg/ml to about 60 mg/ml, about 45 mg/ml to about 65 mg/ml, about 45 mg/ml to about 70 mg/ml, about 50 mg/ml to about 55 mg/ml, about 50 mg/ml to about 60 mg/ml, about 50 mg/ml to about 65 mg/ml, about 50 mg/ml to about 70 mg/ml, about 55 mg/ml to about 60 mg/ml, about 55 mg/ml to about 65 mg/ml, about 55 mg/ml to about 70 mg/ml, about 60 mg/ml to about 65 mg/ml, about 60 mg/ml to about 70 mg/ml, or about 65 mg/ml to about 70 mg/ml. In some embodiments, the pharmaceutical compositions comprise naloxone between at least about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, or about 70 mg/ml. In some embodiments, the pharmaceutical compositions comprise naloxone between at least at least about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, or about 65 mg/ml. In some embodiments, the pharmaceutical compositions comprise naloxone between at least at most about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, or about 70 mg/ml.

In some embodiments, the pharmaceutical compositions comprise naloxone between at most about 20 mg/ml to about 70 mg/ml. In some embodiments, the pharmaceutical compositions comprise naloxone between at most about 20 mg/ml to about 25 mg/ml, about 20 mg/ml to about 30 mg/ml, about 20 mg/ml to about 35 mg/ml, about 20 mg/ml to about 40 mg/ml, about 20 mg/ml to about 45 mg/ml, about 20 mg/ml to about 50 mg/ml, about 20 mg/ml to about 55 mg/ml, about 20 mg/ml to about 60 mg/ml, about 20 mg/ml to about 65 mg/ml, about 20 mg/ml to about 70 mg/ml, about 25 mg/ml to about 30 mg/ml, about 25 mg/ml to about 35 mg/ml, about 25 mg/ml to about 40 mg/ml, about 25 mg/ml to about 45 mg/ml, about 25 mg/ml to about 50 mg/ml, about 25 mg/ml to about 55 mg/ml, about 25 mg/ml to about 60 mg/ml, about 25 mg/ml to about 65 mg/ml, about 25 mg/ml to about 70 mg/ml, about 30 mg/ml to about 35 mg/ml, about 30 mg/ml to about 40 mg/ml, about 30 mg/ml to about 45 mg/ml, about 30 mg/ml to about 50 mg/ml, about 30 mg/ml to about 55 mg/ml, about 30 mg/ml to about 60 mg/ml, about 30 mg/ml to about 65 mg/ml, about 30 mg/ml to about 70 mg/ml, about 35 mg/ml to about 40 mg/ml, about 35 mg/ml to about 45 mg/ml, about 35 mg/ml to about 50 mg/ml, about 35 mg/ml to about 55 mg/ml, about 35 mg/ml to about 60 mg/ml, about 35 mg/ml to about 65 mg/ml, about 35 mg/ml to about 70 mg/ml, about 40 mg/ml to about 45 mg/ml, about 40 mg/ml to about 50 mg/ml, about 40 mg/ml to about 55 mg/ml, about 40 mg/ml to about 60 mg/ml, about 40 mg/ml to about 65 mg/ml, about 40 mg/ml to about 70 mg/ml, about 45 mg/ml to about 50 mg/ml, about 45 mg/ml to about 55 mg/ml, about 45 mg/ml to about 60 mg/ml, about 45 mg/ml to about 65 mg/ml, about 45 mg/ml to about 70 mg/ml, about 50 mg/ml to about 55 mg/ml, about 50 mg/ml to about 60 mg/ml, about 50 mg/ml to about 65 mg/ml, about 50 mg/ml to about 70 mg/ml, about 55 mg/ml to about 60 mg/ml, about 55 mg/ml to about 65 mg/ml, about 55 mg/ml to about 70 mg/ml, about 60 mg/ml to about 65 mg/ml, about 60 mg/ml to about 70 mg/ml, or about 65 mg/ml to about 70 mg/ml. In some embodiments, the pharmaceutical compositions comprise naloxone between at most about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, or about 70 mg/ml. In some embodiments, the pharmaceutical compositions comprise naloxone between at most at least about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, or about 65 mg/ml. In some embodiments, the pharmaceutical compositions comprise naloxone between at most at most about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, or about 70 mg/ml.

In some embodiments, the pharmaceutical compositions comprise naloxone HCl between about 20 mg/ml to about 100 mg/ml. In some embodiments, the pharmaceutical compositions comprise naloxone HCl between about 20 mg/ml to about 30 mg/ml, about 20 mg/ml to about 35 mg/ml, about 20 mg/ml to about 40 mg/ml, about 20 mg/ml to about 45 mg/ml, about 20 mg/ml to about 50 mg/ml, about 20 mg/ml to about 55 mg/ml, about 20 mg/ml to about 60 mg/ml, about 20 mg/ml to about 70 mg/ml, about 20 mg/ml to about 80 mg/ml, about 20 mg/ml to about 90 mg/ml, about 20 mg/ml to about 100 mg/ml, about 30 mg/ml to about 35 mg/ml, about 30 mg/ml to about 40 mg/ml, about 30 mg/ml to about 45 mg/ml, about 30 mg/ml to about 50 mg/ml, about 30 mg/ml to about 55 mg/ml, about 30 mg/ml to about 60 mg/ml, about 30 mg/ml to about 70 mg/ml, about 30 mg/ml to about 80 mg/ml, about 30 mg/ml to about 90 mg/ml, about 30 mg/ml to about 100 mg/ml, about 35 mg/ml to about 40 mg/ml, about 35 mg/ml to about 45 mg/ml, about 35 mg/ml to about 50 mg/ml, about 35 mg/ml to about 55 mg/ml, about 35 mg/ml to about 60 mg/ml, about 35 mg/ml to about 70 mg/ml, about 35 mg/ml to about 80 mg/ml, about 35 mg/ml to about 90 mg/ml, about 35 mg/ml to about 100 mg/ml, about 40 mg/ml to about 45 mg/ml, about 40 mg/ml to about 50 mg/ml, about 40 mg/ml to about 55 mg/ml, about 40 mg/ml to about 60 mg/ml, about 40 mg/ml to about 70 mg/ml, about 40 mg/ml to about 80 mg/ml, about 40 mg/ml to about 90 mg/ml, about 40 mg/ml to about 100 mg/ml, about 45 mg/ml to about 50 mg/ml, about 45 mg/ml to about 55 mg/ml, about 45 mg/ml to about 60 mg/ml, about 45 mg/ml to about 70 mg/ml, about 45 mg/ml to about 80 mg/ml, about 45 mg/ml to about 90 mg/ml, about 45 mg/ml to about 100 mg/ml, about 50 mg/ml to about 55 mg/ml, about 50 mg/ml to about 60 mg/ml, about 50 mg/ml to about 70 mg/ml, about 50 mg/ml to about 80 mg/ml, about 50 mg/ml to about 90 mg/ml, about 50 mg/ml to about 100 mg/ml, about 55 mg/ml to about 60 mg/ml, about 55 mg/ml to about 70 mg/ml, about 55 mg/ml to about 80 mg/ml, about 55 mg/ml to about 90 mg/ml, about 55 mg/ml to about 100 mg/ml, about 60 mg/ml to about 70 mg/ml, about 60 mg/ml to about 80 mg/ml, about 60 mg/ml to about 90 mg/ml, about 60 mg/ml to about 100 mg/ml, about 70 mg/ml to about 80 mg/ml, about 70 mg/ml to about 90 mg/ml, about 70 mg/ml to about 100 mg/ml, about 80 mg/ml to about 90 mg/ml, about 80 mg/ml to about 100 mg/ml, or about 90 mg/ml to about 100 mg/ml. In some embodiments, the pharmaceutical compositions comprise naloxone HCl between about 20 mg/ml, about 30 mg/ml, about 35 mg/ml, about 40 mg/ml, about 45 mg/ml, about 50 mg/ml, about 55 mg/ml, about 60 mg/ml, about 70 mg/ml, about 80 mg/ml, about 90 mg/ml, or about 100 mg/ml. In some embodiments, the pharmaceutical compositions comprise naloxone HCl between at least about 20 mg/ml, about 30 mg/ml, about 35 mg/ml, about 40 mg/ml, about 45 mg/ml, about 50 mg/ml, about 55 mg/ml, about 60 mg/ml, about 70 mg/ml, about 80 mg/ml, or about 90 mg/ml. In some embodiments, the pharmaceutical compositions comprise naloxone HCl between at most about 30 mg/ml, about 35 mg/ml, about 40 mg/ml, about 45 mg/ml, about 50 mg/ml, about 55 mg/ml, about 60 mg/ml, about 70 mg/ml, about 80 mg/ml, about 90 mg/ml, or about 100 mg/ml.

In some embodiments, the pharmaceutical compositions comprise naloxone HCl at least about 20 mg/ml to about 100 mg/ml. In some embodiments, the pharmaceutical compositions comprise naloxone HCl at least about 20 mg/ml to about 30 mg/ml, about 20 mg/ml to about 35 mg/ml, about 20 mg/ml to about 40 mg/ml, about 20 mg/ml to about 45 mg/ml, about 20 mg/ml to about 50 mg/ml, about 20 mg/ml to about 55 mg/ml, about 20 mg/ml to about 60 mg/ml, about 20 mg/ml to about 70 mg/ml, about 20 mg/ml to about 80 mg/ml, about 20 mg/ml to about 90 mg/ml, about 20 mg/ml to about 100 mg/ml, about 30 mg/ml to about 35 mg/ml, about 30 mg/ml to about 40 mg/ml, about 30 mg/ml to about 45 mg/ml, about 30 mg/ml to about 50 mg/ml, about 30 mg/ml to about 55 mg/ml, about 30 mg/ml to about 60 mg/ml, about 30 mg/ml to about 70 mg/ml, about 30 mg/ml to about 80 mg/ml, about 30 mg/ml to about 90 mg/ml, about 30 mg/ml to about 100 mg/ml, about 35 mg/ml to about 40 mg/ml, about 35 mg/ml to about 45 mg/ml, about 35 mg/ml to about 50 mg/ml, about 35 mg/ml to about 55 mg/ml, about 35 mg/ml to about 60 mg/ml, about 35 mg/ml to about 70 mg/ml, about 35 mg/ml to about 80 mg/ml, about 35 mg/ml to about 90 mg/ml, about 35 mg/ml to about 100 mg/ml, about 40 mg/ml to about 45 mg/ml, about 40 mg/ml to about 50 mg/ml, about 40 mg/ml to about 55 mg/ml, about 40 mg/ml to about 60 mg/ml, about 40 mg/ml to about 70 mg/ml, about 40 mg/ml to about 80 mg/ml, about 40 mg/ml to about 90 mg/ml, about 40 mg/ml to about 100 mg/ml, about 45 mg/ml to about 50 mg/ml, about 45 mg/ml to about 55 mg/ml, about 45 mg/ml to about 60 mg/ml, about 45 mg/ml to about 70 mg/ml, about 45 mg/ml to about 80 mg/ml, about 45 mg/ml to about 90 mg/ml, about 45 mg/ml to about 100 mg/ml, about 50 mg/ml to about 55 mg/ml, about 50 mg/ml to about 60 mg/ml, about 50 mg/ml to about 70 mg/ml, about 50 mg/ml to about 80 mg/ml, about 50 mg/ml to about 90 mg/ml, about 50 mg/ml to about 100 mg/ml, about 55 mg/ml to about 60 mg/ml, about 55 mg/ml to about 70 mg/ml, about 55 mg/ml to about 80 mg/ml, about 55 mg/ml to about 90 mg/ml, about 55 mg/ml to about 100 mg/ml, about 60 mg/ml to about 70 mg/ml, about 60 mg/ml to about 80 mg/ml, about 60 mg/ml to about 90 mg/ml, about 60 mg/ml to about 100 mg/ml, about 70 mg/ml to about 80 mg/ml, about 70 mg/ml to about 90 mg/ml, about 70 mg/ml to about 100 mg/ml, about 80 mg/ml to about 90 mg/ml, about 80 mg/ml to about 100 mg/ml, or about 90 mg/ml to about 100 mg/ml. In some embodiments, the pharmaceutical compositions comprise naloxone HCl at least about 20 mg/ml, about 30 mg/ml, about 35 mg/ml, about 40 mg/ml, about 45 mg/ml, about 50 mg/ml, about 55 mg/ml, about 60 mg/ml, about 70 mg/ml, about 80 mg/ml, about 90 mg/ml, or about 100 mg/ml. In some embodiments, the pharmaceutical compositions comprise naloxone HCl at least at least about 20 mg/ml, about 30 mg/ml, about 35 mg/ml, about 40 mg/ml, about 45 mg/ml, about 50 mg/ml, about 55 mg/ml, about 60 mg/ml, about 70 mg/ml, about 80 mg/ml, or about 90 mg/ml. In some embodiments, the pharmaceutical compositions comprise naloxone HCl at least at most about 30 mg/ml, about 35 mg/ml, about 40 mg/ml, about 45 mg/ml, about 50 mg/ml, about 55 mg/ml, about 60 mg/ml, about 70 mg/ml, about 80 mg/ml, about 90 mg/ml, or about 100 mg/ml.

In some embodiments, the pharmaceutical compositions comprise naloxone HCl at most about 20 mg/ml to about 100 mg/ml. In some embodiments, the pharmaceutical compositions comprise naloxone HCl at most about 20 mg/ml to about 30 mg/ml, about 20 mg/ml to about 35 mg/ml, about 20 mg/ml to about 40 mg/ml, about 20 mg/ml to about 45 mg/ml, about 20 mg/ml to about 50 mg/ml, about 20 mg/ml to about 55 mg/ml, about 20 mg/ml to about 60 mg/ml, about 20 mg/ml to about 70 mg/ml, about 20 mg/ml to about 80 mg/ml, about 20 mg/ml to about 90 mg/ml, about 20 mg/ml to about 100 mg/ml, about 30 mg/ml to about 35 mg/ml, about 30 mg/ml to about 40 mg/ml, about 30 mg/ml to about 45 mg/ml, about 30 mg/ml to about 50 mg/ml, about 30 mg/ml to about 55 mg/ml, about 30 mg/ml to about 60 mg/ml, about 30 mg/ml to about 70 mg/ml, about 30 mg/ml to about 80 mg/ml, about 30 mg/ml to about 90 mg/ml, about 30 mg/ml to about 100 mg/ml, about 35 mg/ml to about 40 mg/ml, about 35 mg/ml to about 45 mg/ml, about 35 mg/ml to about 50 mg/ml, about 35 mg/ml to about 55 mg/ml, about 35 mg/ml to about 60 mg/ml, about 35 mg/ml to about 70 mg/ml, about 35 mg/ml to about 80 mg/ml, about 35 mg/ml to about 90 mg/ml, about 35 mg/ml to about 100 mg/ml, about 40 mg/ml to about 45 mg/ml, about 40 mg/ml to about 50 mg/ml, about 40 mg/ml to about 55 mg/ml, about 40 mg/ml to about 60 mg/ml, about 40 mg/ml to about 70 mg/ml, about 40 mg/ml to about 80 mg/ml, about 40 mg/ml to about 90 mg/ml, about 40 mg/ml to about 100 mg/ml, about 45 mg/ml to about 50 mg/ml, about 45 mg/ml to about 55 mg/ml, about 45 mg/ml to about 60 mg/ml, about 45 mg/ml to about 70 mg/ml, about 45 mg/ml to about 80 mg/ml, about 45 mg/ml to about 90 mg/ml, about 45 mg/ml to about 100 mg/ml, about 50 mg/ml to about 55 mg/ml, about 50 mg/ml to about 60 mg/ml, about 50 mg/ml to about 70 mg/ml, about 50 mg/ml to about 80 mg/ml, about 50 mg/ml to about 90 mg/ml, about 50 mg/ml to about 100 mg/ml, about 55 mg/ml to about 60 mg/ml, about 55 mg/ml to about 70 mg/ml, about 55 mg/ml to about 80 mg/ml, about 55 mg/ml to about 90 mg/ml, about 55 mg/ml to about 100 mg/ml, about 60 mg/ml to about 70 mg/ml, about 60 mg/ml to about 80 mg/ml, about 60 mg/ml to about 90 mg/ml, about 60 mg/ml to about 100 mg/ml, about 70 mg/ml to about 80 mg/ml, about 70 mg/ml to about 90 mg/ml, about 70 mg/ml to about 100 mg/ml, about 80 mg/ml to about 90 mg/ml, about 80 mg/ml to about 100 mg/ml, or about 90 mg/ml to about 100 mg/ml. In some embodiments, the pharmaceutical compositions comprise naloxone HCl at most about 20 mg/ml, about 30 mg/ml, about 35 mg/ml, about 40 mg/ml, about 45 mg/ml, about 50 mg/ml, about 55 mg/ml, about 60 mg/ml, about 70 mg/ml, about 80 mg/ml, about 90 mg/ml, or about 100 mg/ml. In some embodiments, the pharmaceutical compositions comprise naloxone HCl at most at least about 20 mg/ml, about 30 mg/ml, about 35 mg/ml, about 40 mg/ml, about 45 mg/ml, about 50 mg/ml, about 55 mg/ml, about 60 mg/ml, about 70 mg/ml, about 80 mg/ml, or about 90 mg/ml. In some embodiments, the pharmaceutical compositions comprise naloxone HCl at most at most about 30 mg/ml, about 35 mg/ml, about 40 mg/ml, about 45 mg/ml, about 50 mg/ml, about 55 mg/ml, about 60 mg/ml, about 70 mg/ml, about 80 mg/ml, about 90 mg/ml, or about 100 mg/ml.

In some cases, it is desirable to include tonicity agents such as sodium chloride, sodium nitrate, sodium sulfate, sodium bisulfate, potassium chloride, calcium chloride, magnesium chloride, zinc chloride, potassium acetate, sodium acetate, sodium bicarbonate, sodium carbonate, sodium thiosulfate, magnesium sulfate, disodium hydrogen phosphate, sodium dihydrogen phosphate, potassium dihydrogen phosphate, dextrose, mannitol, sorbitol, dextrose, sucrose, urea, propylene glycol, glycerin, or a combination thereof. In some embodiments, the tonicity agents can be present in the pharmaceutical compositions at concentrations between about 0.0001 wt. % to about 10 wt %. In some embodiments, the tonicity agents can be present in the pharmaceutical compositions at concentrations between about 0.0001 wt % to about 0.0005 wt %, about 0.0001 wt % to about 0.001 wt %, about 0.0001 wt % to about 0.005 wt %, about 0.0001 wt % to about 0.01 wt %, about 0.0001 wt % to about 0.05 wt %, about 0.0001 wt % to about 0.1 wt %, about 0.0001 wt % to about 0.5 wt %, about 0.0001 wt % to about 1 wt %, about 0.0001 wt % to about 5 wt %, about 0.0001 wt % to about 10 wt %, about 0.0005 wt % to about 0.001 wt %, about 0.0005 wt % to about 0.005 wt %, about 0.0005 wt % to about 0.01 wt %, about 0.0005 wt % to about 0.05 wt %, about 0.0005 wt % to about 0.1 wt %, about 0.0005 wt % to about 0.5 wt %, about 0.0005 wt % to about 1 wt %, about 0.0005 wt % to about 5 wt %, about 0.0005 wt % to about 10 wt %, about 0.001 wt % to about 0.005 wt %, about 0.001 wt % to about 0.01 wt %, about 0.001 wt % to about 0.05 wt %, about 0.001 wt % to about 0.1 wt %, about 0.001 wt % to about 0.5 wt %, about 0.001 wt % to about 1 wt %, about 0.001 wt % to about 5 wt %, about 0.001 wt % to about 10 wt %, about 0.005 wt % to about 0.01 wt %, about 0.005 wt % to about 0.05 wt %, about 0.005 wt % to about 0.1 wt %, about 0.005 wt % to about 0.5 wt %, about 0.005 wt % to about 1 wt %, about 0.005 wt % to about 5 wt %, about 0.005 wt % to about 10 wt %, about 0.01 wt % to about 0.05 wt %, about 0.01 wt % to about 0.1 wt %, about 0.01 wt % to about 0.5 wt %, about 0.01 wt % to about 1 wt %, about 0.01 wt % to about 5 wt %, about 0.01 wt % to about 10 wt %, about 0.05 wt % to about 0.1 wt %, about 0.05 wt % to about 0.5 wt %, about 0.05 wt % to about 1 wt %, about 0.05 wt % to about 5 wt %, about 0.05 wt % to about 10 wt %, about 0.1 wt % to about 0.5 wt %, about 0.1 wt % to about 1 wt %, about 0.1 wt % to about 5 wt %, about 0.1 wt % to about 10 wt %, about 0.5 wt % to about 1 wt %, about 0.5 wt % to about 5 wt %, about 0.5 wt % to about 10 wt %, about 1 wt % to about 5 wt %, about 1 wt % to about 10 wt %, or about 5 wt % to about 10 wt %. In some embodiments, the tonicity agents can be present in the pharmaceutical compositions at concentrations between about 0.0001 wt %, about 0.0005 wt %, about 0.001 wt %, about 0.005 wt %, about 0.01 wt %, about 0.05 wt %, about 0.1 wt %, about 0.5 wt %, about 1 wt %, about 5 wt %, or about 10 wt %. In some embodiments, the tonicity agents can be present in the pharmaceutical compositions at concentrations between at least about 0.0001 wt %, about 0.0005 wt %, about 0.001 wt %, about 0.005 wt %, about 0.01 wt %, about 0.05 wt %, about 0.1 wt %, about 0.5 wt %, about 1 wt %, or about 5 wt %. In some embodiments, the tonicity agents can be present in the pharmaceutical compositions at concentrations between at most about 0.0005 wt %, about 0.001 wt %, about 0.005 wt %, about 0.01 wt %, about 0.05 wt %, about 0.1 wt %, about 0.5 wt %, about 1 wt %, about 5 wt %, or about 10 wt %.

In some embodiments, the pharmaceutical compositions comprise at least one surfactant or a buffering agent. In other embodiments, the surfactants or buffering agents can be combined with one or more of the pharmaceutically acceptable vehicles previously described herein so that the surfactant and/or buffering agent maintains the product at an optimal pH for stability. Suitable surfactants include, but are not limited to: a) natural and synthetic lipophilic agents, e.g., phospholipids, cholesterol, and cholesterol fatty acid esters and derivatives thereof; b) nonionic surfactants, which include for example, polyoxyethylene fatty alcohol esters, sorbitan fatty acid esters (Spans), polyoxyethylene sorbitan fatty acid esters (e.g., polyoxyethylene (20) sorbitan monooleate (Tween 80), polyoxyethylene (20) sorbitan monostearate (Tween 60), polyoxyethylene (20) sorbitan monolaurate (Tween 20) and other Tweens, sorbitan esters, glycerol esters, e.g., Myrj and glycerol triacetate (triacetin), polyethylene glycols, cetyl alcohol, cetostearyl alcohol, stearyl alcohol, polysorbate 80, poloxamers, poloxamines, polyoxyethylene castor oil derivatives (e.g., Cremophor® RH40, Cremphor A25, Cremphor A20, Cremophor® EL) and other Cremophors, sulfosuccinates, alkyl sulphates (SLS); PEG glyceryl fatty acid esters such as PEG-8 glyceryl caprylate/caprate (Labrasol), PEG-4 glyceryl caprylate/caprate (Labrafac Hydro WL 1219), PEG-32 glyceryl laurate (Gelucire 444/14), PEG-6 glyceryl mono oleate (Labrafil M 1944 CS), PEG-6 glyceryl linoleate (Labrafil M 2125 CS); propylene glycol mono- and di-fatty acid esters, such as propylene glycol laurate, propylene glycol caprylate/caprate; Brij® 700, ascorbyl-6-palmitate, stearylamine, sodium lauryl sulfate, polyoxethyleneglycerol triiricinoleate, and any combinations or mixtures thereof; c) anionic surfactants include, but are not limited to, calcium carboxymethylcellulose, sodium carboxymethylcellulose, sodium sulfosuccinate, dioctyl, sodium alginate, alkyl polyoxyethylene sulfates, sodium lauryl sulfate, triethanolamine stearate, potassium laurate, bile salts, and any combinations or mixtures thereof; and d) cationic surfactants such as cetyltrimethylammonium bromide, and lauryldimethylbenzylammonium chloride.

In some embodiments, the surfactants or buffering agents can be present in the pharmaceutical compositions at concentrations between about 0.0001 wt % to about 10 wt %. In some embodiments, the surfactants or buffering agents can be present in the pharmaceutical compositions at concentrations between about 0.0001 wt % to about 0.0005 wt %, about 0.0001 wt % to about 0.001 wt %, about 0.0001 wt % to about 0.005 wt %, about 0.0001 wt % to about 0.01 wt %, about 0.0001 wt % to about 0.05 wt %, about 0.0001 wt % to about 0.1 wt %, about 0.0001 wt % to about 5 wt %, about 0.0001 wt % to about 1 wt %, about 0.0001 wt % to about 5 wt %, about 0.0001 wt % to about 10 wt %, about 0.0005 wt % to about 0.001 wt %, about 0.0005 wt % to about 0.005 wt %, about 0.0005 wt % to about 0.01 wt %, about 0.0005 wt % to about 0.05 wt %, about 0.0005 wt % to about 0.1 wt %, about 0.0005 wt % to about 0.5 wt %, about 0.0005 wt % to about 1 wt %, about 0.0005 wt % to about 5 wt %, about 0.0005 wt % to about 10 wt %, about 0.001 wt % to about 0.005 wt %, about 0.001 wt % to about 0.01 wt %, about 0.001 wt % to about 0.05 wt %, about 0.001 wt % to about 0.1 wt %, about 0.001 wt % to about 5 wt %, about 0.001 wt % to about 1 wt %, about 0.001 wt % to about 5 wt %, about 0.001 wt % to about 10 wt %, about 0.005 wt % to about 0.01 wt %, about 0.005 wt % to about 0.05 wt %, about 0.005 wt % to about 0.1 wt %, about 0.005 wt % to about 5 wt %, about 0.005 wt % to about 1 wt %, about 0.005 wt % to about 5 wt %, about 0.005 wt % to about 10 wt %, about 0.01 wt % to about 0.05 wt %, about 0.01 wt % to about 0.1 wt %, about 0.01 wt % to about 5 wt %, about 0.01 wt % to about 1 wt %, about 0.01 wt % to about 5 wt %, about 0.01 wt % to about 10 wt %, about 0.05 wt % to about 0.1 wt %, about 0.05 wt % to about 5 wt %, about 0.05 wt % to about 1 wt %, about 0.05 wt % to about 5 wt %, about 0.05 wt % to about 10 wt %, about 0.1 wt % to about 5 wt %, about 0.1 wt % to about 1 wt %, about 0.1 wt % to about 5 wt %, about 0.1 wt % to about 10 wt %, about 5 wt % to about 1 wt %, about 5 wt % to about 5 wt %, about 5 wt % to about 10 wt %, about 1 wt % to about 5 wt %, about 1 wt % to about 10 wt %, or about 5 wt % to about 10 wt %. In some embodiments, the surfactants or buffering agents can be present in the pharmaceutical compositions at concentrations between about 0.0001 wt %, about 0.0005 wt %, about 0.001 wt %, about 0.005 wt %, about 0.01 wt %, about 0.05 wt %, about 0.1 wt %, about 5 wt %, about 1 wt %, about 5 wt %, or about 10 wt %. In some embodiments, the surfactants or buffering agents can be present in the pharmaceutical compositions at concentrations between at least about 0.0001 wt %, about 0.0005 wt %, about 0.001 wt %, about 0.005 wt %, about 0.01 wt %, about 0.05 wt %, about 0.1 wt %, about 5 wt %, about 1 wt %, or about 5 wt %. In some embodiments, the surfactants or buffering agents can be present in the pharmaceutical compositions at concentrations between at most about 0.0005 wt %, about 0.001 wt %, about 0.005 wt %, about 0.01 wt %, about 0.05 wt %, about 0.1 wt %, about 5 wt %, about 1 wt %, about 5 wt %, or about 10 wt %.

In some embodiments, the pH of the pharmaceutical compositions described herein comprises a range about 1.5 to about 6.9. In some embodiments, the pH of the pharmaceutical compositions described herein comprises a range about 1.5 to about 2, about 1.5 to about 2.5, about 1.5 to about 3, about 1.5 to about 3.5, about 1.5 to about 4, about 1.5 to about 4.5, about 1.5 to about 5, about 1.5 to about 5.5, about 1.5 to about 6, about 1.5 to about 6.5, about 1.5 to about 6.9, about 2 to about 2.5, about 2 to about 3, about 2 to about 3.5, about 2 to about 4, about 2 to about 4.5, about 2 to about 5, about 2 to about 5.5, about 2 to about 6, about 2 to about 6.5, about 2 to about 6.9, about 2.5 to about 3, about 2.5 to about 3.5, about 2.5 to about 4, about 2.5 to about 4.5, about 2.5 to about 5, about 2.5 to about 5.5, about 2.5 to about 6, about 2.5 to about 6.5, about 2.5 to about 6.9, about 3 to about 3.5, about 3 to about 4, about 3 to about 4.5, about 3 to about 5, about 3 to about 5.5, about 3 to about 6, about 3 to about 6.5, about 3 to about 6.9, about 3.5 to about 4, about 3.5 to about 4.5, about 3.5 to about 5, about 3.5 to about 5.5, about 3.5 to about 6, about 3.5 to about 6.5, about 3.5 to about 6.9, about 4 to about 4.5, about 4 to about 5, about 4 to about 5.5, about 4 to about 6, about 4 to about 6.5, about 4 to about 6.9, about 4.5 to about 5, about 4.5 to about 5.5, about 4.5 to about 6, about 4.5 to about 6.5, about 4.5 to about 6.9, about 5 to about 5.5, about 5 to about 6, about 5 to about 6.5, about 5 to about 6.9, about 5.5 to about 6, about 5.5 to about 6.5, about 5.5 to about 6.9, about 6 to about 6.5, about 6 to about 6.9, or about 6.5 to about 6.9. In some embodiments, the pH of the pharmaceutical compositions described herein comprises a range about 1.5, about 2, about 2.5, about 3, about 3.5, about 4, about 4.5, about 5, about 5.5, about 6, about 6.5, or about 6.9. In some embodiments, the pH of the pharmaceutical compositions described herein comprises a range at least about 1.5, about 2, about 2.5, about 3, about 3.5, about 4, about 4.5, about 5, about 5.5, about 6, or about 6.5. In some embodiments, the pH of the pharmaceutical compositions described herein comprises a range at most about 2, about 2.5, about 3, about 3.5, about 4, about 4.5, about 5, about 5.5, about 6, about 6.5, or about 6.9.

In some embodiments, the pharmaceutical formulations include one or more pH adjusting agents or buffering agents. Suitable pH adjusting agents or buffers include, but are not limited to acetate, bicarbonate, ammonium chloride, citrate, phosphate, deuterated forms of acetate, bicarbonate, ammonium chloride, citrate, phosphate, pharmaceutically acceptable salts thereof and combinations or mixtures thereof.

In one embodiment, when one or more buffers are utilized in the formulations of the present disclosure, they are combined, e.g., with a pharmaceutically acceptable vehicle and are present in the final formulation, e.g., in an amount ranging from about 0.1% to about 20%, from about 0.5% to about 10%. In certain embodiments of the present disclosure, the amount of buffer included in the aqueous or gel formulations are an amount such that the pH of the gel formulation does not interfere with the body's natural buffering system.

Described herein, in some instances, are pharmaceutical compositions comprising at least one chelator or chelating agent. In some embodiments, the chelators can be a bicarboxylic acid, a tricarboxylic acid, or an aminopolycarboxylic acid. In some instances, the chelators can be ethylenediaminetetraacetic acid (EDTA), ethylene glycol-bis((3-aminoethyl ether)-N,N,N',N'-tetraacetic acid (EGTA), and penta(carboxymethyl)diethylenetriamine (DTPA), or salts and hydrates thereof. In some instances, the chelating agents include monomeric polyacids such as EDTA, cyclohexanediamine tetraacetic acid (CDTA), hydroxyethylethylenediamine triacetic acid (HEDTA), diethylenetriamine pentaacetic acid (DTPA), dimercaptopropane sulfonic acid (DMPS), dimercaptosuccmic acid (DMSA), aminotrimethylene phosphonic acid (ATPA), citric acid, acceptable salts thereof, and combinations thereof. In some instances, the chelating agents include pyrophosphates, tripolyphosphates, and, hexametaphosphates, chelating antibiotics such as chloroquine and tetracycline, nitrogen-containing chelating agent containing two or more chelating nitrogen atoms within an imino group or in an aromatic ring (e.g., diimines, 2,2'-bipyridines, etc.), and various polyamines such as cyclam (1,4,7,11-tetraazacyclotetradecane), $N(C_1$-$C_{30}$ alkyl)-substituted cyclams (e.g., hexadecyclam, tetramethylhexadecylcyclam), diethylenetriamine (DETA), spermine, diethylnorspermine (DENSPM), diethylhomo-spermine (DEHOP), and deferoxamine (N'-[5-[[4-[[5-(acetylhydroxyamino)pentyl]amino]-1,4-dioxobutyl]hydroxy-amino]pentyl]-N'-(5-aminopentyl)-N-hydroxybutanediamide; also known as desferrioxamine B and DFO).

The concentration of the chelating agents, in some embodiments, is between about 0.001% to about 0.20%, between about 0.004% to about 0.20%, between about 0.005% to about 0.20%, between about 0.010% to about 0.20%, between about 0.015% to about 0.20%, between about 0.020% to about 0.20%, between about 0.025% to about 0.20%, between about 0.030% to about 0.20%, between about 0.035% to about 0.20%, between about 0.040% to about 0.20%, or between about 0.045% to about 0.20% by weight of the composition. In some embodiments, the chelator is between about 0.01% to about 2.0%, between about 0.04% to about 2.0%, between about 0.05% to about 2.0%, between about 0.010% to about 2.0%, between about 0.015% to about 2.0%, between about 0.020% to about 2.0%, between about 0.025% to about 2.0%, between about 0.030% to about 2.0%, between about 0.035% to about 2.0%, between about 0.040% to about 2.0%, or between about 0.045% to about 2.0% by weight of the composition. In some instances, the chelator is present in the pharmaceutical compositions at a concentration of at least or about 0.001%, 0.002%, 0.003%, 0.004%, 0.005%, 0.006%, 0.007%, 0.008%, 0.009%, 0.010%, 0.020%, 0.030%, 0.040%, 0.050%, 0.060%, 0.070%, 0.080%, 0.090%, 0.10%, 0.20%, 0.30%, 0.40%, 0.50%, 0.60%, 0.70%, 0.80%, 0.90%, 1.0%, 2.0%, 3.0%, 4.0%, or more than 4.0% by weight of the composition. In some instances, the chelator is EDTA.

Described herein, in some embodiments, are pharmaceutical compositions comprising at least one stabilizer or stabilizing agent such as fatty acids, fatty alcohols, alcohols, long chain fatty acid esters, long chain ethers, hydrophilic derivatives of fatty acids, polyvinyl pyrrolidones, polyvinyl ethers, polyvinyl alcohols, hydrocarbons, hydrophobic polymers, moisture-absorbing polymers, and combinations thereof. In some embodiments, amide analogues of stabilizers can also be used. In further embodiments, the chosen stabilizers or stabilizing agents change the hydrophobicity of the formulation, improve the mixing of various components in the formulation, control the moisture level in the formula, or control the mobility of the phase. In other embodiments, stabilizers or stabilizing agents are present in sufficient amounts to inhibit the degradation of the pharmaceutical compositions. Examples of such stabilizing agents can include, but are not limited to: glycerol, methionine, monothioglycerol, EDTA, ascorbic acid, polysorbate 80, polysorbate 20, arginine, heparin, dextran sulfate, cyclodextrins, pentosan polysulfate and other heparinoids, divalent cations such as magnesium and zinc, or combinations thereof. In some embodiments, the stabilizer is EDTA.

Stabilizing agents, in some embodiments, are present in the composition at about 0.001%, 0.005%, 0.010%, 0.015%, 0.020%, 0.025%, 0.030%, 0.035%, 0.040%, 0.045%, 0.050%, 0.055%, 0.060%, 0.065%, 0.070%, 0.075%, 0.080%, 0.085%, 0.090%, 0.095%, 0.1%, 0.2%, 0.3%, 0.4%, 0.5%, 0.6%, 0.7%, 0.8%, 0.9%, 1.0%, 1.5%, 2.0%, 2.5% or 3.0%. In some embodiments, the stabilizing agent is present in the composition from about 0.001% to about 0.05%, from about 0.001% to about 0.04%, from about 0.001% to about 0.03%, from about 0.001% to about 0.025%, from about 0.001% to about 0.02%, from about 0.001% to about 0.01%, from about 0.001% to about 0.008%, or from about 0.001% to about 0.005%. In some cases, the percentage is a weight percentage.

In some embodiments, EDTA is present in the composition at about 0.001%, 0.005%, 0.010%, 0.015%, 0.020%, 0.025%, 0.030%, 0.035%, 0.040%, 0.045%, 0.050%, 0.055%, 0.060%, 0.065%, 0.070%, 0.075%, 0.080%, 0.085%, 0.090%, 0.095%, 0.1%, 0.2%, 0.3%, 0.4%, 0.5%, 0.6%, 0.7%, 0.8%, 0.9%, 1.0%, 1.5%, 2.0%, 2.5% or 3.0%. In some embodiments, EDTA is present in the composition from about 0.01% to about 0.05%, from about 0.01% to about 0.04%, from about 0.01% to about 0.03%, from about 0.01% to about 0.025%, from about 0.01% to about 0.02%, from about 0.001% to about 0.01%, from about 0.001% to about 0.008%, or from about 0.001% to about 0.005%. In some cases, the percentage is a weight percentage.

Other useful formulations optionally include one or more antioxidants to enhance chemical stability where required. Suitable antioxidants include, by way of example only, ascorbic acid, methionine, sodium thiosulfate, butylated hydroxytoluene, and sodium metabisulfite. In one embodiment, antioxidants are selected from metal chelating agents, thiol containing compounds and other general stabilizing agents.

In certain embodiments, pharmaceutical compositions provided herein include one or more preservatives to inhibit microbial growth or activity. Suitable preservatives include mercury-containing substances such as merfen and thiomersal; stabilized chlorine dioxide; and quaternary ammonium compounds such as benzalkonium chloride, cetrimonium, sodium perborate, stabilized oxychloro complex, SofZia, polyquaternium-1, chlorobutanol, edetate disodium, polyhexamethylene biguanide, or combinations thereof. In some embodiments, the preservatives can be present in the pharmaceutical compositions at concentrations between about In some embodiments, the preservatives can be present in the pharmaceutical compositions at concentrations between about 0.0001 wt % to about 10 wt %. In some embodiments, the preservatives can be present in the pharmaceutical compositions at concentrations between about 0.0001 wt % to about 0.0005 wt %, about 0.0001 wt % to about 0.001 wt %, about 0.0001 wt % to about 0.005 wt %, about 0.0001 wt % to about 0.01 wt %, about 0.0001 wt % to about 0.05 wt %, about 0.0001 wt % to about 0.1 wt %, about 0.0001 wt % to about 0.5 wt %, about 0.0001 wt % to about 1 wt %, about 0.0001 wt % to about 5 wt %, about 0.0001 wt % to about 10 wt %, about 0.0005 wt % to about 0.001 wt %, about 0.0005 wt % to about 0.005 wt %, about 0.0005 wt % to about 0.01 wt %, about 0.0005 wt % to about 0.05 wt %, about 0.0005 wt % to about 0.1 wt %, about 0.0005 wt % to about 0.5 wt %, about 0.0005 wt % to about 1 wt %, about 0.0005 wt % to about 5 wt %, about 0.0005 wt % to about 10 wt %, about 0.001 wt % to about 0.005 wt %, about 0.001 wt % to about 0.01 wt %, about 0.001 wt % to about 0.05 wt %, about 0.001 wt % to about 0.1 wt %, about 0.001 wt % to about 0.5 wt %, about 0.001 wt % to about 1 wt %, about 0.001 wt % to about 5 wt %, about 0.001 wt % to about 10 wt %, about 0.005 wt % to about 0.01 wt %, about 0.005 wt % to about 0.05 wt %, about 0.005 wt % to about 0.1 wt %, about 0.005 wt % to about 0.5 wt %, about 0.005 wt % to about 1 wt %, about 0.005 wt % to about 5 wt %, about 0.005 wt % to about 10 wt %, about 0.01 wt % to about 0.05 wt %, about 0.01 wt % to about 0.1 wt %, about 0.01 wt % to about 0.5 wt %, about 0.01 wt % to about 1 wt %, about 0.01 wt % to about 5 wt %, about 0.01 wt % to about 10 wt %, about 0.05 wt % to about 0.1 wt %, about 0.05 wt % to about 0.5 wt %, about 0.05 wt % to about 1 wt %, about 0.05 wt % to about 5 wt %, about 0.05 wt % to about 10 wt %, about 0.1 wt % to about 0.5 wt %, about 0.1 wt % to about 1 wt %, about 0.1 wt % to about 5 wt %, about 0.1 wt % to about 10 wt %, about 0.5 wt % to about 1 wt %, about 0.5 wt % to about 5 wt %, about 0.5 wt % to about 10 wt %, about 1 wt % to about 5 wt %, about 1 wt % to about 10 wt %, or about 5 wt % to about 10 wt %. In some embodiments, the preservatives can be present in the pharmaceutical compositions at concentrations between about 0.0001 wt %, about 0.0005 wt %, about 0.001 wt %, about 0.005 wt %, about 0.01 wt %, about 0.05 wt %, about 0.1 wt %, about 0.5 wt %, about 1 wt %, about 5 wt %, or about 10 wt %. In some embodiments, the preservatives can be present in the pharmaceutical compositions at concentrations between at least about 0.0001 wt %, about 0.0005 wt %, about 0.001 wt %, about 0.005 wt %, about 0.01 wt %, about 0.05 wt %, about 0.1 wt %, about 0.5 wt %, about 1 wt %, or about 5 wt %. In some embodiments, the preservatives can be present in the pharmaceutical compositions at concentrations between at most about 0.0005 wt %, about 0.001 wt %, about 0.005 wt %, about 0.01 wt %, about 0.05 wt %, about 0.1 wt %, about 0.5 wt %, about 1 wt %, about 5 wt %, or about 10 wt %.

In some embodiments, formulations described herein benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

The pharmaceutical compositions described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the pharmaceutical compositions described herein comprise an aqueous formulations, powder formulations, gel formulations, semi-solid formulations, solid formulations, or a combination thereof. In some embodiments, the pharmaceutical compositions described herein comprise a viscosity between about 0.001 centipoise to about 10,000,000 centipoise. In some embodiments, the pharmaceutical compositions described herein comprise a viscosity between about 0.001 centipoise to about 0.01 centipoise, about 0.001 centipoise to about 0.1 centipoise, about 0.001 centipoise to about 1 centipoise, about 0.001 centipoise to about 10 centipoise, about 0.001 centipoise to about 100 centipoise, about 0.001 centipoise to about 1,000 centipoise, about 0.001 centipoise to about 10,000 centipoise, about 0.001 centipoise to about 100,000 centipoise, about 0.001 centipoise to about 1,000,000 centipoise, about 0.001 centipoise to about 10,000,000 centipoise, about 0.01 centipoise to about 0.1 centipoise, about 0.01 centipoise to about 1 centipoise, about 0.01 centipoise to about 10 centipoise, about 0.01 centipoise to about 100 centipoise, about 0.01 centipoise to about 1,000 centipoise, about 0.01 centipoise to about 10,000 centipoise, about 0.01 centipoise to about 100,000 centipoise, about 0.01 centipoise to about 1,000,000 centipoise, about 0.01 centipoise to about 10,000,000 centipoise, about 0.1 centipoise to about 1 centipoise, about 0.1 centipoise to about 10 centipoise, about 0.1 centipoise to about 100 centipoise, about 0.1 centipoise to about 1,000 centipoise, about 0.1 centipoise to about 10,000 centipoise, about 0.1 centipoise to about 100,000 centipoise, about 0.1 centipoise to about 1,000,000 centipoise, about 0.1 centipoise to about 10,000,000 centipoise, about 1 centipoise to about 10 centipoise, about 1 centipoise to about 100 centipoise, about 1 centipoise to about 1,000 centipoise, about 1 centipoise to about 10,000 centipoise, about 1 centipoise to about 100,000 centipoise, about 1 centipoise to about 1,000,000 centipoise, about 1 centipoise to about 10,000,000 centipoise, about 10 centipoise to about 100 centipoise, about 10 centipoise to about 1,000 centipoise, about 10 centipoise to about 10,000 centipoise, about 10 centipoise to about 100,000 centipoise, about 10 centipoise to about 1,000,000 centipoise, about 10 centipoise to about 10,000,000 centipoise, about 100 centipoise to about 1,000 centipoise, about 100 centipoise to about 10,000 centipoise, about 100 centipoise to about 100,000 centipoise, about 100 centipoise to about 1,000,000 centipoise, about 100 centipoise to about 10,000,000 centipoise, about 1,000 centipoise to about 10,000 centipoise, about 1,000 centipoise to about 100,000 centipoise, about 1,000 centipoise to about 1,000,000 centipoise, about 1,000 centipoise to about 10,000,000 centipoise, about 10,000 centipoise to about 100,000 centipoise, about 10,000 centipoise to about 1,000,000 centipoise, about 10,000 centipoise to about 10,000,000 centipoise, about 100,000 centipoise to about 1,000,000 centipoise, about 100,000 centipoise to about 10,000,000 centipoise, or about 1,000,000 centipoise to about 10,000,000 centipoise. In some embodiments, the pharmaceutical compositions described herein comprise a viscosity between about 0.001 centipoise, about 0.01 centipoise, about 0.1 centipoise, about 1 centipoise, about 10 centipoise, about 100 centipoise, about 1,000 centipoise, about 10,000 centipoise, about 100,000 centipoise, about 1,000,000 centipoise, or about 10,000,000 centipoise. In some embodiments, the pharmaceutical compositions described herein comprise a viscosity between at least about 0.001 centipoise, about 0.01 centipoise, about 0.1 centipoise, about 1 centipoise, about 10 centipoise, about 100 centipoise, about 1,000 centipoise, about 10,000 centipoise, about 100,000 centipoise, or about 1,000,000 centipoise. In some embodiments, the pharmaceutical compositions described herein comprise a viscosity between at most about 0.01 centipoise, about 0.1 centipoise, about 1 centipoise, about 10 centipoise, about 100 centipoise, about 1,000 centipoise, about 10,000 centipoise, about 100,000 centipoise, about 1,000,000 centipoise, or about 10,000,000 centipoise.

In some embodiments, the pharmaceutical compositions described herein comprise a viscosity at 20 degrees Celsius between about 0.001 centipoise to about 10,000,000 centipoise. In some embodiments, the pharmaceutical compositions described herein comprise a viscosity at 20 degrees Celsius between about 0.001 centipoise to about 0.01 centipoise, about 0.001 centipoise to about 0.1 centipoise, about 0.001 centipoise to about 1 centipoise, about 0.001 centipoise to about 10 centipoise, about 0.001 centipoise to about 100 centipoise, about 0.001 centipoise to about 1,000 centipoise, about 0.001 centipoise to about 10,000 centipoise, about 0.001 centipoise to about 100,000 centipoise, about 0.001 centipoise to about 1,000,000 centipoise, about 0.001 centipoise to about 10,000,000 centipoise, about 0.01 centipoise to about 0.1 centipoise, about 0.01 centipoise to about 1 centipoise, about 0.01 centipoise to about 10 centipoise, about 0.01 centipoise to about 100 centipoise, about 0.01 centipoise to about 1,000 centipoise, about 0.01 centipoise to about 10,000 centipoise, about 0.01 centipoise to about 100,000 centipoise, about 0.01 centipoise to about 1,000,000 centipoise, about 0.01 centipoise to about 10,000,000 centipoise, about 0.1 centipoise to about 1 centipoise, about 0.1 centipoise to about 10 centipoise, about 0.1 centipoise to about 100 centipoise, about 0.1 centipoise to about 1,000 centipoise, about 0.1 centipoise to about 10,000 centipoise, about 0.1 centipoise to about 100,000 centipoise, about 0.1 centipoise to about 1,000,000 centipoise, about 0.1 centipoise to about 10,000,000 centipoise, about 1 centipoise to about 10 centipoise, about 1 centipoise to about 100 centipoise, about 1 centipoise to about 1,000 centipoise, about 1 centipoise to about 10,000 centipoise, about 1 centipoise to about 100,000 centipoise, about 1 centipoise to about 1,000,000 centipoise, about 1 centipoise to about 10,000,000 centipoise, about 10 centipoise to about 100 centipoise, about 10 centipoise to about 1,000 centipoise, about 10 centipoise to about 10,000 centipoise, about 10 centipoise to about 100,000 centipoise, about 10 centipoise to about 1,000,000 centipoise, about 10 centipoise to about 10,000,000 centipoise, about 100 centipoise to about 1,000 centipoise, about 100 centipoise to about 10,000 centipoise, about 100 centipoise to about 100,000 centipoise, about 100 centipoise to about 1,000,000 centipoise, about 100 centipoise to about 10,000,000 centipoise, about 1,000 centipoise to about 10,000 centipoise, about 1,000 centipoise to about 100,000 centipoise, about 1,000 centipoise to about 1,000,000 centipoise, about 1,000 centipoise to about 10,000,000 centipoise, about 10,000 centipoise to about 100,000 centipoise, about 10,000 centipoise to about 1,000,000 centipoise, about 10,000 centipoise to about 10,000,000 centipoise, about 100,000 centipoise to about 1,000,000 centipoise, about 100,000 centipoise to about 10,000,000 centipoise, or about 1,000,000 centipoise to about 10,000,000 centipoise. In some embodiments, the pharmaceutical compositions described herein comprise a viscosity at 20 degrees Celsius between about 0.001 centipoise, about 0.01 centipoise, about 0.1 centipoise, about 1 centipoise, about 10 centipoise, about 100 centipoise, about 1,000 centipoise, about 10,000 centipoise, about 100,000 centipoise, about 1,000,000 centipoise, or about 10,000,000 centipoise. In some embodiments, the pharmaceutical compositions described herein comprise a viscosity at 20 degrees Celsius between at least about 0.001 centipoise, about 0.01 centipoise, about 0.1 centipoise, about 1 centipoise, about 10 centipoise, about 100 centipoise, about 1,000 centipoise, about 10,000 centipoise, about 100,000 centipoise, or about 1,000,000 centipoise. In some embodiments, the pharmaceutical compositions described herein comprise a viscosity at 20 degrees Celsius between at most about 0.01 centipoise, about 0.1 centipoise, about 1 centipoise, about 10 centipoise, about 100 centipoise, about 1,000 centipoise, about 10,000 centipoise, about 100,000 centipoise, about 1,000,000 centipoise, or about 10,000,000 centipoise.

In some embodiments, the naloxone containing formulations described herein comprise a viscosity at 20 degrees Celsius between about 0.001 centipoise to about 100,000,000 centipoise. In some embodiments, the naloxone containing formulations described herein comprise a viscosity at 20 degrees Celsius between about 0.001 centipoise to about 0.01 centipoise, about 0.001 centipoise to about 0.1 centipoise, about 0.001 centipoise to about 1 centipoise, about 0.001 centipoise to about 10 centipoise, about 0.001 centipoise to about 100 centipoise, about 0.001 centipoise to about 1,000 centipoise, about 0.001 centipoise to about 10,000 centipoise, about 0.001 centipoise to about 100,000 centipoise, about 0.001 centipoise to about 1,000,000 centipoise, about 0.001 centipoise to about 10,000,000 centipoise, about 0.001 centipoise to about 100,000,000 centipoise, about 0.01 centipoise to about 0.1 centipoise, about 0.01 centipoise to about 1 centipoise, about 0.01 centipoise to about 10 centipoise, about 0.01 centipoise to about 100 centipoise, about 0.01 centipoise to about 1,000 centipoise, about 0.01 centipoise to about 10,000 centipoise, about 0.01 centipoise to about 100,000 centipoise, about 0.01 centipoise to about 1,000,000 centipoise, about 0.01 centipoise to about 10,000,000 centipoise, about 0.01 centipoise to about 100,000,000 centipoise, about 0.1 centipoise to about 1 centipoise, about 0.1 centipoise to about 10 centipoise, about 0.1 centipoise to about 100 centipoise, about 0.1 centipoise to about 1,000 centipoise, about 0.1 centipoise to about 10,000 centipoise, about 0.1 centipoise to about 100,000 centipoise, about 0.1 centipoise to about 1,000,000 centipoise, about 0.1 centipoise to about 10,000,000 centipoise, about 0.1 centipoise to about 100,000,000 centipoise, about 1 centipoise to about 10 centipoise, about 1 centipoise to about 100 centipoise, about 1 centipoise to about 1,000 centipoise, about 1 centipoise to about 10,000 centipoise, about 1 centipoise to about 100,000 centipoise, about 1 centipoise to about 1,000,000 centipoise, about 1 centipoise to about 10,000,000 centipoise, about 1 centipoise to about 100,000,000 centipoise, about 10 centipoise to about 100 centipoise, about 10 centipoise to about 1,000 centipoise, about 10 centipoise to about 10,000 centipoise, about 10 centipoise to about 100,000 centipoise, about 10 centipoise to about 1,000,000 centipoise, about 10 centipoise to about 10,000,000 centipoise, about 10 centipoise to about 100,000,000 centipoise, about 100 centipoise to about 1,000 centipoise, about 100 centipoise to about 10,000 centipoise, about 100 centipoise to about 100,000 centipoise, about 100 centipoise to about 1,000,000 centipoise, about 100 centipoise to about 10,000,000 centipoise, about 100 centipoise to about 100,000,000 centipoise, about 1,000 centipoise to about 10,000 centipoise, about 1,000 centipoise to about 100,000 centipoise, about 1,000 centipoise to about 1,000,000 centipoise, about 1,000 centipoise to about 10,000,000 centipoise, about 1,000 centipoise to about 100,000,000 centipoise, about 10,000 centipoise to about 100,000 centipoise, about 10,000 centipoise to about 1,000,000 centipoise, about 10,000 centipoise to about 10,000,000 centipoise, about 10,000 centipoise to about 100,000,000 centipoise, about 100,000 centipoise to about 1,000,000 centipoise, about 100,000 centipoise to about 10,000,000 centipoise, about 100,000 centipoise to about 100,000,000 centipoise, about 1,000,000 centipoise to about 10,000,000 centipoise, about 1,000,000 centipoise to about 100,000,000 centipoise, or about 10,000,000 centipoise to about 100,000,000 centipoise. In some embodiments, the naloxone containing formulations described herein comprise a viscosity at 20 degrees Celsius between about 0.001 centipoise, about 0.01 centipoise, about 0.1 centipoise, about 1 centipoise, about 10 centipoise, about 100 centipoise, about 1,000 centipoise, about 10,000 centipoise, about 100,000 centipoise, about 1,000,000 centipoise, about 10,000,000 centipoise, or about 100,000,000 centipoise. In some embodiments, the naloxone containing formulations described herein comprise a viscosity at 20 degrees Celsius between at least about 0.001 centipoise, about 0.01 centipoise, about 0.1 centipoise, about 1 centipoise, about 10 centipoise, about 100 centipoise, about 1,000 centipoise, about 10,000 centipoise, about 100,000 centipoise, about 1,000,000 centipoise, or about 10,000,000 centipoise. In some embodiments, the naloxone containing formulations described herein comprise a viscosity at 20 degrees Celsius between at most about 0.01 centipoise, about 0.1 centipoise, about 1 centipoise, about 10 centipoise, about 100 centipoise, about 1,000 centipoise, about 10,000 centipoise, about 100,000 centipoise, about 1,000,000 centipoise, about 10,000,000 centipoise, or about 100,000,000 centipoise.

In some embodiments, the naloxone containing formulations described herein comprise a viscosity at 20 degrees Celsius at least about 0.001 centipoise to about 100,000,000 centipoise. In some embodiments, the naloxone containing formulations described herein comprise a viscosity at 20 degrees Celsius at least about 0.001 centipoise to about 0.01 centipoise, about 0.001 centipoise to about 0.1 centipoise, about 0.001 centipoise to about 1 centipoise, about 0.001 centipoise to about 10 centipoise, about 0.001 centipoise to about 100 centipoise, about 0.001 centipoise to about 1,000 centipoise, about 0.001 centipoise to about 10,000 centipoise, about 0.001 centipoise to about 100,000 centipoise, about 0.001 centipoise to about 1,000,000 centipoise, about 0.001 centipoise to about 10,000,000 centipoise, about 0.001 centipoise to about 100,000,000 centipoise, about 0.01 centipoise to about 0.1 centipoise, about 0.01 centipoise to about 1 centipoise, about 0.01 centipoise to about 10 centipoise, about 0.01 centipoise to about 100 centipoise, about 0.01 centipoise to about 1,000 centipoise, about 0.01 centipoise to about 10,000 centipoise, about 0.01 centipoise to about 100,000 centipoise, about 0.01 centipoise to about 1,000,000 centipoise, about 0.01 centipoise to about 10,000,000 centipoise, about 0.01 centipoise to about 100,000,000 centipoise, about 0.1 centipoise to about 1 centipoise, about 0.1 centipoise to about 10 centipoise, about 0.1 centipoise to about 100 centipoise, about 0.1 centipoise to about 1,000 centipoise, about 0.1 centipoise to about 10,000 centipoise, about 0.1 centipoise to about 100,000 centipoise, about 0.1 centipoise to about 1,000,000 centipoise, about 0.1 centipoise to about 10,000,000 centipoise, about 0.1 centipoise to about 100,000,000 centipoise, about 1 centipoise to about 10 centipoise, about 1 centipoise to about 100 centipoise, about 1 centipoise to about 1,000 centipoise, about 1 centipoise to about 10,000 centipoise, about 1 centipoise to about 100,000 centipoise, about 1 centipoise to about 1,000,000 centipoise, about 1 centipoise to about 10,000,000 centipoise, about 1 centipoise to about 100,000,000 centipoise, about 10 centipoise to about 100 centipoise, about 10 centipoise to about 1,000 centipoise, about 10 centipoise to about 10,000 centipoise, about 10 centipoise to about 100,000 centipoise, about 10 centipoise to about 1,000,000 centipoise, about 10 centipoise to about 10,000,000 centipoise, about 10 centipoise to about 100,000,000 centipoise, about 100 centipoise to about 1,000 centipoise, about 100 centipoise to about 10,000 centipoise, about 100 centipoise to about 100,000 centipoise, about 100 centipoise to about 1,000,000 centipoise, about 100 centipoise to about 10,000,000 centipoise, about 100 centipoise to about 100,000,000 centipoise, about 1,000 centipoise to about 10,000 centipoise, about 1,000 centipoise to about 100,000 centipoise, about 1,000 centipoise to about 1,000,000 centipoise, about 1,000 centipoise to about 10,000,000 centipoise, about 1,000 centipoise to about 100,000,000 centipoise, about 10,000 centipoise to about 100,000 centipoise, about 10,000 centipoise to about 1,000,000 centipoise, about 10,000 centipoise to about 10,000,000 centipoise, about 10,000 centipoise to about 100,000,000 centipoise, about 100,000 centipoise to about 1,000,000 centipoise, about 100,000 centipoise to about 10,000,000 centipoise, about 100,000 centipoise to about 100,000,000 centipoise, about 1,000,000 centipoise to about 10,000,000 centipoise, about 1,000,000 centipoise to about 100,000,000 centipoise, or about 10,000,000 centipoise to about 100,000,000 centipoise. In some embodiments, the naloxone containing formulations described herein comprise a viscosity at 20 degrees Celsius at least about 0.001 centipoise, about 0.01 centipoise, about 0.1 centipoise, about 1 centipoise, about 10 centipoise, about 100 centipoise, about 1,000 centipoise, about 10,000 centipoise, about 100,000 centipoise, about 1,000,000 centipoise, about 10,000,000 centipoise, or about 100,000,000 centipoise. In some embodiments, the naloxone containing formulations described herein comprise a viscosity at 20 degrees Celsius at least at least about 0.001 centipoise, about 0.01 centipoise, about 0.1 centipoise, about 1 centipoise, about 10 centipoise, about 100 centipoise, about 1,000 centipoise, about 10,000 centipoise, about 100,000 centipoise, about 1,000,000 centipoise, or about 10,000,000 centipoise. In some embodiments, the naloxone containing formulations described herein comprise a viscosity at 20 degrees Celsius at least at most about 0.01 centipoise, about 0.1 centipoise, about 1 centipoise, about 10 centipoise, about 100 centipoise, about 1,000 centipoise, about 10,000 centipoise, about 100,000 centipoise, about 1,000,000 centipoise, about 10,000,000 centipoise, or about 100,000,000 centipoise.

In some embodiments, the naloxone containing formulations described herein comprise a viscosity at 20 degrees Celsius at most about 0.001 centipoise to about 100,000,000 centipoise. In some embodiments, the naloxone containing formulations described herein comprise a viscosity at 20 degrees Celsius at most about 0.001 centipoise to about 0.01 centipoise, about 0.001 centipoise to about 0.1 centipoise, about 0.001 centipoise to about 1 centipoise, about 0.001 centipoise to about 10 centipoise, about 0.001 centipoise to about 100 centipoise, about 0.001 centipoise to about 1,000 centipoise, about 0.001 centipoise to about 10,000 centipoise, about 0.001 centipoise to about 100,000 centipoise, about 0.001 centipoise to about 1,000,000 centipoise, about 0.001 centipoise to about 10,000,000 centipoise, about 0.001 centipoise to about 100,000,000 centipoise, about 0.01 centipoise to about 0.1 centipoise, about 0.01 centipoise to about 1 centipoise, about 0.01 centipoise to about 10 centipoise, about 0.01 centipoise to about 100 centipoise, about 0.01 centipoise to about 1,000 centipoise, about 0.01 centipoise to about 10,000 centipoise, about 0.01 centipoise to about 100,000 centipoise, about 0.01 centipoise to about 1,000,000 centipoise, about 0.01 centipoise to about 10,000,000 centipoise, about 0.01 centipoise to about 100,000,000 centipoise, about 0.1 centipoise to about 1 centipoise, about 0.1 centipoise to about 10 centipoise, about 0.1 centipoise to about 100 centipoise, about 0.1 centipoise to about 1,000 centipoise, about 0.1 centipoise to about 10,000 centipoise, about 0.1 centipoise to about 100,000 centipoise, about 0.1 centipoise to about 1,000,000 centipoise, about 0.1 centipoise to about 10,000,000 centipoise, about 0.1 centipoise to about 100,000,000 centipoise, about 1 centipoise to about 10 centipoise, about 1 centipoise to about 100 centipoise, about 1 centipoise to about 1,000 centipoise, about 1 centipoise to about 10,000 centipoise, about 1 centipoise to about 100,000 centipoise, about 1 centipoise to about 1,000,000 centipoise, about 1 centipoise to about 10,000,000 centipoise, about 1 centipoise to about 100,000,000 centipoise, about 10 centipoise to about 100 centipoise, about 10 centipoise to about 1,000 centipoise, about 10 centipoise to about 10,000 centipoise, about 10 centipoise to about 100,000 centipoise, about 10 centipoise to about 1,000,000 centipoise, about 10 centipoise to about 10,000,000 centipoise, about 10 centipoise to about 100,000,000 centipoise, about 100 centipoise to about 1,000 centipoise, about 100 centipoise to about 10,000 centipoise, about 100 centipoise to about 100,000 centipoise, about 100 centipoise to about 1,000,000 centipoise, about 100 centipoise to about 10,000,000 centipoise, about 100 centipoise to about 100,000,000 centipoise, about 1,000 centipoise to about 10,000 centipoise, about 1,000 centipoise to about 100,000 centipoise, about 1,000 centipoise to about 1,000,000 centipoise, about 1,000 centipoise to about 10,000,000 centipoise, about 1,000 centipoise to about 100,000,000 centipoise, about 10,000 centipoise to about 100,000 centipoise, about 10,000 centipoise to about 1,000,000 centipoise, about 10,000 centipoise to about 10,000,000 centipoise, about 10,000 centipoise to about 100,000,000 centipoise, about 100,000 centipoise to about 1,000,000 centipoise, about 100,000 centipoise to about 10,000,000 centipoise, about 100,000 centipoise to about 100,000,000 centipoise, about 1,000,000 centipoise to about 10,000,000 centipoise, about 1,000,000 centipoise to about 100,000,000 centipoise, or about 10,000,000 centipoise to about 100,000,000 centipoise. In some embodiments, the naloxone containing formulations described herein comprise a viscosity at 20 degrees Celsius at most about 0.001 centipoise, about 0.01 centipoise, about 0.1 centipoise, about 1 centipoise, about 10 centipoise, about 100 centipoise, about 1,000 centipoise, about 10,000 centipoise, about 100,000 centipoise, about 1,000,000 centipoise, about 10,000,000 centipoise, or about 100,000,000 centipoise. In some embodiments, the naloxone containing formulations described herein comprise a viscosity at 20 degrees Celsius at most at least about 0.001 centipoise, about 0.01 centipoise, about 0.1 centipoise, about 1 centipoise, about 10 centipoise, about 100 centipoise, about 1,000 centipoise, about 10,000 centipoise, about 100,000 centipoise, about 1,000,000 centipoise, or about 10,000,000 centipoise. In some embodiments, the naloxone containing formulations described herein comprise a viscosity at 20 degrees Celsius at most at most about 0.01 centipoise, about 0.1 centipoise, about 1 centipoise, about 10 centipoise, about 100 centipoise, about 1,000 centipoise, about 10,000 centipoise, about 100,000 centipoise, about 1,000,000 centipoise, about 10,000,000 centipoise, or about 100,000,000 centipoise.

Described herein, in some instances, are pharmaceutical compositions comprising a gel or a semi-solid formulations. Gels have been defined in various ways. For example, the United States Pharmacopoeia defines gels as semisolid systems consisting of either suspensions made up of small inorganic particles or large organic molecules interpenetrated by a liquid. Gels include a single-phase or a two-phase system. A single-phase gel consists of organic macromolecules distributed uniformly throughout a liquid in such a manner that no apparent boundaries exist between the dispersed macromolecules and the liquid. Some single-phase gels are prepared from synthetic macromolecules (e.g., carbomer) or from natural gums, (e.g., tragacanth). In some embodiments, single-phase gels are generally aqueous, but will also be made using alcohols and oils. Two-phase gels consist of a network of small discrete particles.

In some embodiments, gels are also classified as being hydrophobic or hydrophilic. In certain embodiments, the base of a non-limiting example of a hydrophobic gel comprises a liquid paraffin with polyethylene or fatty oils gelled with colloidal silica, or aluminum or zinc soaps. In contrast, the base of a non-limiting example of a hydrophilic gel comprises water, glycerol, or propylene glycol gelled with a suitable gelling agent (e.g., tragacanth, starch, cellulose derivatives, carboxyvinylpolymers, and magnesium-aluminum silicates). In certain embodiments, the rheology of the compositions disclosed herein is pseudo plastic, plastic, thixotropic, or dilatant.

In some embodiments, the pharmaceutical compositions described herein are naloxone containing gel formulation, and wherein the acceptable carrier comprises water and at least one thickening agent, gelling agent, or viscosity-enhancing agent. In some embodiments, the viscosity-enhancing agent is selected from cellulose-based polymers, polyoxyethylene-polyoxypropylene triblock copolymers, dextran-based polymers, polyvinyl alcohol, dextrin, polyvinylpyrrolidone, polyalkylene glycols, chitosan, collagen, gelatin, hyaluronic acid, or combinations thereof.

In some embodiment, the gel composition described herein is a semi-solid or is in a gelled state before it is nasally administered (e.g. at room temperature). For example, suitable viscosity-enhancing agents for such gels include by way of example only, gelling agents and suspending agents. In one embodiment, the enhanced viscosity formulation does not include a buffer. In other embodiments, the enhanced viscosity formulation comprises a pharmaceutically acceptable buffer. Sodium chloride or other tonicity agents are optionally used to adjust tonicity, if necessary.

By way of example only, the acceptable viscosity agent comprises hydroxypropyl methylcellulose, hydroxyethyl cellulose, polyvinylpyrrolidone, carboxymethyl cellulose, polyvinyl alcohol, sodium chondroitin sulfate, sodium hyaluronate. Other viscosity enhancing agents compatible with the targeted ocular site include, but are not limited to, acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), ceratonia, chitin, carboxymethylated chitosan, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, gum tragacanth, ethyl cellulose, ethylhydroxyethyl cellulose, ethylmethyl cellulose, methyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly(methoxyethoxyethyl methacrylate), hydroxypropyl cellulose, hydroxypropylmethyl-cellulose (HPMC), sodium carboxymethyl-cellulose (CMC), silicon dioxide, polyvinylpyrrolidone (PVP: povidone), Splenda® (dextrose, maltodextrin and sucralose) or combinations thereof. In specific embodiments, the viscosity-enhancing excipient is a combination of MCC and CMC. In another embodiment, the viscosity-enhancing agent is a combination of carboxymethylated chitosan, or chitin, and alginate. The combination of chitin and alginate with the active or therapeutic agents disclosed herein acts as a controlled release formulation, restricting the diffusion of the active or therapeutic agents from the formulation. Moreover, the combination of carboxymethylated chitosan and alginate is optionally used to assist in increasing the permeability of the active or therapeutic agents in the nasal cavity.

In some embodiments, the viscosity agent is present in the pharmaceutical compositions at about 0.001%, 0.005%, 0.010%, 0.015%, 0.020%, 0.025%, 0.030%, 0.035%, 0.040%, 0.045%, 0.050%, 0.055%, 0.060%, 0.065%, 0.070%, 0.075%, 0.080%, 0.085%, 0.090%, 0.095%, 0.1%, 0.2%, 0.3%, 0.4%, 0.5%, 0.6%, 0.7%, 0.8%, 0.9%, 1.0%, 1.5%, 2.0%, 2.5%, 3.0%, 3.5%, 4.0%, 4.5%, 5.0%, 5.5%, or 6%. In some embodiments, the viscosity agent is present in the pharmaceutical compositions from about 0.001% to about 0.05%, from about 0.001% to about 0.04%, from about 0.001% to about 0.03%, from about 0.001% to about 0.025%, from about 0.001% to about 0.02%, from about 0.001% to about 0.01%, from about 0.001% to about 0.008%, or from about 0.001% to about 0.005%. In some cases, the percentage is a weight percentage.

Suitable gelling agents for use in preparation of the gel formulation include, but are not limited to, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum and any combinations or mixtures thereof. In some other embodiments, hydroxypropylmethylcellulose (Methocel®) is utilized as the gelling agent. In certain embodiments, the viscosity enhancing agents described herein are also utilized as the gelling agent for the gel formulations presented herein.

In some instances, the gelling agent comprises, but is not limited to, poloxamer (e.g. Poloxamer 407), tetronics, ethyl (hydroxyethyl) cellulose, cellulose acetate phthalate (CAP), carbopol (e.g. Carbopol 1342P NF, Carbopol 980 NF), alginates (e.g. low acetyl gellan gum (Gelrite®)), gellan, hyaluronic acid, pluronics (e.g. Pluronic F-127), chitosan, polyvinyl alcohol (PVA), polyvinylpyrrolidone (PVP), dextran, hydroxy propyl methyl cellulose (HPMC), hydroxyethylcellulose (HEC), methylcellulose (MC), thiolated xyloglucan, polymethacrilic acid (PMMA), polyethylene glycol (PEG), pseudolatexes, xyloglucans, or combinations thereof.

In some instances, the gel formation further comprises a permeation enhancer. In some instances, the permeation enhancer comprises surfactants (e.g. non-ionic surfactants), benzalkonium chloride, EDTA, surface-active heteroglycosides, calcium chelators, hydroxyl propyl beta cyclodextrin (HP beta CD), bile salts, and the like. In some instances, the permeation enhancer is EDTA. In some embodiments, EDTA is present in the composition at about 0.001%, 0.005%, 0.010%, 0.015%, 0.020%, 0.025%, 0.030%, 0.035%, 0.040%, 0.045%, 0.050%, 0.055%, 0.060%, 0.065%, 0.070%, 0.075%, 0.080%, 0.085%, 0.090%, 0.095%, 0.1%, 0.2%, 0.3%, 0.4%, 0.5%, 0.6%, 0.7%, 0.8%, 0.9%, 1.0%, 1.5%, 2.0%, 2.5% or 3.0%. In some embodiments, EDTA is present in the composition from about 0.001% to about 0.05%, from about 0.001% to about 0.04%, from about 0.001% to about 0.03%, from about 0.001% to about 0.025%, from about 0.001% to about 0.02%, from about 0.001% to about 0.01%, from about 0.001% to about 0.008%, or from about 0.001% to about 0.005%. In some cases, the percentage is a weight percentage.

In some embodiments, the viscosity-enhancing agent is a cellulose-based polymer selected from cellulose gum, alkylcellulose, hydroxyl-alkyl cellulose, hydroxyl-alkyl alkylcellulose, carboxy-alkyl cellulose, or combinations thereof. In some embodiments, the viscosity-enhancing agent is hydroxyl-alkyl alkylcellulose. In some embodiment, the viscosity-enhancing agent is hydroxypropyl methylcellulose.

In certain embodiments, the enhanced viscosity formulation is characterized by a phase transition between room temperature and body temperature (including an individual with a serious fever, e.g., up to about 42° C.). In some embodiments, the phase transition occurs at 1° C. below body temperature, at 2° C. below body temperature, at 3° C. below body temperature, at 4° C. below body temperature, at 6° C. below body temperature, at 8° C. below body temperature, or at 10° C. below body temperature. In some embodiments, the phase transition occurs at about 15° C. below body temperature, at about 20° C. below body temperature, or at about 25° C. below body temperature. In specific embodiments, the gelation temperature (Tgel) of a formulation described herein is about 20° C., about 25° C., or about 30° C. In certain embodiments, the gelation temperature (Tgel) of a formulation described herein is about 35° C., or about 40° C. Included within the definition of body temperature is the body temperature of a healthy individual, or an unhealthy individual, including an individual with a fever (up to ~42° C.). In some embodiments, the pharmaceutical compositions described herein are liquids at about room temperature and are administered at or about room temperature.

Copolymers polyoxypropylene and polyoxyethylene (e.g. polyoxyethylene-polyoxypropylene triblock copolymers) form thermosetting gels when incorporated into aqueous solutions. These polymers have the ability to change from the liquid state to the gel state at temperatures close to body temperature, therefore allowing useful formulations that are applied to the targeted ocular site. The liquid state-to-gel state phase transition is dependent on the polymer concentration and the ingredients in the solution.

In some embodiments, the amount of thermosetting polymer in any formulation described herein is about 10%, about 15%, about 20%, about 25%, about 30%, about 35%, or about 40% of the total weight of the formulation. In some embodiments, the amount of thermosetting polymer in any formulation described herein is about 10%, about 11%, about 12%, about 13%, about 14%, about 15%, about 16%, about 17%, about 18%, about 19%, about 20%, about 21%, about 22%, about 23%, about 24%, or about 25% of the total weight of the formulation. In some embodiments, the amount of thermosetting polymer (e.g., Poloxamer 407) in any formulation described herein is about 7.5% of the total weight of the formulation. In some embodiments, the amount of thermosetting polymer (e.g., Poloxamer 407) in any formulation described herein is about 10% of the total weight of the formulation. In some embodiments, the amount of thermosetting polymer (e.g., Poloxamer 407) in any formulation described herein is about 11% of the total weight of the formulation. In some embodiments, the amount of thermosetting polymer (e.g., Poloxamer 407) in any formulation described herein is about 12% of the total weight of the formulation. In some embodiments, the amount of thermosetting polymer (e.g., Poloxamer 407) in any formulation described herein is about 13% of the total weight of the formulation. In some embodiments, the amount of thermosetting polymer (e.g., Poloxamer 407) in any formulation described herein is about 14% of the total weight of the formulation. In some embodiments, the amount of thermosetting polymer (e.g., Poloxamer 407) in any formulation described herein is about 15% of the total weight of the formulation. In some embodiments, the amount of thermosetting polymer (e.g., Poloxamer 407) in any formulation described herein is about 16% of the total weight of the formulation. In some embodiments, the amount of thermosetting polymer (e.g., Poloxamer 407) in any formulation described herein is about 17% of the total weight of the formulation. In some embodiments, the amount of thermosetting polymer (e.g., Poloxamer 407) in any formulation described herein is about 18% of the total weight of the formulation. In some embodiments, the amount of thermosetting polymer (e.g., Poloxamer 407) in any formulation described herein is about 19% of the total weight of the formulation. In some embodiments, the amount of thermosetting polymer (e.g., Poloxamer 407) in any formulation described herein is about 20% of the total weight of the formulation. In some embodiments, the amount of thermosetting polymer (e.g., Poloxamer 407) in any formulation described herein is about 21% of the total weight of the formulation. In some embodiments, the amount of thermosetting polymer (e.g., Poloxamer 407) in any formulation described herein is about 23% of the total weight of the formulation. In some embodiments, the amount of thermosetting polymer (e.g., Poloxamer 407) in any formulation described herein is about 25% of the total weight of the formulation. In some embodiments, the amount of thickening agent (e.g., a gelling agent) in any formulation described herein is about 1%, about 5%, about 10%, or about 15% of the total weight of the formulation. In some embodiments, the amount of thickening agent (e.g., a gelling agent) in any formulation described herein is about 0.5%, about 1%, about 1.5% about 2%, about 2.5% about 3%, about 3.5%, about 4%, about 4.5%, or about 5% of the total weight of the formulation.

In an alternative embodiment, the thermogel is a PEG-PLGA-PEG triblock copolymer (Jeong et al, Nature (1997), 388:860-2; Jeong et al, J. Control. Release (2000), 63:155-63; Jeong et al, Adv. Drug Delivery Rev. (2002), 54:37-51). The polymer exhibits sol-gel behavior over a concentration of about 5% w/w to about 40% w/w. Depending on the properties desired, the lactide/glycolide molar ratio in the PLGA copolymer ranges from about 1:1 to about 20:1. The resulting copolymers are soluble in water and form a free-flowing liquid at room temperature, but form a hydrogel at body temperature. A commercially available PEG-PLGA-PEG triblock copolymer is RESOMER RGP t50106 manufactured by Boehringer Ingelheim. This material is composed of a PLGA copolymer of 50:50 poly(DL-lactide-co-glycolide) and is 10% w/w of PEG and has a molecular weight of about 6000.

Additional biodegradable thermoplastic polyesters include AtriGel® (provided by Atrix Laboratories, Inc.) and/or those disclosed, e.g., in U.S. Pat. Nos. 5,324,519; 4,938,763; 5,702,716; 5,744,153; and 5,990,194; wherein the suitable biodegradable thermoplastic polyester is disclosed as a thermoplastic polymer. Examples of suitable biodegradable thermoplastic polyesters include polylactides, polyglycolides, polycaprolactones, copolymers thereof, terpolymers thereof, and any combinations thereof. In some such embodiments, the suitable biodegradable thermoplastic polyester is a polylactide, a polyglycolide, a copolymer thereof, a terpolymer thereof, or a combination thereof. In one embodiment, the biodegradable thermoplastic polyester is 50/50 poly(DL-lactide-co-glycolide) having a carboxy terminal group; is present in about 30 wt. % to about 40 wt. % of the composition; and has an average molecular weight of about 23,000 to about 45,000. Alternatively, in another embodiment, the biodegradable thermoplastic polyester is 75/25 poly (DL-lactide-co-glycolide) without a carboxy terminal group; is present in about 40 wt. % to about 50 wt. % of the composition; and has an average molecular weight of about 15,000 to about 24,000. In further or alternative embodiments, the terminal groups of the poly(DL-lactide-co-glycolide) are either hydroxyl, carboxyl, or ester depending upon the method of polymerization. Polycondensation of lactic or glycolic acid provides a polymer with terminal hydroxyl and carboxyl groups. Ring-opening polymerization of the cyclic lactide or glycolide monomers with water, lactic acid, or glycolic acid provides polymers with the same terminal groups. However, ring-opening of the cyclic monomers with a monofunctional alcohol such as methanol, ethanol, or 1-dodecanol provides a polymer with one hydroxyl group and one ester terminal groups. Ring-opening polymerization of the cyclic monomers with a diol such as 1,6-hexanediol or polyethylene glycol provides a polymer with only hydroxyl terminal groups.

Since the polymer systems of thermosetting gels dissolve more completely at reduced temperatures, methods of solubilization include adding the required amount of polymer to the amount of water to be used at reduced temperatures. Generally after wetting the polymer by shaking, the mixture is capped and placed in a cold chamber or in a thermostatic container at about 0-10° C. in order to dissolve the polymer. The mixture is stirred or shaken to bring about a more rapid dissolution of the thermosetting gel polymer. The active or therapeutic agent and various additives such as buffers, salts, and preservatives are subsequently added and dissolved. In some instances the pharmaceutically agent is suspended if it is insoluble in water. The pH is modulated by the addition of appropriate buffering agents In some embodiments, the pharmaceutical compositions described herein are naloxone containing formulations. In some instances, the naloxone containing formulations are powder naloxone containing formulations. In some embodiments, the powder naloxone containing formulations comprise powder naloxone hydrochloride. In some embodiments, the average particle size of the powder naloxone compositions can be at least about 0.1 µm to about 1,000 µm. In some embodiments, the average particle size of the powder naloxone compositions can be at least about 0.1 µm to about 0.2 µm, about 0.1 µm to about 0.5 µm, about 0.1 µm to about 1 µm, about 0.1 µm to about 2 µm, about 0.1 µm to about 5 µm, about 0.1 µm to about 10 µm, about 0.1 µm to about 20 µm, about 0.1 µm to about 50 µm, about 0.1 µm to about 100 µm, about 0.1 µm to about 500 µm, about 0.1 µm to about 1,000 µm, about 0.2 µm to about 0.5 µm, about 0.2 µm to about 1 µm, about 0.2 µm to about 2 µm, about 0.2 µm to about 5 µm, about 0.2 µm to about 10 µm, about 0.2 µm to about 20 µm, about 0.2 µm to about 50 µm, about 0.2 µm to about 100 µm, about 0.2 µm to about 500 µm, about 0.2 µm to about 1,000 µm, about 0.5 µm to about 1 µm, about 0.5 µm to about 2 µm, about 0.5 µm to about 5 µm, about 0.5 µm to about 10 µm, about 0.5 µm to about 20 µm, about 0.5 µm to about 50 µm, about 0.5 µm to about 100 µm, about 0.5 µm to about 500 µm, about 0.5 µm to about 1,000 µm, about 1 µm to about 2 µm, about 1 µm to about 5 µm, about 1 µm to about 10 µm, about 1 µm to about 20 µm, about 1 µm to about 50 µm, about 1 µm to about 100 µm, about 1 µm to about 500 µm, about 1 µm to about 1,000 µm, about 2 µm to about 5 µm, about 2 µm to about 10 µm, about 2 µm to about 20 µm, about 2 µm to about 50 µm, about 2 µm to about 100 µm, about 2 µm to about 500 µm, about 2 µm to about 1,000 µm, about 5 µm to about 10 µm, about 5 µm to about 20 µm, about 5 µm to about 50 µm, about 5 µm to about 100 µm, about 5 µm to about 500 µm, about 5 µm to about 1,000 µm, about 10 µm to about 20 µm, about 10 µm to about 50 µm, about 10 µm to about 100 µm, about 10 µm to about 500 µm, about 10 µm to about 1,000 µm, about 20 µm to about 50 µm, about 20 µm to about 100 µm, about 20 µm to about 500 µm, about 20 µm to about 1,000 µm, about 50 µm to about 100 µm, about 50 µm to about 500 µm, about 50 µm to about 1,000 µm, about 100 µm to about 500 µm, about 100 µm to about 1,000 µm, or about 500 µm to about 1,000 µm. In some embodiments, the average particle size of the powder naloxone compositions can be at least about 0.1 µm, about 0.2 µm, about 0.5 µm, about 1 µm, about 2 µm, about 5 µm, about 10 µm, about 20 µm, about 50 µm, about 100 µm, about 500 µm, or about 1,000 µm. In some embodiments, the average particle size of the powder naloxone compositions can be at least at least about 0.1 µm, about 0.2 µm, about 0.5 µm, about 1 µm, about 2 µm, about 5 µm, about 10 µm, about 20 µm, about 50 µm, about 100 µm, or about 500 µm. In some embodiments, the average particle size of the powder naloxone compositions can be at least at most about 0.2 µm, about 0.5 µm, about 1 µm, about 2 µm, about 5 µm, about 10 µm, about 20 µm, about 50 µm, about 100 µm, about 500 µm, or about 1,000 µm.

In some embodiments, the average particle size of the powder naloxone compositions can be at most about 0.1 μm to about 1,000 μm. In some embodiments, the average particle size of the powder naloxone compositions can be at most about 0.1 μm to about 0.2 μm, about 0.1 μm to about 0.5 μm, about 0.1 μm to about 1 μm, about 0.1 μm to about 2 μm, about 0.1 μm to about 5 μm, about 0.1 μm to about 10 μm, about 0.1 μm to about 20 μm, about 0.1 μm to about 50 μm, about 0.1 μm to about 100 μm, about 0.1 μm to about 500 μm, about 0.1 μm to about 1,000 μm, about 0.2 μm to about 0.5 μm, about 0.2 μm to about 1 μm, about 0.2 μm to about 2 μm, about 0.2 μm to about 5 μm, about 0.2 μm to about 10 μm, about 0.2 μm to about 20 μm, about 0.2 μm to about 50 μm, about 0.2 μm to about 100 μm, about 0.2 μm to about 500 μm, about 0.2 μm to about 1,000 μm, about 0.5 μm to about 1 μm, about 0.5 μm to about 2 μm, about 0.5 μm to about 5 μm, about 0.5 μm to about 10 μm, about 0.5 μm to about 20 μm, about 0.5 μm to about 50 μm, about 0.5 μm to about 100 μm, about 0.5 μm to about 500 μm, about 0.5 μm to about 1,000 μm, about 1 μm to about 2 μm, about 1 μm to about 5 μm, about 1 μm to about 10 μm, about 1 μm to about 20 μm, about 1 μm to about 50 μm, about 1 μm to about 100 μm, about 1 μm to about 500 μm, about 1 μm to about 1,000 μm, about 2 μm to about 5 μm, about 2 μm to about 10 μm, about 2 μm to about 20 μm, about 2 μm to about 50 μm, about 2 μm to about 100 μm, about 2 μm to about 500 μm, about 2 μm to about 1,000 μm, about 5 μm to about 10 μm, about 5 μm to about 20 μm, about 5 μm to about 50 μm, about 5 μm to about 100 μm, about 5 μm to about 500 μm, about 5 μm to about 1,000 μm, about 10 μm to about 20 μm, about 10 μm to about 50 μm, about 10 μm to about 100 μm, about 10 μm to about 500 μm, about 10 μm to about 1,000 μm, about 20 μm to about 50 μm, about 20 μm to about 100 μm, about 20 μm to about 500 μm, about 20 μm to about 1,000 μm, about 50 μm to about 100 μm, about 50 μm to about 500 μm, about 50 μm to about 1,000 μm, about 100 μm to about 500 μm, about 100 μm to about 1,000 μm, or about 500 μm to about 1,000 μm. In some embodiments, the average particle size of the powder naloxone compositions can be at most about 0.1 μm, about 0.2 μm, about 0.5 μm, about 1 μm, about 2 μm, about 5 μm, about 10 μm, about 20 μm, about 50 μm, about 100 μm, about 500 μm, or about 1,000 μm. In some embodiments, the average particle size of the powder naloxone compositions can be at most at least about 0.1 μm, about 0.2 μm, about 0.5 μm, about 1 μm, about 2 μm, about 5 μm, about 10 μm, about 20 μm, about 50 μm, about 100 μm, or about 500 μm. In some embodiments, the average particle size of the powder naloxone compositions can be at most at most about 0.2 μm, about 0.5 μm, about 1 μm, about 2 μm, about 5 μm, about 10 μm, about 20 μm, about 50 μm, about 100 μm, about 500 μm, or about 1,000 μm.

In some embodiments, the powder naloxone compositions comprise powder naloxone at at least 1%, 2%, 5%, 10%, 20%, or 50% of total weight of the naloxone containing formulation. In some embodiments, the powder naloxone compositions comprise powder naloxone at at most 1%, 2%, 5%, 10%, 20%, or 50% of total weight of the naloxone containing formulation. In some embodiments, the powder naloxone compositions comprise powder naloxone at about 1%, 2%, 5%, 10%, 20%, or 50% of total weight of the naloxone containing formulation.

Pharmaceutical compositions including therapeutic or active agents that are manufactured in a conventional manner, for example, by means of conventional mixing, dissolving, granulating, dragee-making, levigating, emulsifying, encapsulating, entrapping or compression processes.

The pharmaceutical compositions can include at least a therapeutic agent as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity. In some embodiments, therapeutic agents exist in unsolvated form or in solvated forms with pharmaceutically acceptable solvents such as water, ethanol, and the like. The solvated forms of the therapeutic agents are also considered to be disclosed herein.

In some embodiments, a therapeutic agent or active can exist as a tautomer. All tautomers are included within the scope of the agents presented herein. As such, it is to be understood that a therapeutic agent or a salt thereof can exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they can be regarded as different isomeric forms of the same compound.

In some embodiments, a therapeutic agent exists as an enantiomer, diastereomer, or other steroisomeric form. The agents disclosed herein include all enantiomeric, diastereomeric, and epimeric forms as well as mixtures thereof.

In some embodiments, therapeutic agents described herein can be prepared as prodrugs. A "prodrug" refers to an agent that is converted into the parent drug in vivo. Prodrugs are often useful because, in some situations, they can be easier to administer than the parent drug. They can, for instance, be bioavailable by nasal administration whereas the parent is not. The prodrug can also have improved solubility in pharmaceutical compositions over the parent drug. An example, without limitation, of a prodrug would be a therapeutic agent described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. In certain embodiments, upon in vivo administration, a prodrug is chemically converted to the biologically, pharmaceutically or therapeutically active form of the therapeutic agent. In certain embodiments, a prodrug is enzymatically metabolized by one or more steps or processes to the biologically, pharmaceutically or therapeutically active form of the therapeutic agent. Prodrug forms of the therapeutic agents, wherein the prodrug is metabolized in vivo to produce an agent as set forth herein are included within the scope of the claims. Prodrug forms of the herein described therapeutic agents, wherein the prodrug is metabolized in vivo to produce an agent as set forth herein are included within the scope of the claims. In some cases, some of the therapeutic agents described herein can be a prodrug for another derivative or active compound. In some embodiments described herein, hydrazones are metabolized in vivo to produce a therapeutic agent.

The pharmaceutical compositions described herein are formulated into any suitable dosage form, including but not limited to, aqueous oral dispersions, liquids, gels, syrups, elixirs, slurries, suspensions, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In one aspect, a therapeutic agent as discussed herein, e.g., therapeutic agent is formulated into a pharmaceutical composition suitable for intramuscular, subcutaneous, or intravenous injection. In one aspect, formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles include water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. In some embodiments, formulations suitable for subcutaneous injection also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like.

In some embodiments the pharmaceutical compositions described herein can be formulated in aqueous solutions or in physiologically compatible buffers such as Hank's solution, Ringer's solution, or saline buffer. For transmucosal administration, penetration agents appropriate to the barrier to be permeated can be used in the formulation. Such penetration agents are generally known in the art.

Representative intranasal formulations are described in, for example, U.S. Pat. Nos. 4,476,116, 5,116,817 and 6,391,452. Formulations that include a therapeutic agent are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005. The choice of suitable carriers is dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents are optionally present. Preferably, the nasal dosage form should be isotonic with nasal secretions.

Buccal formulations that include a therapeutic agent are administered using a variety of formulations known in the art. For example, such formulations include, but are not limited to, U.S. Pat. Nos. 4,229,447, 4,596,795, 4,755,386, and 5,739,136. In addition, the buccal dosage forms described herein can further include a bioerodible (hydrolysable) polymeric carrier that also serves to adhere the dosage form to the buccal mucosa. For buccal or sublingual administration, the compositions can take the form of tablets, lozenges, or gels formulated in a conventional manner.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

Suitable disintegrants for use in the solid dosage forms described herein include, but are not limited to, natural starch such as corn starch or potato starch, a pregelatinized starch, or sodium starch glycolate, a cellulose such as methylcrystalline cellulose, methylcellulose, microcrystalline cellulose, croscarmellose, or a cross-linked cellulose, such as cross-linked sodium carboxymethylcellulose, cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a gum such as agar, guar, locust bean, Karaya, pectin, or tragacanth, sodium starch glycolate, bentonite, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose, hydroxypropylmethylcellulose, hydroxypropylmethylcellulose acetate stearate, hydroxyethylcellulose, hydroxypropylcellulose, ethylcellulose, and microcrystalline cellulose, microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose, glucose, dextrose, molasses, mannitol, sorbitol, xylitol, lactose, a natural or synthetic gum such as acacia, tragacanth, ghatti gum, mucilage of isapol husks, starch, polyvinylpyrrolidone, larch arabogalactan, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Binder levels of up to 70% in tablet formulations is common.

Suitable lubricants or glidants for use in the solid dosage forms described herein include, but are not limited to, stearic acid, calcium hydroxide, talc, corn starch, sodium stearyl fumarate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely illustrative, and not limiting, of the types of additives that can be included in solid dosage forms of the pharmaceutical compositions described herein. The amounts of such additives can be readily determined by one skilled in the art, according to the particular properties desired.

In various embodiments, the particles of a therapeutic agents and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In other embodiments, a powder including a therapeutic agent is formulated to include one or more pharmaceutical excipients and flavors. Such a powder is prepared, for example, by mixing the therapeutic agent and optional pharmaceutical excipients to form a bulk blend composition. Additional embodiments also include a suspending agent and/or a wetting agent. This bulk blend is uniformly subdivided into unit dosage packaging or multi-dosage packaging units.

In some embodiments, the pharmaceutical dosage forms are formulated to provide a controlled release of a therapeutic agent. Controlled release refers to the release of the therapeutic agent from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to an individual over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In other embodiments, the formulations described herein are delivered using a pulsatile dosage form. A pulsatile dosage form is capable of providing one or more immediate release pulses at predetermined time points after a controlled lag time or at specific sites. Illustrative pulsatile dosage forms and methods of their manufacture are disclosed in U.S. Pat. Nos. 5,011,692, 5,017,381, 5,229,135, 5,840,329 and 5,837,284. In one embodiment, the pulsatile dosage form includes at least two groups of particles, (i.e. multiparticulate) each containing the formulation described herein. The first group of particles provides a substantially immediate dose of a therapeutic agent upon ingestion by a mammal. The first group of particles can be either uncoated or include a coating and/or sealant. In one aspect, the second group of particles comprises coated particles. The coating on the second group of particles provides a delay of from about 2 hours to about 7 hours following ingestion before release of the second dose. Suitable coatings for pharmaceutical compositions are described herein or known in the art.

In some embodiments, pharmaceutical formulations are provided that include particles of a therapeutic agent and at least one dispersing agent or suspending agent for oral administration to an individual. The formulations can be a powder and/or granules for suspension, and upon admixture with water, a substantially uniform suspension is obtained.

In some embodiments, particles formulated for controlled release are incorporated in a gel or a patch.

In some embodiments, the liquid formulations also include inert diluents commonly used in the art, such as water or other solvents, solubilizing agents, and emulsifiers. Illustrative emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

Furthermore, pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, pharmaceutical compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In one embodiment, the aqueous suspensions and dispersions described herein remain in a homogenous state, as defined in The USP Pharmacists' Pharmacopeia (2005 edition, chapter 905), for at least 4 hours. In one embodiment, an aqueous suspension is re-suspended into a homogenous suspension by physical agitation lasting less than 1 minute. In still another embodiment, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch, or sodium starch glycolate; a cellulose such as methylcrystalline cellulose, methylcellulose, croscarmellose, or a cross-linked cellulose, such as cross-linked sodium carboxymethylcellulose, cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein include, for example, hydrophilic polymers, electrolytes, Tween 60 or 80, PEG, polyvinylpyrrolidone, and the carbohydrate-based dispersing agents such as, for example, hydroxypropylcellulose and hydroxypropyl cellulose ethers, hydroxypropyl methylcellulose and hydroxypropyl methylcellulose ethers, carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer, 4-(1,1,3,3-tetramethylbutyl)-phenol polymer with ethylene oxide and formaldehyde (also known as tyloxapol), poloxamers; and poloxamines. In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers; hydroxypropyl methylcellulose and hydroxypropyl methylcellulose ethers; carboxymethylcellulose sodium; methylcellulose; hydroxyethylcellulose; hydroxypropylmethyl-cellulose phthalate; hydroxypropylmethyl-cellulose acetate stearate; noncrystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers; or poloxamines.

Wetting agents suitable for the aqueous suspensions and dispersions described herein include, but are not limited to, cetyl alcohol, glycerol monostearate, polyoxyethylene sorbitan fatty acid esters (e.g., the commercially available Tweens® such as e.g., Tween 20® and Tween 80®, and polyethylene glycols, oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

In some embodiments, a therapeutic agent is prepared as transdermal dosage form. In some embodiments, the transdermal formulations described herein include at least three components: (1) a therapeutic agent; (2) a penetration enhancer; and (3) an optional aqueous adjuvant. In some embodiments the transdermal formulations include additional components such as, but not limited to, gelling agents, creams and ointment bases, and the like. In some embodiments, the transdermal formulation is presented as a patch or a wound dressing. In some embodiments, the transdermal formulation further include a woven or non-woven backing material to enhance absorption and prevent the removal of the transdermal formulation from the skin. In other embodiments, the transdermal formulations described herein can maintain a saturated or supersaturated state to promote diffusion into the skin.

In one aspect, formulations suitable for transdermal administration of a therapeutic agent described herein employ transdermal delivery devices and transdermal delivery patches and can be lipophilic emulsions or buffered, aqueous solutions, dissolved and/or dispersed in a polymer or an adhesive. In one aspect, such patches are constructed for continuous, pulsatile, or on demand delivery of pharmaceutical agents. Still further, transdermal delivery of the therapeutic agents described herein can be accomplished by means of iontophoretic patches and the like. In one aspect, transdermal patches provide controlled delivery of a therapeutic agent. In one aspect, transdermal devices are in the form of a bandage comprising a backing member, a reservoir containing the therapeutic agent optionally with carriers, optionally a rate controlling barrier to deliver the therapeutic agent to the skin of the host at a controlled and predetermined rate over a prolonged period of time, and means to secure the device to the skin.

In further embodiments, topical formulations include gel formulations (e.g., gel patches which adhere to the skin). In some of such embodiments, a gel composition includes any polymer that forms a gel upon contact with the body (e.g., gel formulations comprising hyaluronic acid, pluronic polymers, poly(lactic-co-glycolic acid (PLGA)-based polymers or the like). In some forms of the compositions, the formulation comprises a low-melting wax such as, but not limited to, a mixture of fatty acid glycerides, optionally in combination with cocoa butter which is first melted. Optionally, the formulations further comprise a moisturizing agent.

In certain embodiments, delivery systems for pharmaceutical therapeutic agents can be employed, such as, for example, liposomes and emulsions. In certain embodiments, compositions provided herein can also include an mucoadhesive polymer, selected from among, for example, carboxymethylcellulose, carbomer (acrylic acid polymer), poly (methylmethacrylate), polyacrylamide, polycarbophil, acrylic acid/butyl acrylate copolymer, sodium alginate and dextran.

In some embodiments, a therapeutic agent described herein can be administered topically and can be formulated into a variety of topically administrable compositions, such as solutions, suspensions, lotions, gels, pastes, medicated sticks, balms, creams or ointments. Such pharmaceutical therapeutic agents can contain solubilizers, stabilizers, tonicity enhancing agents, buffers and preservatives.

EXAMPLES

The following illustrative examples are representative of embodiments of the stimulation, systems, and methods described herein and are not meant to be limiting in any way.

Example 1. Treatment of Opioid Overdose with Nasal Trumpet

An individual is hunched over due to opioid overdose. His family member breaks the frangible connection by removing the cover of the nasal trumpet (FIG. 13) from the applicator. The removal of the cover also breaks the hermetic seals of the nasal trumpet. His family member inserts the nasal trumpet into the nasal passage of the individual. A pre-metered dose of naloxone containing formulation is delivered by the nasal trumpet directly contacting with the mucosal membrane of the nasal cavity of the individual. The delivery is completed after 5 seconds, and the naloxone containing formulation stays in the nasal passage for another 5 seconds. The effect of opioid overdose is reversed, and individual regains consciences shortly after receiving the naloxone containing formulation.

Example 2. Treatment of Opioid Overdose with Nasal Roller-Ball

An individual is hunched over due to opioid overdose. His family member breaks the frangible connection by removing the cover of the nasal roller-ball (FIG. 14) from the applicator. The removal of the cover also breaks the hermetic seals of the nasal roller-ball. His family member inserts the nasal roller-ball into the nasal passage of the individual. A pre-metered dose of naloxone containing formulation is delivered by the nasal roller-ball by his family member moving the roller-ball in the nasal passage of the individual. The effect of opioid overdose is reversed, and individual regains consciences shortly after receiving the naloxone containing formulation.

Example 3. Treatment of Opioid Overdose with Nasal Swab

An individual is hunched over due to opioid overdose. His family member breaks the frangible connection by removing the cover of the nasal swab (FIG. 12) from the applicator. The removal of the cover also breaks the hermetic seals of the nasal swab. His family member inserts the nasal swab into the nasal passage of the individual. A pre-metered dose of naloxone containing formulation, absorbed by the swab, is delivered by the nasal swab by his family member inserting and leaving the nasal swab in the nasal passage of the individual. The effect of opioid overdose is reversed, and individual regains consciences shortly after receiving the naloxone containing formulation.

Example 4. Treatment of Opioid Overdose with Nasal Balm

An individual is hunched over due to opioid overdose. His family member breaks the frangible connection by removing the cover of the nasal balm (FIG. 15) from the applicator. The removal of the cover also breaks the hermetic seals of the nasal balm. His family member inserts the nasal balm into the nasal passage of the individual. A pre-metered dose of naloxone containing formulation, absorbed by the nasal balm, is delivered by the nasal balm by his family member inserting and leaving the nasal balm in the nasal passage of the individual. The effect of opioid overdose is reversed, and individual regains consciences shortly after receiving the naloxone containing formulation.

Example 5. Treatment of Opioid Overdose with Nasal Stick

An individual is hunched over due to opioid overdose. His family member breaks the frangible connection by removing the cover of the nasal stick dispenser (FIG. 16) from the applicator. The removal of the cover also breaks the hermetic seals of the nasal stick dispenser. His family member inserts the nasal stick dispenser into the nasal passage of the individual. A pre-metered dose of naloxone containing formulation, stored along the shaft of the stick dispenser, is delivered by his family member inserting and rotating the nasal stick dispenser in the nasal passage of the individual. The effect of opioid overdose is reversed, and individual regains consciences shortly after receiving the naloxone containing formulation.

Example 6. Treatment of Opioid Overdose with a Replaceable Applicator

An individual is hunched over due to opioid overdose. His family member breaks the frangible connection by removing the cover of the naloxone dispensing device (FIG. 17E) from the applicator. The removal of the cover also breaks the hermetic seals of the device. His family member inserts the device into the nasal passage of the individual. A pre-metered dose of naloxone containing formulation, stored in the applicator, is delivered by his family member inserting in the nasal passage of the individual. After the individual remaining unresponsive after several minutes, his family member removes the device from the individual's nasal passage. The spent applicator of the device is replaced with a new applicator. A second pre-metered dose of naloxone containing formulation is delivered to the individual by direct contacting the applicator to the nasal passage of the individual. The cumulative delivery of naloxone containing formulation reverses the opioid overdose, and individual regains consciences shortly after.

Example 7. Treatment of Opioid Overdose with Nasal Trumpet and Endotracheal Intubation An individual is hunched over due to opioid overdose. His family member calls emergency medical technicians right away. Upon arrival, an EMT inspects the individual and confirms that the subject is suffering from opioid overdose. The EMT also observes signs of respiratory suppression. The EMT inserts a naloxone dispensing device in the form of a nasal trumpet as shown in FIG. 22. The naloxone containing formulation is dispensing by direct contact of the applicator of the device to a surface of the nasal passage of the subject. Because of the signs of respiratory suppression, the EMT attempts endotracheal intubation by inserting a fiberoptic scope pre-loaded with an endotracheal tube through a lumen in the nasal trumpet. When the fiberoptic scope is partially inserted into the nasal passage, the nasal trumpet is removed by slipping the fiberoptic scope out of the nasal trumpet via a slit along the longitudinal axis of the nasal trumpet. After the nasal trumpet is removed, the fiberoptic scope is inserted further to complete the endotracheal intubation. With the therapeutics effects of the naloxone containing formulation delivered intranasally and the reversing of the collapsed nasal passage by endotracheal intubation reverses the collapsed nasal passage, the individual regains consciences shortly after.

While the foregoing disclosure has been described in some detail for purposes of clarity and understanding, it will be clear to one skilled in the art from a reading of this disclosure that various changes in form and detail can be made without departing from the true scope of the disclosure. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

The invention claimed is:

1. An intranasal delivery device for treating an opioid overdose comprising:
  a nasal applicator comprising a shaft and an applicator tip coupled to the shaft; and
  an absorbent swab material coupled to the applicator tip, wherein,
    the absorbent swab material is preloaded with a pre-metered dose comprising from 50 µL to 450 µL of an aqueous naloxone-containing formulation for treating an opioid overdose, wherein,
      the naloxone-containing formulation has:
        a naloxone HCl concentration of at least 45 mg/mL; and
        a pH from 3.5 to 5.5; and
      the pre-metered dose comprises from 1 mg to 20 mg of naloxone HCl;
    the absorbent swab material is configured to hold the naloxone-containing formulation and to release the pre-metered dose of the naloxone-containing formulation when pressed against the nasal mucosa; and
    the nasal applicator is configured to contact the absorbent swab material to the nasal mucosa between from 1.5 cm to 3.0 cm from an opening of the nasal passage; and
  the applicator tip does not comprise an injection mechanism.

2. The intranasal delivery device of claim 1, wherein the naloxone-containing formulation has a naloxone HCl concentration from 45 mg/mL to 90 mg/mL.

3. The intranasal delivery device of claim 1, wherein the naloxone-containing formulation comprises a stabilizing agent, a tonicity agent, a chelating agent, and a preservative.

4. The intranasal delivery device of claim 1, wherein the pre-metered dose comprises from 100 µL to 300 µL of a naloxone-containing formulation having a concentration of naloxone-HCl from 45 mg/mL to 90 mg/mL.

* * * * *